United States Patent
Bharadwaj et al.

(10) Patent No.: US 12,138,628 B2
(45) Date of Patent: Nov. 12, 2024

(54) MICROFLUIDIC SYSTEMS AND METHODS OF USE

(71) Applicant: 10x Genomics, Inc., Pleasanton, CA (US)

(72) Inventors: Rajiv Bharadwaj, Pleasanton, CA (US); Kevin Ness, Pleasanton, CA (US); Tobias Daniel Wheeler, Alameda, CA (US)

(73) Assignee: 10x Genomics, Inc., Pleasanton, CA (US)

( * ) Notice: Subject to any disclaimer, the term of this patent is extended or adjusted under 35 U.S.C. 154(b) by 0 days.

(21) Appl. No.: 17/397,146

(22) Filed: Aug. 9, 2021

(65) Prior Publication Data

US 2021/0362157 A1  Nov. 25, 2021

Related U.S. Application Data

(63) Continuation of application No. 16/180,356, filed on Nov. 5, 2018, now Pat. No. 11,084,036, which is a (Continued)

(51) Int. Cl.
*B01L 3/00* (2006.01)
*G01N 1/28* (2006.01)
*G01N 33/487* (2006.01)

(52) U.S. Cl.
CPC ... *B01L 3/502776* (2013.01); *B01L 3/502761* (2013.01); *B01L 3/502784* (2013.01); (Continued)

(58) Field of Classification Search
None
See application file for complete search history.

(56) References Cited

U.S. PATENT DOCUMENTS 2,797,149 A   6/1957   Skeggs
3,047,367 A   7/1962   Kessler
(Continued)

FOREIGN PATENT DOCUMENTS

CN   102292455 A   12/2011
CN   103202812 A   7/2013
(Continued)

OTHER PUBLICATIONS

Ahn et al., "Electrocoalescence of drops synchronized by size-dependent flow in microfluidic channels," Appl Phys Lett. 88: 264105-1-264105-3 (2006).
(Continued)

*Primary Examiner* — Xiaoyun R Xu
(74) *Attorney, Agent, or Firm* — Clark & Elbing LLP

(57) ABSTRACT

Microfluidic channels networks and systems are provided. One network includes a first fluid channel having a first depth dimension; at least a second channel intersecting the first channel at a first intersection; at least a third channel in fluid communication with the first intersection, at least one of the first intersection and the third channel having a depth dimension that is greater than the first depth dimension. Also provided is a flow control system for directing fluids in the network. Systems are additionally provided for flowing disrupted particles into a droplet formation junction, whereby a portion of the disrupted particles or the contents thereof are encapsulated into one or more droplets. Further provided is a method for controlling filling of a microfluidic network by controlling passive valving microfluidic channel network features.

9 Claims, 11 Drawing Sheets

Related U.S. Application Data continuation of application No. PCT/US2017/032520, filed on May 12, 2017.

(60) Provisional application No. 62/335,870, filed on May 13, 2016.

(52) U.S. Cl.
CPC ............ *G01N 1/28* (2013.01); *G01N 33/487* (2013.01); *B01L 2200/0636* (2013.01); *B01L 2200/0652* (2013.01); *B01L 2200/0673* (2013.01); *B01L 2300/0816* (2013.01); *B01L 2300/0851* (2013.01); *B01L 2400/0475* (2013.01)

(56) References Cited

U.S. PATENT DOCUMENTS

| | | |
|---|---|---|
| 3,479,141 A | 11/1969 | Smythe et al. |
| 4,124,638 A | 11/1978 | Hansen |
| 4,253,846 A | 3/1981 | Smythe et al. |
| 4,582,802 A | 4/1986 | Zimmerman et al. |
| 5,137,829 A | 8/1992 | Nag et al. |
| 5,149,625 A | 9/1992 | Church et al. |
| 5,185,099 A | 2/1993 | Delpuech et al. |
| 5,202,231 A | 4/1993 | Drmanac et al. |
| 5,270,183 A | 12/1993 | Corbett et al. |
| 5,413,924 A | 5/1995 | Kosak et al. |
| 5,418,149 A | 5/1995 | Gelfand et al. |
| 5,436,130 A | 7/1995 | Mathies et al. |
| 5,478,893 A | 12/1995 | Ghosh et al. |
| 5,489,523 A | 2/1996 | Mathur |
| 5,512,131 A | 4/1996 | Kumar et al. |
| 5,558,071 A | 9/1996 | Ward et al. |
| 5,585,069 A | 12/1996 | Zanzucchi et al. |
| 5,587,128 A | 12/1996 | Wilding et al. |
| 5,605,793 A | 2/1997 | Stemmer |
| 5,618,711 A | 4/1997 | Gelfand et al. |
| 5,658,548 A | 8/1997 | Padhye et al. |
| 5,695,940 A | 12/1997 | Drmanac et al. |
| 5,700,642 A | 12/1997 | Monforte et al. |
| 5,705,628 A | 1/1998 | Hawkins |
| 5,708,153 A | 1/1998 | Dower et al. |
| 5,736,330 A | 4/1998 | Fulton |
| 5,739,036 A | 4/1998 | Parris |
| 5,744,311 A | 4/1998 | Fraiser et al. |
| 5,756,334 A | 5/1998 | Perler et al. |
| 5,834,197 A | 11/1998 | Parton |
| 5,842,787 A | 12/1998 | Kopf-Sill et al. |
| 5,846,719 A | 12/1998 | Brenner et al. |
| 5,846,727 A | 12/1998 | Soper et al. |
| 5,851,769 A | 12/1998 | Gray et al. |
| 5,856,174 A | 1/1999 | Lipshutz et al. |
| 5,872,010 A | 2/1999 | Karger et al. |
| 5,897,783 A | 4/1999 | Howe et al. |
| 5,900,481 A | 5/1999 | Lough et al. |
| 5,942,609 A | 8/1999 | Hunkapiller et al. |
| 5,958,703 A | 9/1999 | Dower et al. |
| 5,965,443 A | 10/1999 | Reznikoff et al. |
| 5,989,402 A | 11/1999 | Chow et al. |
| 5,994,056 A | 11/1999 | Higuchi |
| 5,997,636 A | 12/1999 | Gamarnik et al. |
| 6,033,880 A | 3/2000 | Haff et al. |
| 6,046,003 A | 4/2000 | Mandecki |
| 6,051,377 A | 4/2000 | Mandecki |
| 6,057,107 A | 5/2000 | Fulton |
| 6,057,149 A | 5/2000 | Burns et al. |
| 6,103,537 A | 8/2000 | Ullman et al. |
| 6,133,436 A | 10/2000 | Koster et al. |
| 6,143,496 A | 11/2000 | Brown et al. |
| 6,159,717 A | 12/2000 | Savakis et al. |
| 6,171,850 B1 | 1/2001 | Nagle et al. |
| 6,172,218 B1 | 1/2001 | Brenner |
| 6,207,384 B1 | 3/2001 | Mekalanos et al. |
| 6,258,571 B1 | 7/2001 | Chumakov et al. |
| 6,265,552 B1 | 7/2001 | Schatz |
| 6,281,254 B1 | 8/2001 | Nakajima et al. |
| 6,291,243 B1 | 9/2001 | Fogarty et al. |
| 6,294,385 B1 | 9/2001 | Goryshin et al. |
| 6,296,020 B1 | 10/2001 | McNeely et al. |
| 6,297,006 B1 | 10/2001 | Drmanac et al. |
| 6,297,017 B1 | 10/2001 | Schmidt et al. |
| 6,303,343 B1 | 10/2001 | Kopf-Sill |
| 6,306,590 B1 | 10/2001 | Mehta et al. |
| 6,327,410 B1 | 12/2001 | Walt et al. |
| 6,355,198 B1 | 3/2002 | Kim et al. |
| 6,361,950 B1 | 3/2002 | Mandecki |
| 6,372,813 B1 | 4/2002 | Johnson et al. |
| 6,379,929 B1 | 4/2002 | Burns et al. |
| 6,406,848 B1 | 6/2002 | Bridgham et al. |
| 6,409,832 B2 | 6/2002 | Weigl et al. |
| 6,432,290 B1 | 8/2002 | Harrison et al. |
| 6,432,360 B1 | 8/2002 | Church |
| 6,481,453 B1 | 11/2002 | O'Connor et al. |
| 6,485,944 B1 | 11/2002 | Church et al. |
| 6,492,118 B1 | 12/2002 | Abrams et al. |
| 6,503,757 B1 | 1/2003 | Chow |
| 6,511,803 B1 | 1/2003 | Church et al. |
| 6,524,456 B1 | 2/2003 | Ramsey et al. |
| 6,569,631 B1 | 5/2003 | Pantoliano et al. |
| 6,579,851 B2 | 6/2003 | Goeke et al. |
| 6,586,176 B1 | 7/2003 | Trnovsky et al. |
| 6,593,113 B1 | 7/2003 | Tenkanen et al. |
| 6,613,752 B2 | 9/2003 | Kay et al. |
| 6,632,606 B1 | 10/2003 | Ullman et al. |
| 6,632,655 B1 | 10/2003 | Mehta et al. |
| 6,670,133 B2 | 12/2003 | Knapp et al. |
| 6,723,513 B2 | 4/2004 | Lexow |
| 6,767,731 B2 | 7/2004 | Hannah |
| 6,800,298 B1 | 10/2004 | Burdick et al. |
| 6,806,052 B2 | 10/2004 | Bridgham et al. |
| 6,806,058 B2 | 10/2004 | Jesperson et al. |
| 6,859,570 B2 | 2/2005 | Walt et al. |
| 6,880,576 B2 | 4/2005 | Karp et al. |
| 6,884,788 B2 | 4/2005 | Bulpitt et al. |
| 6,913,935 B1 | 7/2005 | Thomas |
| 6,929,859 B2 | 8/2005 | Chandler et al. |
| 6,969,488 B2 | 11/2005 | Bridgham et al. |
| 6,974,669 B2 | 12/2005 | Mirkin et al. |
| 7,041,481 B2 | 5/2006 | Anderson et al. |
| 7,115,400 B1 | 10/2006 | Adessi et al. |
| 7,129,091 B2 | 10/2006 | Ismagilov et al. |
| 7,138,267 B1 | 11/2006 | Jendrisak et al. |
| 7,211,654 B2 | 5/2007 | Gao et al. |
| 7,268,167 B2 | 9/2007 | Higuchi et al. |
| 7,282,370 B2 | 10/2007 | Bridgham et al. |
| 7,294,503 B2 | 11/2007 | Quake et al. |
| 7,297,485 B2 | 11/2007 | Bornarth et al. |
| 7,316,903 B2 | 1/2008 | Yanagihara et al. |
| 7,323,305 B2 | 1/2008 | Leamon et al. |
| 7,329,493 B2 | 2/2008 | Chou et al. |
| 7,425,431 B2 | 9/2008 | Church et al. |
| 7,536,928 B2 | 5/2009 | Kazuno |
| 7,544,473 B2 | 6/2009 | Brenner |
| 7,604,938 B2 | 10/2009 | Takahashi et al. |
| 7,608,434 B2 | 10/2009 | Reznikoff et al. |
| 7,608,451 B2 | 10/2009 | Cooper et al. |
| 7,622,280 B2 | 11/2009 | Holliger et al. |
| 7,638,276 B2 | 12/2009 | Griffiths et al. |
| 7,645,596 B2 | 1/2010 | Williams et al. |
| 7,666,664 B2 | 2/2010 | Sarofim et al. |
| 7,700,325 B2 | 4/2010 | Cantor et al. |
| 7,708,949 B2 | 5/2010 | Stone et al. |
| 7,709,197 B2 | 5/2010 | Drmanac |
| 7,745,178 B2 | 6/2010 | Dong |
| 7,745,218 B2 | 6/2010 | Kim et al. |
| 7,776,927 B2 | 8/2010 | Chu et al. |
| RE41,780 E | 9/2010 | Anderson et al. |
| 7,799,553 B2 | 9/2010 | Mathies et al. |
| 7,842,457 B2 | 11/2010 | Berka et al. |
| 7,901,891 B2 | 3/2011 | Drmanac |
| 7,910,354 B2 | 3/2011 | Drmanac et al. |
| 7,943,671 B2 | 5/2011 | Herminghaus et al. |
| 7,947,477 B2 | 5/2011 | Schroeder |

(56) References Cited

U.S. PATENT DOCUMENTS

| | | |
|---|---|---|
| 7,960,104 B2 | 6/2011 | Drmanac et al. |
| 7,968,287 B2 | 6/2011 | Griffiths et al. |
| 7,972,778 B2 | 7/2011 | Brown et al. |
| 8,003,312 B2 | 8/2011 | Krutzik et al. |
| 8,008,018 B2 | 8/2011 | Quake et al. |
| 8,053,192 B2 | 11/2011 | Bignell et al. |
| 8,067,159 B2 | 11/2011 | Brown et al. |
| 8,101,346 B2 | 1/2012 | Takahama |
| 8,124,404 B2 | 2/2012 | Alphey |
| 8,133,719 B2 | 3/2012 | Drmanac et al. |
| 8,137,563 B2 | 3/2012 | Ma et al. |
| 8,168,385 B2 | 5/2012 | Brenner |
| 8,252,539 B2 | 8/2012 | Quake et al. |
| 8,268,564 B2 | 9/2012 | Roth et al. |
| 8,273,573 B2 | 9/2012 | Ismagilov et al. |
| 8,278,071 B2 | 10/2012 | Brown et al. |
| 8,298,767 B2 | 10/2012 | Brenner et al. |
| 8,304,193 B2 | 11/2012 | Ismagilov et al. |
| 8,318,433 B2 | 11/2012 | Brenner |
| 8,318,460 B2 | 11/2012 | Cantor et al. |
| 8,329,407 B2 | 12/2012 | Ismagilov et al. |
| 8,337,778 B2 | 12/2012 | Stone et al. |
| 8,361,299 B2 | 1/2013 | Sabin et al. |
| 8,420,386 B2 | 4/2013 | Ivics et al. |
| 8,461,129 B2 | 6/2013 | Bolduc et al. |
| 8,563,274 B2 | 10/2013 | Brenner et al. |
| 8,592,150 B2 | 11/2013 | Drmanac et al. |
| 8,598,328 B2 | 12/2013 | Koga et al. |
| 8,603,749 B2 | 12/2013 | Gillevet |
| 8,679,756 B1 | 3/2014 | Brenner et al. |
| 8,748,094 B2 | 6/2014 | Weitz et al. |
| 8,748,102 B2 | 6/2014 | Berka et al. |
| 8,765,380 B2 | 7/2014 | Berka et al. |
| 8,822,148 B2 | 9/2014 | Ismagliov et al. |
| 8,829,171 B2 | 9/2014 | Steemers et al. |
| 8,835,358 B2 | 9/2014 | Fodor et al. |
| 8,871,444 B2 | 10/2014 | Griffiths et al. |
| 8,889,083 B2 | 11/2014 | Ismagilov et al. |
| 8,927,218 B2 | 1/2015 | Forsyth |
| 8,975,302 B2 | 3/2015 | Light et al. |
| 8,986,286 B2 | 3/2015 | Tanghoej et al. |
| 9,005,935 B2 | 4/2015 | Belyaev |
| 9,012,390 B2 | 4/2015 | Holtze et al. |
| 9,017,948 B2 | 4/2015 | Agresti et al. |
| 9,029,083 B2 | 5/2015 | Griffiths et al. |
| 9,029,085 B2 | 5/2015 | Agresti et al. |
| 9,068,210 B2 | 6/2015 | Agresti et al. |
| 9,074,251 B2 | 7/2015 | Steemers et al. |
| 9,080,211 B2 | 7/2015 | Grunenwald et al. |
| 9,089,844 B2 | 7/2015 | Hiddessen et al. |
| 9,102,980 B2 | 8/2015 | Brenner et al. |
| 9,126,160 B2 | 9/2015 | Ness et al. |
| 9,133,009 B2 | 9/2015 | Baroud et al. |
| 9,150,916 B2 | 10/2015 | Christen et al. |
| 9,175,295 B2 | 11/2015 | Kaminaka et al. |
| 9,238,671 B2 | 1/2016 | Goryshin et al. |
| 9,249,460 B2 | 2/2016 | Pushkarev et al. |
| 9,273,349 B2 | 3/2016 | Nguyen et al. |
| 9,290,808 B2 | 3/2016 | Fodor et al. |
| 9,328,382 B2 | 5/2016 | Drmanac et al. |
| 9,347,059 B2 | 5/2016 | Saxonov |
| 9,388,465 B2 | 7/2016 | Hindson et al. |
| 9,410,201 B2 | 8/2016 | Hindson et al. |
| 9,500,664 B2 | 11/2016 | Ness et al. |
| 9,567,631 B2 | 2/2017 | Hindson et al. |
| 9,574,226 B2 | 2/2017 | Gormley et al. |
| 9,636,682 B2 | 5/2017 | Hiddessen et al. |
| 9,637,799 B2 | 5/2017 | Fan et al. |
| 9,644,204 B2 | 5/2017 | Hindson et al. |
| 9,649,635 B2 | 5/2017 | Hiddessen et al. |
| 9,689,024 B2 | 6/2017 | Hindson et al. |
| 9,694,361 B2 | 7/2017 | Bharadwaj et al. |
| 9,695,468 B2 | 7/2017 | Hindson et al. |
| 9,701,998 B2 | 7/2017 | Hindson et al. |
| 9,856,530 B2 | 1/2018 | Hindson et al. |
| 9,951,386 B2 | 4/2018 | Hindson et al. |
| 9,957,558 B2 | 5/2018 | Leamon et al. |
| 9,975,122 B2 | 5/2018 | Masquelier et al. |
| 10,011,872 B1 | 7/2018 | Belgrader et al. |
| 10,030,267 B2 | 7/2018 | Hindson et al. |
| 10,041,116 B2 | 8/2018 | Hindson et al. |
| 10,053,723 B2 | 8/2018 | Hindson et al. |
| 10,059,989 B2 | 8/2018 | Giresi et al. |
| 10,071,377 B2 | 9/2018 | Bharadwaj et al. |
| 10,137,449 B2 | 11/2018 | Bharadwaj et al. |
| 10,150,117 B2 | 12/2018 | Bharadwaj et al. |
| 10,221,442 B2 | 3/2019 | Hindson et al. |
| 10,245,587 B2 | 4/2019 | Masquelier et al. |
| 11,084,036 B2 | 8/2021 | Bharadwaj et al. |
| 2001/0020588 A1 | 9/2001 | Adourian et al. |
| 2001/0036669 A1 | 11/2001 | Jedrzejewski et al. |
| 2001/0041357 A1 | 11/2001 | Fouillet et al. |
| 2001/0044109 A1 | 11/2001 | Mandecki |
| 2001/0048900 A1 | 12/2001 | Bardell et al. |
| 2001/0052460 A1 | 12/2001 | Chien et al. |
| 2001/0053519 A1 | 12/2001 | Fodor et al. |
| 2002/0001856 A1 | 1/2002 | Chow et al. |
| 2002/0003001 A1 | 1/2002 | Weigl et al. |
| 2002/0005354 A1 | 1/2002 | Spence et al. |
| 2002/0034737 A1 | 3/2002 | Drmanac |
| 2002/0043463 A1 | 4/2002 | Shenderov |
| 2002/0051971 A1 | 5/2002 | Stuelpnagel et al. |
| 2002/0051992 A1 | 5/2002 | Bridgham et al. |
| 2002/0058332 A1 | 5/2002 | Quake et al. |
| 2002/0065609 A1 | 5/2002 | Ashby |
| 2002/0068278 A1 | 6/2002 | Giese et al. |
| 2002/0089100 A1 | 7/2002 | Kawasaki |
| 2002/0092767 A1 | 7/2002 | Bjornson et al. |
| 2002/0113009 A1 | 8/2002 | O'Connor et al. |
| 2002/0119455 A1 | 8/2002 | Chan |
| 2002/0119536 A1 | 8/2002 | Stern |
| 2002/0131147 A1 | 9/2002 | Paolini et al. |
| 2002/0160518 A1 | 10/2002 | Hayenga et al. |
| 2002/0164820 A1 | 11/2002 | Brown |
| 2002/0166582 A1 | 11/2002 | O'Connor et al. |
| 2002/0172965 A1 | 11/2002 | Kamb et al. |
| 2002/0175079 A1 | 11/2002 | Christel et al. |
| 2002/0179849 A1 | 12/2002 | Maher et al. |
| 2002/0182118 A1 | 12/2002 | Perry |
| 2003/0005967 A1 | 1/2003 | Karp |
| 2003/0007898 A1 | 1/2003 | Bohm et al. |
| 2003/0008285 A1 | 1/2003 | Fischer |
| 2003/0008323 A1 | 1/2003 | Ravkin et al. |
| 2003/0022231 A1 | 1/2003 | Wangh et al. |
| 2003/0027203 A1 | 2/2003 | Fields |
| 2003/0027214 A1 | 2/2003 | Kamb |
| 2003/0027221 A1 | 2/2003 | Scott et al. |
| 2003/0028981 A1 | 2/2003 | Chandler et al. |
| 2003/0032141 A1 | 2/2003 | Nguyen et al. |
| 2003/0036206 A1 | 2/2003 | Chien et al. |
| 2003/0039978 A1 | 2/2003 | Hannah |
| 2003/0044777 A1 | 3/2003 | Beattie |
| 2003/0044836 A1 | 3/2003 | Levine et al. |
| 2003/0075446 A1 | 4/2003 | Culbertson et al. |
| 2003/0082587 A1 | 5/2003 | Seul et al. |
| 2003/0089605 A1 | 5/2003 | Timperman |
| 2003/0104466 A1 | 6/2003 | Knapp et al. |
| 2003/0108897 A1 | 6/2003 | Drmanac |
| 2003/0124509 A1 | 7/2003 | Kenis et al. |
| 2003/0149307 A1 | 8/2003 | Hai et al. |
| 2003/0170698 A1 | 9/2003 | Gascoyne et al. |
| 2003/0182068 A1 | 9/2003 | Battersby et al. |
| 2003/0207260 A1 | 11/2003 | Trnovsky et al. |
| 2003/0215862 A1 | 11/2003 | Parce et al. |
| 2004/0021068 A1 | 2/2004 | Staats |
| 2004/0040851 A1 | 3/2004 | Karger et al. |
| 2004/0063138 A1 | 4/2004 | McGinnis et al. |
| 2004/0081962 A1 | 4/2004 | Chen et al. |
| 2004/0101680 A1 | 5/2004 | Barber |
| 2004/0101880 A1 | 5/2004 | Rozwadowski et al. |
| 2004/0132122 A1 | 7/2004 | Banerjee et al. |
| 2004/0195728 A1 | 10/2004 | Slomski et al. |
| 2004/0214175 A9 | 10/2004 | McKernan et al. |
| 2004/0224331 A1 | 11/2004 | Cantor et al. |

(56) References Cited

U.S. PATENT DOCUMENTS

| | | |
|---|---|---|
| 2004/0228770 A1 | 11/2004 | Gandhi et al. |
| 2004/0258701 A1 | 12/2004 | Dominowski et al. |
| 2005/0019839 A1 | 1/2005 | Jespersen et al. |
| 2005/0042625 A1 | 2/2005 | Schmidt et al. |
| 2005/0079510 A1 | 4/2005 | Berka et al. |
| 2005/0130188 A1 | 6/2005 | Walt et al. |
| 2005/0172476 A1 | 8/2005 | Stone et al. |
| 2005/0181379 A1 | 8/2005 | Su et al. |
| 2005/0202429 A1 | 9/2005 | Trau et al. |
| 2005/0202489 A1 | 9/2005 | Cho et al. |
| 2005/0221339 A1 | 10/2005 | Griffiths et al. |
| 2005/0244850 A1 | 11/2005 | Huang et al. |
| 2005/0266582 A1 | 12/2005 | Modlin et al. |
| 2005/0272159 A1 | 12/2005 | Ismagilov et al. |
| 2005/0287572 A1 | 12/2005 | Mathies et al. |
| 2006/0002890 A1 | 1/2006 | Hersel et al. |
| 2006/0008799 A1 | 1/2006 | Cai et al. |
| 2006/0020371 A1 | 1/2006 | Ham et al. |
| 2006/0040382 A1 | 2/2006 | Heffron et al. |
| 2006/0073487 A1 | 4/2006 | Oliver et al. |
| 2006/0078888 A1 | 4/2006 | Griffiths et al. |
| 2006/0094108 A1 | 5/2006 | Yoder et al. |
| 2006/0153924 A1 | 7/2006 | Griffiths et al. |
| 2006/0163070 A1 | 7/2006 | Boronkay et al. |
| 2006/0163385 A1 | 7/2006 | Link et al. |
| 2006/0177832 A1 | 8/2006 | Brenner |
| 2006/0177833 A1 | 8/2006 | Brenner |
| 2006/0199193 A1 | 9/2006 | Koo et al. |
| 2006/0240506 A1 | 10/2006 | Kushmaro et al. |
| 2006/0257893 A1 | 11/2006 | Takahashi et al. |
| 2006/0263888 A1 | 11/2006 | Fritz et al. |
| 2006/0275782 A1 | 12/2006 | Gunderson et al. |
| 2006/0286570 A1 | 12/2006 | Rowlen et al. |
| 2006/0292583 A1 | 12/2006 | Schneider et al. |
| 2007/0003442 A1 | 1/2007 | Link et al. |
| 2007/0020617 A1 | 1/2007 | Trnovsky et al. |
| 2007/0020640 A1 | 1/2007 | McCloskey et al. |
| 2007/0031829 A1 | 2/2007 | Yasuno et al. |
| 2007/0039866 A1 | 2/2007 | Schroeder et al. |
| 2007/0042400 A1 | 2/2007 | Choi et al. |
| 2007/0042419 A1 | 2/2007 | Barany et al. |
| 2007/0054119 A1 | 3/2007 | Garstecki et al. |
| 2007/0072208 A1 | 3/2007 | Drmanac |
| 2007/0077572 A1 | 4/2007 | Tawfik et al. |
| 2007/0092914 A1 | 4/2007 | Griffiths et al. |
| 2007/0099208 A1 | 5/2007 | Drmanac et al. |
| 2007/0134277 A1 | 6/2007 | Chen et al. |
| 2007/0154903 A1 | 7/2007 | Marla et al. |
| 2007/0160503 A1 | 7/2007 | Sethu et al. |
| 2007/0172873 A1 | 7/2007 | Brenner et al. |
| 2007/0190543 A1 | 8/2007 | Livak |
| 2007/0195127 A1 | 8/2007 | Ahn et al. |
| 2007/0207060 A1 | 9/2007 | Zou et al. |
| 2007/0228588 A1 | 10/2007 | Noritomi et al. |
| 2007/0231823 A1 | 10/2007 | McKernan et al. |
| 2007/0238113 A1 | 10/2007 | Kanda et al. |
| 2007/0242111 A1 | 10/2007 | Pamula et al. |
| 2007/0259357 A1 | 11/2007 | Brenner |
| 2007/0264320 A1 | 11/2007 | Lee et al. |
| 2008/0003142 A1 | 1/2008 | Link et al. |
| 2008/0004436 A1 | 1/2008 | Tawfik et al. |
| 2008/0014589 A1 | 1/2008 | Link et al. |
| 2008/0056948 A1 | 3/2008 | Dale et al. |
| 2008/0124726 A1 | 5/2008 | Monforte |
| 2008/0138878 A1 | 6/2008 | Kubu et al. |
| 2008/0166720 A1 | 7/2008 | Hsieh et al. |
| 2008/0213766 A1 | 9/2008 | Brown et al. |
| 2008/0228268 A1 | 9/2008 | Shannon et al. |
| 2008/0230386 A1 | 9/2008 | Srinivasan et al. |
| 2008/0241820 A1 | 10/2008 | Krutzik et al. |
| 2008/0242560 A1 | 10/2008 | Gunderson et al. |
| 2008/0268450 A1 | 10/2008 | Nam et al. |
| 2009/0005252 A1 | 1/2009 | Drmanac et al. |
| 2009/0011943 A1 | 1/2009 | Drmanac et al. |
| 2009/0012187 A1 | 1/2009 | Chu et al. |
| 2009/0025277 A1 | 1/2009 | Takanashi |
| 2009/0035770 A1 | 2/2009 | Mathies et al. |
| 2009/0047713 A1 | 2/2009 | Handique |
| 2009/0048124 A1 | 2/2009 | Leamon et al. |
| 2009/0053169 A1 | 2/2009 | Castillo et al. |
| 2009/0068170 A1 | 3/2009 | Weitz et al. |
| 2009/0098555 A1 | 4/2009 | Roth et al. |
| 2009/0099041 A1 | 4/2009 | Church et al. |
| 2009/0105959 A1 | 4/2009 | Braverman et al. |
| 2009/0118488 A1 | 5/2009 | Drmanac et al. |
| 2009/0134027 A1 | 5/2009 | Jary |
| 2009/0137404 A1 | 5/2009 | Drmanac et al. |
| 2009/0137414 A1 | 5/2009 | Drmanac et al. |
| 2009/0143244 A1 | 6/2009 | Bridgham et al. |
| 2009/0148961 A1 | 6/2009 | Luchini et al. |
| 2009/0155780 A1 | 6/2009 | Xiao et al. |
| 2009/0155781 A1 | 6/2009 | Drmanac et al. |
| 2009/0197248 A1 | 8/2009 | Griffiths et al. |
| 2009/0197772 A1 | 8/2009 | Griffiths et al. |
| 2009/0202984 A1 | 8/2009 | Cantor |
| 2009/0203531 A1 | 8/2009 | Kurn |
| 2009/0208548 A1 | 8/2009 | Mason et al. |
| 2009/0264299 A1 | 10/2009 | Drmanac et al. |
| 2009/0269248 A1 | 10/2009 | Falb et al. |
| 2009/0286687 A1 | 11/2009 | Dressman et al. |
| 2009/0311713 A1 | 12/2009 | Pollack et al. |
| 2009/0320930 A1 | 12/2009 | Zeng et al. |
| 2010/0021973 A1 | 1/2010 | Makarov et al. |
| 2010/0021984 A1 | 1/2010 | Edd et al. |
| 2010/0022414 A1 | 1/2010 | Link et al. |
| 2010/0029014 A1 | 2/2010 | Wang |
| 2010/0035254 A1 | 2/2010 | Williams |
| 2010/0062494 A1 | 3/2010 | Church et al. |
| 2010/0069263 A1 | 3/2010 | Shendure et al. |
| 2010/0086914 A1 | 4/2010 | Bentley et al. |
| 2010/0105112 A1 | 4/2010 | Holtze et al. |
| 2010/0113296 A1 | 5/2010 | Myerson |
| 2010/0120098 A1 | 5/2010 | Grunenwald et al. |
| 2010/0130369 A1 | 5/2010 | Shenderov et al. |
| 2010/0136544 A1 | 6/2010 | Agresti et al. |
| 2010/0137163 A1 | 6/2010 | Link et al. |
| 2010/0173394 A1 | 7/2010 | Colston, Jr. et al. |
| 2010/0184928 A1 | 7/2010 | Kumacheva |
| 2010/0187705 A1 | 7/2010 | Lee et al. |
| 2010/0210479 A1 | 8/2010 | Griffiths et al. |
| 2010/0248237 A1 | 9/2010 | Froehlich et al. |
| 2010/0248991 A1 | 9/2010 | Roesler et al. |
| 2010/0304982 A1 | 12/2010 | Hinz et al. |
| 2011/0000560 A1 | 1/2011 | Miller et al. |
| 2011/0008775 A1 | 1/2011 | Gao et al. |
| 2011/0028412 A1 | 2/2011 | Cappello et al. |
| 2011/0033548 A1 | 2/2011 | Lai et al. |
| 2011/0033854 A1 | 2/2011 | Drmanac et al. |
| 2011/0046243 A1 | 2/2011 | Ito et al. |
| 2011/0053798 A1 | 3/2011 | Hindson et al. |
| 2011/0059556 A1 | 3/2011 | Strey et al. |
| 2011/0071053 A1 | 3/2011 | Drmanac et al. |
| 2011/0086780 A1 | 4/2011 | Colston, Jr. et al. |
| 2011/0092376 A1 | 4/2011 | Colston, Jr. et al. |
| 2011/0092392 A1 | 4/2011 | Colston, Jr. et al. |
| 2011/0118139 A1* | 5/2011 | Mehta .......... C12Q 1/6869 506/7 |
| 2011/0160078 A1 | 6/2011 | Fodor et al. |
| 2011/0195496 A1 | 8/2011 | Muraguchi et al. |
| 2011/0201526 A1 | 8/2011 | Berka et al. |
| 2011/0217736 A1 | 9/2011 | Hindson |
| 2011/0218123 A1 | 9/2011 | Weitz et al. |
| 2011/0263457 A1 | 10/2011 | Krutzik et al. |
| 2011/0267457 A1 | 11/2011 | Weitz et al. |
| 2011/0281736 A1 | 11/2011 | Drmanac et al. |
| 2011/0281738 A1 | 11/2011 | Drmanac et al. |
| 2011/0287435 A1 | 11/2011 | Grunenwald et al. |
| 2011/0305761 A1 | 12/2011 | Shum et al. |
| 2011/0306141 A1 | 12/2011 | Bronchetti et al. |
| 2011/0319281 A1 | 12/2011 | Drmanac |
| 2012/0000777 A1 | 1/2012 | Garrell et al. |
| 2012/0003657 A1 | 1/2012 | Myllykangas et al. |
| 2012/0010098 A1 | 1/2012 | Griffiths et al. |
| 2012/0010107 A1 | 1/2012 | Griffiths et al. |

(56) References Cited

U.S. PATENT DOCUMENTS

| | | |
|---|---|---|
| 2012/0014977 A1 | 1/2012 | Furihata et al. |
| 2012/0015382 A1 | 1/2012 | Weitz et al. |
| 2012/0015822 A1 | 1/2012 | Weitz et al. |
| 2012/0071331 A1 | 3/2012 | Casbon et al. |
| 2012/0121481 A1 | 5/2012 | Romanowsky et al. |
| 2012/0132288 A1 | 5/2012 | Weitz et al. |
| 2012/0135893 A1 | 5/2012 | Drmanac et al. |
| 2012/0165219 A1 | 6/2012 | Van Der Zaag et al. |
| 2012/0172259 A1 | 7/2012 | Rigatti et al. |
| 2012/0190032 A1 | 7/2012 | Ness et al. |
| 2012/0190037 A1 | 7/2012 | Durin et al. |
| 2012/0196288 A1 | 8/2012 | Beer |
| 2012/0208705 A1 | 8/2012 | Steemers et al. |
| 2012/0208724 A1 | 8/2012 | Steemers et al. |
| 2012/0211084 A1 | 8/2012 | Weitz et al. |
| 2012/0220494 A1 | 8/2012 | Samuels et al. |
| 2012/0220497 A1 | 8/2012 | Jacobson et al. |
| 2012/0222748 A1 | 9/2012 | Weitz et al. |
| 2012/0231972 A1 | 9/2012 | Golyshin et al. |
| 2012/0252012 A1 | 10/2012 | Armougom et al. |
| 2012/0253689 A1 | 10/2012 | Rogan |
| 2012/0297493 A1 | 11/2012 | Cooper et al. |
| 2012/0309002 A1 | 12/2012 | Link |
| 2012/0316074 A1 | 12/2012 | Saxonov |
| 2012/0328488 A1 | 12/2012 | Puntambekar et al. |
| 2013/0017978 A1 | 1/2013 | Kavanagh et al. |
| 2013/0018970 A1 | 1/2013 | Woundy et al. |
| 2013/0022682 A1 | 1/2013 | Lee et al. |
| 2013/0028812 A1 | 1/2013 | Prieto et al. |
| 2013/0041004 A1 | 2/2013 | Drager et al. |
| 2013/0046030 A1 | 2/2013 | Rotem et al. |
| 2013/0059310 A1 | 3/2013 | Brenner et al. |
| 2013/0078638 A1 | 3/2013 | Berka et al. |
| 2013/0079231 A1 | 3/2013 | Pushkarev et al. |
| 2013/0084243 A1 | 4/2013 | Goetsch et al. |
| 2013/0096073 A1 | 4/2013 | Sidelman |
| 2013/0109575 A1 | 5/2013 | Kleinschmidt et al. |
| 2013/0109576 A1 | 5/2013 | Shuber et al. |
| 2013/0121893 A1 | 5/2013 | Delamarche et al. |
| 2013/0130919 A1 | 5/2013 | Chen et al. |
| 2013/0157870 A1 | 6/2013 | Pushkarev et al. |
| 2013/0157899 A1 | 6/2013 | Adler, Jr. et al. |
| 2013/0178368 A1 | 7/2013 | Griffiths et al. |
| 2013/0189700 A1 | 7/2013 | So et al. |
| 2013/0203605 A1 | 8/2013 | Shendure et al. |
| 2013/0203675 A1 | 8/2013 | DeSimone et al. |
| 2013/0210639 A1 | 8/2013 | Link et al. |
| 2013/0210991 A1 | 8/2013 | Fonnum et al. |
| 2013/0211055 A1 | 8/2013 | Raines et al. |
| 2013/0225418 A1 | 8/2013 | Watson |
| 2013/0225623 A1 | 8/2013 | Buxbaum et al. |
| 2013/0274117 A1 | 10/2013 | Church et al. |
| 2013/0293246 A1 | 11/2013 | Pollack et al. |
| 2013/0296173 A1 | 11/2013 | Callow et al. |
| 2013/0343317 A1 | 12/2013 | Etemad et al. |
| 2014/0024023 A1 | 1/2014 | Cauley, III et al. |
| 2014/0030350 A1 | 1/2014 | Ashrafi et al. |
| 2014/0037514 A1 | 2/2014 | Stone et al. |
| 2014/0038178 A1 | 2/2014 | Otto et al. |
| 2014/0057799 A1 | 2/2014 | Johnson et al. |
| 2014/0065234 A1 | 3/2014 | Shum et al. |
| 2014/0093916 A1 | 4/2014 | Belyaev |
| 2014/0120529 A1 | 5/2014 | Andersen et al. |
| 2014/0155274 A1 | 6/2014 | Xie et al. |
| 2014/0155295 A1 | 6/2014 | Hindson et al. |
| 2014/0194323 A1 | 7/2014 | Gillevet |
| 2014/0199730 A1 | 7/2014 | Agresti et al. |
| 2014/0199731 A1 | 7/2014 | Agresti et al. |
| 2014/0206554 A1 | 7/2014 | Hindson et al. |
| 2014/0227684 A1 | 8/2014 | Hindson et al. |
| 2014/0227706 A1 | 8/2014 | Kato et al. |
| 2014/0228255 A1 | 8/2014 | Hindson et al. |
| 2014/0235506 A1 | 8/2014 | Hindson et al. |
| 2014/0242664 A1 | 8/2014 | Zhang et al. |
| 2014/0274740 A1 | 9/2014 | Srinivasan et al. |
| 2014/0287963 A1 | 9/2014 | Hindson et al. |
| 2014/0302503 A1 | 10/2014 | Lowe et al. |
| 2014/0315725 A1 | 10/2014 | Faham et al. |
| 2014/0315755 A1 | 10/2014 | Chen et al. |
| 2014/0357500 A1 | 12/2014 | Vigneault et al. |
| 2014/0378322 A1 | 12/2014 | Hindson et al. |
| 2014/0378345 A1 | 12/2014 | Hindson et al. |
| 2014/0378349 A1 | 12/2014 | Hindson et al. |
| 2014/0378350 A1 | 12/2014 | Hindson et al. |
| 2015/0005188 A1 | 1/2015 | Levner et al. |
| 2015/0005199 A1 | 1/2015 | Hindson et al. |
| 2015/0005200 A1 | 1/2015 | Hindson et al. |
| 2015/0011430 A1 | 1/2015 | Saxonov |
| 2015/0011432 A1 | 1/2015 | Saxonov |
| 2015/0057163 A1 | 2/2015 | Rotem et al. |
| 2015/0072899 A1 | 3/2015 | Ward et al. |
| 2015/0111256 A1 | 4/2015 | Church et al. |
| 2015/0111788 A1 | 4/2015 | Fernandez et al. |
| 2015/0119280 A1 | 4/2015 | Srinivas et al. |
| 2015/0184127 A1* | 7/2015 | White ............... B01L 3/502707 435/325 |
| 2015/0218633 A1 | 8/2015 | Hindson et al. |
| 2015/0224466 A1 | 8/2015 | Hindson et al. |
| 2015/0225777 A1 | 8/2015 | Hindson et al. |
| 2015/0258543 A1 | 9/2015 | Baroud et al. |
| 2015/0259736 A1 | 9/2015 | Steemers et al. |
| 2015/0267191 A1 | 9/2015 | Steelman et al. |
| 2015/0267246 A1 | 9/2015 | Baroud et al. |
| 2015/0291942 A1 | 10/2015 | Gloeckner et al. |
| 2015/0298091 A1 | 10/2015 | Weitz et al. |
| 2015/0299772 A1 | 10/2015 | Zhang |
| 2015/0299784 A1 | 10/2015 | Fan et al. |
| 2015/0329891 A1 | 11/2015 | Tan et al. |
| 2015/0337298 A1 | 11/2015 | Xi et al. |
| 2015/0353999 A1 | 12/2015 | Agresti et al. |
| 2015/0361418 A1 | 12/2015 | Reed |
| 2015/0368638 A1 | 12/2015 | Steemers et al. |
| 2015/0376605 A1 | 12/2015 | Jarosz et al. |
| 2015/0376608 A1 | 12/2015 | Kaper et al. |
| 2015/0376609 A1 | 12/2015 | Hindson et al. |
| 2015/0376700 A1 | 12/2015 | Schnall-Levin et al. |
| 2015/0379196 A1 | 12/2015 | Schnall-Levin et al. |
| 2016/0024558 A1 | 1/2016 | Hardenbol et al. |
| 2016/0032282 A1 | 2/2016 | Vigneault et al. |
| 2016/0053253 A1 | 2/2016 | Salathia et al. |
| 2016/0060621 A1 | 3/2016 | Agresti et al. |
| 2016/0115474 A1 | 4/2016 | Jelinek et al. |
| 2016/0122753 A1 | 5/2016 | Mikkelsen et al. |
| 2016/0122817 A1 | 5/2016 | Jarosz et al. |
| 2016/0123858 A1 | 5/2016 | Kapur et al. |
| 2016/0153005 A1 | 6/2016 | Zhang et al. |
| 2016/0160235 A1 | 6/2016 | Solodushko et al. |
| 2016/0177359 A1 | 6/2016 | Ukanis et al. |
| 2016/0208323 A1 | 7/2016 | Bernstein et al. |
| 2016/0231324 A1 | 8/2016 | Zhao et al. |
| 2016/0244742 A1 | 8/2016 | Linnarsson et al. |
| 2016/0244809 A1 | 8/2016 | Belgrader et al. |
| 2016/0244825 A1 | 8/2016 | Vigneault et al. |
| 2016/0257984 A1 | 9/2016 | Hardenbol et al. |
| 2016/0281160 A1 | 9/2016 | Jarosz et al. |
| 2016/0304860 A1 | 10/2016 | Hindson et al. |
| 2016/0326583 A1 | 11/2016 | Johnson et al. |
| 2016/0348093 A1 | 12/2016 | Price et al. |
| 2016/0376663 A1 | 12/2016 | Brown |
| 2017/0009274 A1 | 1/2017 | Abate et al. |
| 2017/0016041 A1 | 1/2017 | Greenfield et al. |
| 2017/0114390 A1 | 4/2017 | Hindson et al. |
| 2017/0145476 A1 | 5/2017 | Ryvkin et al. |
| 2017/0183701 A1 | 6/2017 | Agresti et al. |
| 2017/0247757 A1 | 8/2017 | Hindson et al. |
| 2017/0260584 A1 | 9/2017 | Zheng et al. |
| 2017/0268056 A1 | 9/2017 | Vigneault et al. |
| 2017/0321252 A1 | 11/2017 | Hindson et al. |
| 2017/0348691 A1 | 12/2017 | Bharadwaj et al. |
| 2017/0356027 A1 | 12/2017 | Hindson et al. |
| 2018/0008984 A1 | 1/2018 | Bharadwaj et al. |
| 2018/0015472 A1 | 1/2018 | Bharadwaj et al. |
| 2018/0015473 A1 | 1/2018 | Bharadwaj et al. |
| 2018/0016634 A1 | 1/2018 | Hindson et al. |

(56) References Cited

U.S. PATENT DOCUMENTS

| | | |
|---|---|---|
| 2018/0030512 A1 | 2/2018 | Hindson et al. |
| 2018/0030515 A1 | 2/2018 | Regev et al. |
| 2018/0051321 A1 | 2/2018 | Hindson et al. |
| 2018/0057868 A1 | 3/2018 | Walder et al. |
| 2018/0087050 A1 | 3/2018 | Zheng et al. |
| 2018/0094298 A1 | 4/2018 | Hindson et al. |
| 2018/0094313 A1 | 4/2018 | Hindson et al. |
| 2018/0094315 A1 | 4/2018 | Hindson et al. |
| 2018/0105808 A1 | 4/2018 | Mikkelsen et al. |
| 2018/0112253 A1 | 4/2018 | Hindson et al. |
| 2018/0112266 A1 | 4/2018 | Hindson et al. |
| 2018/0179580 A1 | 6/2018 | Hindson et al. |
| 2018/0195112 A1 | 7/2018 | Lebofsky et al. |
| 2018/0216162 A1 | 8/2018 | Belhocine et al. |
| 2018/0236443 A1 | 8/2018 | Masquelier et al. |
| 2018/0258466 A1 | 9/2018 | Hindson et al. |
| 2018/0258482 A1 | 9/2018 | Hindson et al. |
| 2018/0265928 A1 | 9/2018 | Schnall-Levin et al. |
| 2018/0273933 A1 | 9/2018 | Gunderson et al. |
| 2018/0274027 A1 | 9/2018 | Hindson et al. |
| 2018/0282804 A1 | 10/2018 | Hindson et al. |
| 2018/0327839 A1 | 11/2018 | Hindson et al. |
| 2018/0340939 A1 | 11/2018 | Gaublomme et al. |
| 2019/0134629 A1 | 5/2019 | Bernate et al. |

FOREIGN PATENT DOCUMENTS

| | | | |
|---|---|---|---|
| EP | 0249007 | A2 | 12/1987 |
| EP | 0271281 | A2 | 6/1988 |
| EP | 0637996 | B1 | 7/1997 |
| EP | 1019496 | B1 | 9/2004 |
| EP | 1672064 | A1 | 6/2006 |
| EP | 1482036 | B1 | 10/2007 |
| EP | 1841879 | A2 | 10/2007 |
| EP | 1594980 | B1 | 11/2009 |
| EP | 1967592 | B1 | 4/2010 |
| EP | 2258846 | A2 | 12/2010 |
| EP | 2145955 | B1 | 2/2012 |
| EP | 1905828 | B1 | 8/2012 |
| EP | 2136786 | B1 | 10/2012 |
| EP | 1908832 | B1 | 12/2012 |
| EP | 2540389 | A1 | 1/2013 |
| EP | 2635679 | A1 | 9/2013 |
| EP | 2752664 | A1 | 7/2014 |
| GB | 2097692 | B | 5/1985 |
| GB | 2485850 | A | 5/2012 |
| JP | S5949832 | A | 3/1984 |
| JP | S60227826 | A | 11/1985 |
| JP | 2006-507921 | A | 3/2006 |
| JP | 2006-289250 | A | 10/2006 |
| JP | 2007-015990 | A | 1/2007 |
| JP | 2007-268350 | A | 10/2007 |
| JP | 2009-513948 | A | 4/2009 |
| JP | 2009-208074 | A | 9/2009 |
| JP | 2012-131798 | A | 7/2012 |
| WO | WO-84/02000 | A1 | 5/1984 |
| WO | WO-94/18218 | A1 | 8/1994 |
| WO | WO-94/19101 | A1 | 9/1994 |
| WO | WO-94/23699 | A1 | 10/1994 |
| WO | WO-95/30782 | A1 | 11/1995 |
| WO | WO-96/29629 | A2 | 9/1996 |
| WO | WO-96/41011 | A1 | 12/1996 |
| WO | WO-98/02237 | A1 | 1/1998 |
| WO | WO-98/52691 | A1 | 11/1998 |
| WO | WO-99/09217 | A1 | 2/1999 |
| WO | WO-99/52708 | A1 | 10/1999 |
| WO | WO-2000/008212 | A1 | 2/2000 |
| WO | WO-00/23181 | A1 | 4/2000 |
| WO | WO-00/26412 | A1 | 5/2000 |
| WO | WO-00/43766 | A1 | 7/2000 |
| WO | WO-00/70095 | A2 | 11/2000 |
| WO | WO-01/02850 | A1 | 1/2001 |
| WO | WO-01/14589 | A2 | 3/2001 |
| WO | WO-01/89787 | A2 | 11/2001 |
| WO | WO-01/90418 | A1 | 11/2001 |
| WO | WO-01/27610 | A3 | 3/2002 |
| WO | WO-02/31203 | A2 | 4/2002 |
| WO | WO-02/086148 | A1 | 10/2002 |
| WO | WO-02/18949 | A3 | 1/2003 |
| WO | WO-03/062462 | A2 | 7/2003 |
| WO | WO-2004/002627 | A2 | 1/2004 |
| WO | WO-2004/010106 | A1 | 1/2004 |
| WO | WO-2004/061083 | A2 | 7/2004 |
| WO | WO-2004/065617 | A2 | 8/2004 |
| WO | WO-2004/069849 | A2 | 8/2004 |
| WO | WO-2004/091763 | A2 | 10/2004 |
| WO | WO-2004/102204 | A1 | 11/2004 |
| WO | WO-2004/103565 | A2 | 12/2004 |
| WO | WO-2004/105734 | A1 | 12/2004 |
| WO | WO-2005/002730 | A1 | 1/2005 |
| WO | WO-2005/021151 | A1 | 3/2005 |
| WO | WO-2005/023331 | A2 | 3/2005 |
| WO | WO-2005/040406 | A1 | 5/2005 |
| WO | WO-2005/049787 | A9 | 6/2005 |
| WO | WO-2005/082098 | A2 | 9/2005 |
| WO | WO-2006/030993 | A1 | 3/2006 |
| WO | WO-2006/078841 | A1 | 7/2006 |
| WO | WO-2006/096571 | A2 | 9/2006 |
| WO | WO-2007/001448 | A2 | 1/2007 |
| WO | WO-2007/002490 | A2 | 1/2007 |
| WO | WO-2007/012638 | A1 | 2/2007 |
| WO | WO-2007/018601 | A1 | 2/2007 |
| WO | WO-2007/024840 | A2 | 3/2007 |
| WO | WO-2007/081387 | A1 | 7/2007 |
| WO | WO-2007/084192 | A2 | 7/2007 |
| WO | WO-2007/089541 | A2 | 8/2007 |
| WO | WO-2007/093819 | A2 | 8/2007 |
| WO | WO-2007/111937 | A1 | 10/2007 |
| WO | WO-2007/114794 | A1 | 10/2007 |
| WO | WO-2007/121489 | A2 | 10/2007 |
| WO | WO-2007/133710 | A2 | 11/2007 |
| WO | WO-2007/138178 | A2 | 12/2007 |
| WO | WO-2007/139766 | A2 | 12/2007 |
| WO | WO-2007/140015 | A2 | 12/2007 |
| WO | WO-2007/147079 | A2 | 12/2007 |
| WO | WO-2007/149432 | A2 | 12/2007 |
| WO | WO-2008/021123 | A1 | 2/2008 |
| WO | WO-2008/091792 | A2 | 7/2008 |
| WO | WO-2008/102057 | A1 | 8/2008 |
| WO | WO-2008/121342 | A2 | 10/2008 |
| WO | WO-2007/081385 | A8 | 11/2008 |
| WO | WO-2008/061193 | A3 | 11/2008 |
| WO | WO-2008/109176 | A8 | 11/2008 |
| WO | WO-2008/134153 | A1 | 11/2008 |
| WO | WO-2008/150432 | A1 | 12/2008 |
| WO | WO-2009/005680 | A1 | 1/2009 |
| WO | WO-2009/011808 | A1 | 1/2009 |
| WO | WO-2009/015296 | A1 | 1/2009 |
| WO | WO-2009/048532 | A2 | 4/2009 |
| WO | WO-2009/061372 | A1 | 5/2009 |
| WO | WO-2009/085215 | A1 | 7/2009 |
| WO | WO-2009/147386 | A1 | 12/2009 |
| WO | WO-2010/004018 | A2 | 1/2010 |
| WO | WO-2010/014604 | A1 | 2/2010 |
| WO | WO-2010/033200 | A2 | 3/2010 |
| WO | WO-2010/048605 | A1 | 4/2010 |
| WO | WO-2010/104426 | A1 | 9/2010 |
| WO | WO-2010/115154 | A1 | 10/2010 |
| WO | WO-2010/148039 | A2 | 12/2010 |
| WO | WO-2010/151776 | A2 | 12/2010 |
| WO | WO-2010/117620 | A3 | 2/2011 |
| WO | WO-2011028539 | A1 | 3/2011 |
| WO | WO-2011/047870 | A1 | 4/2011 |
| WO | WO-2011/056546 | A1 | 5/2011 |
| WO | WO-2011/074960 | A1 | 6/2011 |
| WO | WO-2011/140627 | A1 | 11/2011 |
| WO | WO-2012/012037 | A1 | 1/2012 |
| WO | WO-2012/019765 | A1 | 2/2012 |
| WO | WO-2012/047889 | A2 | 4/2012 |
| WO | WO-2012/048340 | A2 | 4/2012 |
| WO | WO-2012/048341 | A1 | 4/2012 |
| WO | WO-2012/061832 | A1 | 5/2012 |
| WO | WO-2011/066476 | A8 | 8/2012 |
| WO | WO-2012/106546 | A2 | 8/2012 |

(56) References Cited

FOREIGN PATENT DOCUMENTS

| | | |
|---|---|---|
| WO | WO-2012/112804 A1 | 8/2012 |
| WO | WO-2012/112970 A2 | 8/2012 |
| WO | WO-2012/083225 A4 | 9/2012 |
| WO | WO-2012/136734 A1 | 10/2012 |
| WO | WO-2012/142611 A2 | 10/2012 |
| WO | WO-2012/148497 A2 | 11/2012 |
| WO | WO-2012/149042 A2 | 11/2012 |
| WO | WO-2012/166425 A2 | 12/2012 |
| WO | WO-2013/019751 A1 | 2/2013 |
| WO | WO-2013/036929 A1 | 3/2013 |
| WO | WO-2013/055955 A1 | 4/2013 |
| WO | WO-2013/096643 A1 | 6/2013 |
| WO | WO-2013/122996 A1 | 8/2013 |
| WO | WO-2013/123125 A1 | 8/2013 |
| WO | WO-2013/126741 A1 | 8/2013 |
| WO | WO-2013/134261 A1 | 9/2013 |
| WO | WO-2013/150083 A1 | 10/2013 |
| WO | WO-2013/177220 A1 | 11/2013 |
| WO | WO-2013/188872 A1 | 12/2013 |
| WO | WO-2014/028537 A1 | 2/2014 |
| WO | WO-2014/053854 A1 | 4/2014 |
| WO | WO-2014/071361 A1 | 5/2014 |
| WO | WO-2014/074611 A1 | 5/2014 |
| WO | WO-2014/093676 A1 | 6/2014 |
| WO | WO-2014/108810 A2 | 7/2014 |
| WO | WO-2014/140309 A1 | 9/2014 |
| WO | WO-2014/144495 A1 | 9/2014 |
| WO | WO-2014/150931 A1 | 9/2014 |
| WO | WO-2014/182835 A1 | 11/2014 |
| WO | WO-2014/189957 A2 | 11/2014 |
| WO | WO-2014/210353 A2 | 12/2014 |
| WO | WO-2015/031691 A1 | 3/2015 |
| WO | WO-2015/044428 A1 | 4/2015 |
| WO | WO-2015/164212 A1 | 10/2015 |
| WO | WO-2016/040476 A1 | 3/2016 |
| WO | WO-2016/061517 A2 | 4/2016 |
| WO | WO-2016/126871 A2 | 8/2016 |
| WO | WO-2016/170126 A1 | 10/2016 |
| WO | WO-2016/176322 A1 | 11/2016 |
| WO | WO-2016/187717 A1 | 12/2016 |
| WO | WO-2016/191618 A1 | 12/2016 |
| WO | WO-2016/207647 A1 | 12/2016 |
| WO | WO-2016/207653 A1 | 12/2016 |
| WO | WO-2016/207661 A1 | 12/2016 |
| WO | WO-2017/015075 A1 | 1/2017 |
| WO | WO-2017/025594 A1 | 2/2017 |
| WO | WO-2017/053902 A1 | 3/2017 |
| WO | WO-2017/053903 A1 | 3/2017 |
| WO | WO-2017/053905 A1 | 3/2017 |
| WO | WO-2017/075265 A1 | 5/2017 |
| WO | WO-2017/156336 A1 | 9/2017 |
| WO | WO-2018/045186 A1 | 3/2018 |
| WO | WO-2018/119301 A1 | 6/2018 |
| WO | WO-2018/191701 A1 | 10/2018 |
| WO | WO-2019/028166 A1 | 2/2019 |

OTHER PUBLICATIONS

"How many species of bacteria are there" (wisegeek.com; accessed Jan. 21, 2014).
Huebner et al., "Microdroplets: A sea of applications?" Lab on a Chip. 8: 1244-1254 (2008).
Kiss et al., "High-Throughput Quantitative Polymerase Chain Reaction in Picoliter Droplets," Anal Chem. 80(23): 8975-8981 (2008).
"List of sequenced bacterial genomes" (Wikipedia.com; accessed Jan. 24, 2014).
Pascaline et al., "Controlling droplet incubation using close-packed plug flow," Biomicrofluidics. 5: 024101-1-024101-6 (2011).
"Portable Water Filters" (http://www.portablewaterfilters.org/water-filter-guide/particle-contaminant-size-chart-microns/) 2015, accessed Oct. 19, 2017.
"U.S. Appl. No. 61/982,001, filed Apr. 21, 2014 (Year:2014)".
10x Genomics. "10x Genomics Chromium™ Single Cell 3' Solution Utilized for Perturb-seq Approach," Press Release, <https://www.10xgenomics.com/news/10x-genomics-chromium-single-cell-3-solution-utilized-perturb-seq-approach/>, dated Dec. 19, 2016.
Abate et al., "Syringe-vacuum microfluidics: A portable technique to create monodisperse emulsions," Biomicrofluidics. 5(1): 014107 (2011).
Abate et al., "Valve-based flow focusing for drop formation," Appl Phys Lett. 94 (2009) (3 pages).
Abate et al., "Beating Poisson encapsulation statistics using close-packed ordering," Lab Chip. 9(18):2628-31 (2009).
Abate et al., "High-throughput injection with microfluidics using picoinjectors," Proc Natl Acad Sci USA. 107(45):19163-6 (2010).
Adamson et al., "Production of arrays of chemically distinct nanolitre plugs via repeated splitting in microfluidic devices," Lab Chip. 6(9): 1178-1186 (2006).
Adamson et al., "A Multiplexed Single-Cell CRISPR Screening Platform Enables Systematic Dissection of the Unfolded Protein Response," Cell. 167(7):1867-1882.e21 (2016).
Adey et al. "Rapid, low-input, low-bias construction of shotgun fragment libraries by high-density in vitro transposition," Genome Biology. 11:R119 (2010).
Adey et al., "Ultra-low-input, tagmentation-based whole-genome bisulfite sequencing," Genome Research. 22(6): 1139-1143 (2012).
Agresti et al., "Selection of Ribozymes that Catalyse Multiple-Turnover Diels-Alder Cycloadditions by Using in Vitro Compartmentalization," Proc Natl Acad Sci U S A. 102(45):16170-5 (2005).
Agresti et al., "Ultra-high-throughput screening in drop-based microfluidics for directed evolution," Proc Natl Acad Sci USA. 107(9): 4004-9 (2010).
Ahern, "Biochemical, Reagents Kits Offer Scientists Good Return on Investment," The Scientist.9(15):1-7 (1995).
Ahn et al., "Dielectrophoretic manipulation of drops for high-speed microfluidic sorting devices," Applied Physics Letter. 88 (2006).
Aitman et al., "Copy number polymorphism in Fcgr3 predisposes to glomerulonephritis in rats and humans," Nature. 439(7078):851-5 (2006).
Akselband, "Enrichment of slow-growing marine microorganisms from mixed cultures using gel microdrop (GMD) growth assay and fluorescence-activated cell sorting," J Exp Marine Biol. 329: 196-205 (2006).
Akselband, "Rapid mycobacteria drug susceptibility testing using gel microdrop (GMD) growth assay and flow cytometry," J Microbiol Methods. 62: 181-197 (2005).
Ali-Cherif et al., "Programmable Magnetic Tweezers and Droplet Microfluidic Device for High-Throughput Nanoliter Multi-Step Assays," Angew Chem Int Ed. 51: 10765-10769 (2012).
Altemose et al., "Genomic Characterization of Large Heterochromatic Gaps in the Human Genome Assembly," PLOS Computational PLoS Comput Biol. 10(5) (2014) (14 pages).
Amini et al. "Haplotype-resolved whole-genome sequencing by contiguity-preserving transposition and combinatorial indexing" Nat Genet. 46(12):1343-1349 (2014).
Anna et al., "Formation of dispersions using 'flow focusing' in microchannels," Applied Physics Letters. 82(3): 364-366 (2003).
Anonymous, "Oligo(dT)25 cellulose beads" NEB (2012) Retrieved from the Internet:https://www.neb.com/~/media/Catalog/All-Products/286CA51268E24DE1B06F1CB288698B54/Datacards%20or%Manuals/S1408Datasheet-Lot0011205.pdf.
Anonymous, "Oligotex Handbook" Qiagen (2012) XP055314680, Retrieved from the Internet: URL:http://www.qiagen.com/de/resources/download.apsx?id=f9fald98-d54d-47e7-a20b-8b0cb8975009&lang=en.
Anonymous: "TCEP=HCI" Thermo Scientific, Dec. 31, 2013 (Dec. 31, 2013), XP055508461, Retrieved from the Internet: URL:https://assets.thermofisher.com/TFS-Assets/LSG/manuals/MAN0011306_TCEP_HCI_UG.pdf.
Anonymous: "Viscosity-Basic concepts" (2004) XP055314117. Retrieved from the Internet: URL:http://lhtc.epfl.ch/webdav/site/lhtc/shared/import/migration/2_VISCOSITY.pdf.
Ason et al. "DNA sequence bias during Tn5 transposition. Journal of molecular biology" J Mol Biol. 335(5):12-13-25 (2004).
Attia et al., "Micro-injection moulding of polymer microfluidic devices," Microfluidics and Nanofluidics. 7(1):1-28 (2009).

(56) References Cited

OTHER PUBLICATIONS

Balikova et al. "Autosomal-dominant microtia linked to five tandem copies of a copy-number-variable region at chromosome 4p16," Am J Hum Genet. 82(1):181-7 (2008).
Bardin et al., "High-speed, clinical-scale microfluidic generation of stable phase-change droplets for gas embolotherapy," Lab Chip. 11: 3990-3998 (2011).
Baret et al., "Kinetic aspects of emulsion stabilization by surfactants: a microfluidic analysis," Langmuir. 25:6088-6093 (2009).
Baret et al., "Fluorescence-activated droplet sorting (FADS): efficient microfluidic cell sorting based on enzymatic activity," Lab Chip. 9(13):1850-8 (2009).
BD. BD Rhapsody™ Single-Cell Analysis System: Analyze hundreds of genes across tens of thousands of single cells in parallel. BD, Becton, Dickinson and Company. BDGM1012 Rev. 1. 2017. 8 pages.
Becker et al., "Polymer Microfabrication Technologies for Microfluidic," Anal Bioanal Chem. 390(1): 89-111 (2008).
Belder, "Microfluidics with Droplets," Angew Chem Int Ed. 44: 3521-3522 (2005).
Bentzen et al., "Large-scale detection of antigen-specific T cells using peptide-MHC-I multimers labeled with DNA barcodes," Nat Biotechnol. 34(10):1037-1045 (2016).
Berkum et al. "Hi-C: a method to study the three-dimensional architecture of genomes," J Vis Exp. (39):1869 (2010).
Biles et al., "Low-fidelity Pyrococcus furiosis DNA polymerase mutants useful in error-prone PCR," Nucleic Acids Res. 32(22):e176 (2004).
Bilotkach et al., "Fabrication of PDMS Membranes with Aqueous Molds for Microfluidic Systems," 12th Int'l Conference Miniaturized Sys for Chemistry and Life Scis (2008).
Bjornsson et al., "Intra-individual change over time in DNA methylation with familial clustering," JAMA. 299(24):2877-83 (2008).
Bodi et al., "Comparison of Commercially Available Target Enrichment Methods for Next-Generation Sequencing," J Biomol Tech. 24(2): 73-86 (2013).
Boone et al., "Plastic advances microfluidic devices. The devices debuted in silicon and glass, but plastic fabrication may make them hugely successful in biotechnology application," Analytical Chemistry. 78A-86A (2002).
Boulanger et al., "Massively parallel haplotyping on microscopic beads for the high- throughput phase analysis of single molecules," PLoS One.7(4):1-10 (2012).
Boyle et al., "High-resolution genome-wide in vivo footprinting of diverse transcription factors in human cells," Genome Res. 21(3):456-64 (2011).
Braeckmans et al., "Scanning the Code," Modern Drug Discovery. 28-32 (2003).
Bransky et al., "A microfluidic droplet generator based on a piezoelectric actuator," Lab Chip. 9(4):516-20 (2009).
Brenner et al., "In vitro cloning of complex mixtures of DNA on microbeads: physical separation of differentially expressed cDNAs," Proc Natl Acad Sci U S A. 97(4):1665-70 (2000).
Brenner et al., "Injection Molding of Microfluidic Chips by Epoxy-Based Master Tools" (Oct. 9, 2005).
Briggs, et al. "Tumor-infiltrating immune repertoires captures by single-cell barcoding in emulsion" with Supplementary material. bioRxiv 134841; doi: https://doi.org/10.1101/134841. Posted May 5, 2017.
Brody et al., "Biotechnology at Low Reynolds Numbers," Biophys J. 71:3430-3441 (1996).
Brouzes et al., "Droplet microfluidic technology for single-cell high-throughput screening," Proc Natl Acad Sci U S A. 106(34):14195-200 (2009).
Brown, K., Targeted Sequencing Using Droplet-Based Microfluidics, RainDance Technologies, 2009, 1-18.
Browning et al., "Haplotype phasing: existing methods and new developments," Nat Rev Genet. 12(10):703-14 (2011).

Buchman et al., "Selective RNA amplification: a novel method using dUMP-containing primers and uracil DNA glycosylase," PCR Methods Appl. 3(1):28-31 (1993).
Buenrostro et al., "Transposition of native chromatin for fast and sensitive epigenomic profiling of open chromatin, DNA-binding proteins and nucleosome position," Nat Methods. 10(12):1213-8 (2013).
Buenrostro et al., "ATAC-seq: A Method for Assaying Chromatin Accessibility Genome-Wide," Curr Protoc Mol Biol. 109: 21.29.1-21.29.9. (2015).
Buenrostro et al., "Single-cell chromatin accessibility reveals principles of regulatory variation," Nature. 523(7561):486-90 (2015).
Burns et al., "An Integrated Nanoliter DNA Analysis Device," Science. 282(5388):484-7 (1998).
Burns et al., "Microfabricated structures for integrated DNA analysis," Proc Natl Acad Sci U S A. 93(11):5556-5561 (1996).
Burns et al., "The intensification of rapid reactions in multiphase systems using slug flow in capillaries," Lab Chip. 1(1): 10-5 (2001).
Cappuzzo et al., "Increased HER2 gene copy No. is associated with response to gefitinib therapy in epidermal growth factor receptor-positive non-small-cell lung cancer patients," J Clin Oncol. 23(22):5007-18 (2005).
Carroll, "The selection of high-producing cell lines using flow cytometry and cell sorting," Exp Op Biol. Therp. 4(11): 1821-1829 (2004).
Caruccio et al. "Preparation of Next-Generation Sequencing Libraries Using Nextera Technology: Simultaneous DNA Fragmentation and Adaptor Tagging by In Vitro Transposition," Methods Mol Biol. 733:241-55 (2011).
Caruccio, et al., "Nextera Technology for NGS DNA Library Preparation: Simultaneous Fragmentation and Tagging by In Vitro Transposition," Nextera Technology. 16-3: 1-3 (2009).
Casbon et al., "Reflex: intramolecular barcoding of long-range PCR products for sequencing multiple pooled DNAs," Nucleic Acids Res. 41(10) 1-6 (2013).
Chan et al., "High-Temperature Microfluidic Synthesis of CdSe Nanocrystals in Nanoliter Droplets," J Am Soc. 127: 13854-13861 (2005).
Chang et al., "Droplet-based microfluidic platform for heterogeneous enzymatic assays," Lab Chip. 13: 1817-1822 (2013).
Chaudhary, "A rapid method of cloning functional variable-region antibody genes in *Escherichia coli* as single-chain immunotoxins," Proc Natl Acad Sci USA. 87: 1066-1070 (1990).
Chechetkin et al., "Sequencing by hybridization with the generic 6-mer oligonucleotide microarray: an advanced scheme for data processing," J Biomol Struct Dyn. 8(1):83-101 (2000).
Chen et al., "Chemical transfection of cells in picoliter aqueous droplets in fluorocarbon oil," Anal Chem. 83(22): 8816-20 (2011).
Chien et al., "Multiport flow-control system for lab-on-a-chip microfluidic devices," Fresenius J Anal Chem. 371:106-111 (2001).
Choi et al., "Identification of novel isoforms of the EML4-ALK transforming gene in non-small cell lung cancer," Cancer Res. 68(13):4971-6 (2008).
Chokkalingam et al., "Probing cellular heterogeneity in cytokine-secreting immune cells using droplet-based microfluidics," Lab Chip. 13(24):4740-4 (2013).
Chou et al., "Disposable Microdevices for DNA Analysis and Cell Sorting," Proc Solid-State Sensor and Actuator Workshop, Hilton Head, SC, Jun. 8-11, 1998. 11-14.
Christian et al., "Targeting DNA double-strand breaks with TAL effector nucleases," Genetics. 186 (2): 757-61 (2010).
Christiansen et al., "The Covalent Eukaryotic Topoisomerase I-DNA Intermediate Catalyzes pH-dependent Hydrolysis and Alcoholysis," J Biol Chem. 269(15):11367-11373 (1994).
Christopher et al., "Microfluidic methods for generating continuous droplet streams," J Phys D: Appl Phys. 40: R319-R336 (2007).
Chu et al., "Controllable monodisperse multiple emulsions," Angew Chem Int Ed Engl. 46(47): 8970-4 (2007).
Chung et al., "Structural and molecular interrogation of intact biological systems," Nature. 497(7449):332-7 (2013).
Clark et al., "Single-cell epigenomics: powerful new methods for understanding gene regulation and cell identity," Genome Biol. 17:72 (2016).

(56) References Cited

OTHER PUBLICATIONS

Clausell-Tormos et al., "Droplet-based microfluidic platforms for the encapsulation and screening of mammalian cells and multicellular organisms," Chem Biol. 15:427-437 (2008).
Co-pending U.S. Appl. No. 15/440,772, filed Feb. 23, 2017.
Co-pending U.S. Appl. No. 15/449,741, filed Mar. 3, 2017.
Co-pending U.S. Appl. No. 16/033,065, filed Jul. 11, 2018.
Co-pending U.S. Appl. No. 16/044,374, filed Jul. 24, 2018.
Co-pending U.S. Appl. No. 16/107,685, filed Aug. 21, 2018.
Co-pending U.S. Appl. No. 16/170,980, filed Oct. 25, 2018.
Co-pending U.S. Appl. No. 16/180,378, filed Nov. 5, 2018.
Co-pending U.S, Appl. No. 16/274,134, filed Feb. 12, 2019.
Co-pending U.S. Appl. No. 16/419,820, filed May 22, 2019.
Cong et al., "Multiplex genome engineering using CRISPR/Cas systems," Science. 339 (6121) 819-23 (2013).
Cook et al., "Copy-number variations associated with neuropsychiatric conditions," Nature. 455(7215):919-23 (2008).
Coufal et al., "L1 retrotransposition in human neural progenitor cells," Nature. 460(7259):1127-31 (2009).
Curcio, Mario, Thesis: "Improved Techniques for High-Throughput Molecular Diagnostics," Doctor in Philosophy of Chemistry, Royal Institute of Technology, 2002 (131 pages).
Cusanovich et al., "Supplementary materials for Multiplex single-cell profiling of chromatin accessibility by combinatorial cellular indexing," Science. 348(6237):910-4 (2015).
Cusanovich et al., "Multiplex single-cell profiling of chromatin accessibility by combinatorial cellular indexing," Science. (6237): 910-4 (2015).
Damean et al., "Simultaneous measurement of reactions in microdroplets filled by concentration gradients," Lab Chip. 9(12): 1707-13 (2009).
Dangla et al., "Droplet microfluidics driven by gradients of confinement," Proc Natl Acad Sci U S A. 110(3): 853-858 (2013).
De Bruin et al., "UBS Investment Research. Q-Series®: DNA Sequencing," UBS Securities LLC (2007) (15 pages).
Dekker et al., "Capturing chromosome conformation," Science. 295(5558):1306-11 (2002).
Demirci et al., "Single cell epitaxy by acoustic picolitre droplets," Lab Chip. 7(9): 1139-45 (2007).
Dendukuri et al., "Controlled synthesis of nonspherical microparticles Using Microfluidics," Langmuir. 21: 2113-2116 (2005).
Depristo et al., "A framework for variation discovery and genotyping using next-generation DNA sequencing data," Nature Genet. 43(5):491-8 (2011).
Dey et al., "Integrated genome and transcriptome sequencing of the same cell," available in PMC Dec. 18, 2017, published in final edited form as: Nature Biotechnology. 33(3): 285-289 (2015).
Dixit et al., "Perturb-Seq: Dissecting Molecular Circuits with Scalable Single-Cell RNA Profiling of Pooled Genetic Screens," Cell. 167(7):1853-1866.e17 (2016).
Doerr, "The smallest bioreactor," Nature Methods. 2(5): 326 (2005).
Doshi et al., "Red blood cell-mimicking synthetic biomaterial particles," Proc Natl Acad Sci U S A. 106(51):21495-21499 (2009).
Dowding et al., "Oil core/polymer shell microcapsules by internal phase separation from emulsion droplets. II: controlling the release profile of active molecules," Langmuir. 21(12): 5278-84 (2005).
Draper et al., "Compartmentalization of electrophoretically separated analytes in a multiphase microfluidic platform," Anal Chem. 84(13): 5801-8 (2012).
Dressler et al., "Droplet-based microfluidics enabling impact on drug discovery," J Biomol Screen. 19(4): 483-96 (2014).
Dressman et al. Supplementary Information pp. 1-2 of article published 2003, PNAS 100(15:8817-22).
Dressman et al., "Transforming single DNA molecules into fluorescent magnetic particles for detection and enumeration of genetic variations," Proc Natl Acad Sci U S A.100(15):8817-22 (2003).
Drmanac et al., "Sequencing by hybridization (SBH): advantages, achievements, and opportunities," Adv Biochem Eng Biotechnol. 77: 75-101 (2002).
"Droplet Based Sequencing," slides dated Mar. 12, 2008.
Duffy et al., "Rapid Prototyping of Microfluidic Systems in Poly(dimethylsiloxane)," Anal Chem. 70(23):4974-84 (1998).
Eastburn et al., "Ultrahigh-throughput mammalian single-cell reverse-transcriptase polymerase chain reaction in microfluidic droplets," Anal Chem. 85(16): 8016-21 (2013).
Engl et al., "Controlled production of emulsions and particles by milli- and microfluidic techniques," Current Opinion in Colloid and Interface Science. 13: 206-216 (2007).
Epicentre .. "EZ-Tn5TM Custom Transposome Construction Kits", http://www.epicentre.com. pp. 1-17, 2012.
Erbacher et al., "Towards Integrated Continuous-Flow Chemical Reactors," Mikrochimica Acta. 131: 19-24 (1999).
Esser-Kahn et al., "Triggered release from polymer capsules," Macromolecules. 44: 5539-5553 (2011).
Fabi, et al. Correlation of efficacy between EGFR gene copy number and lapatinib/capecitabine therapy in HER2-positive metastatic breast cancer. J. Clin. Oncol. 2010; 28:15S. 2010 ASCO Meeting abstract Jun. 14, 2010:1059.
Fan et al., "Noninvasive diagnosis of fetal aneuploidy by shotgun sequencing DNA from maternal blood," Proc Natl Acad Sci U S A. 105(42):16266-71 (2008).
Fan et al., "Whole-genome molecular haplotyping of single cells," Nat Biotechnol. 29(1):51-7 (2011).
Fang et al., "Fluoride-cleavable biotinylation phosphoramidite for 5'-end-labeling and affinity purification of synthetic oligonucleotides," Nucleic Acids Res. 31(2):708-15 (2003).
Ferraro et al., "Microfluidic platform combining droplets and magnetic tweezers: application to HER2 expression in cancer diagnosis," Scientific Reports. 6:25540 (2016).
Flisher et al., "A scalable, fully automated process for construction of sequence-ready human exome targeted capture libraries," Genome Biol. 12(1):R1 (2011).
Frampton et al., "Development and validation of a clinical cancer genomic profiling test based on massively parallel DNA sequencing" Nat Biotechnol. 31(11):1023-1031 (2013).
Fredrickson et al., "Macro-to-micro interfaces for microfluidic devices," Lab Chip. 4(6): 526-33 (2004).
Freiberg et al., "Polymer microspheres for controlled drug release," Int J Pharm. 282(1-2): 1-18 (2004).
Fu et al., "A Microfabricated Fluorescence-Activated Cell Sorter," Nature Biotechnology. 17: 1109-1111 (1999).
Fulton et al., "Advanced multiplexed analysis with the FlowMetrix system," Clin Chem. 43(9): 1749-56 (1997).
Gangadharan et al., "DNA transposon Hermes insert into DNA in nucleosome-free regions in vivo," Proc Natl Acad Sci U S A. 107(51):21966-72 (2010).
Gao et al., "Toehold of dsDNA Exchange Affects the Hydrogel Swelling Kinetic of a Polymer-dsDNA Hybrid Hydrogel," Royal Soc Chem. 7:1741-1746 (2010).
Garstecki et al., "Mechanism for Flow-Rate Controlled Breakup in Confined Geometries: A Route to Monodisperse Emulsions," PRL. 94: 164501 (2005).
Garstecki et al., "Formation of monodisperse bubbles in a microfluidic flow-focusing device," Applied Physics Letters. 85(13): 2649-2651 (2004).
Gartner et al., "The Microfluidic Toolbox—examples for fluidic interfaces and standardization concepts," Proc SPIE 4982, Microfluidics, BioMEMS, and Medical Microsystems. (2003).
Gericke et al., "Functional cellulose beads: preparation, characterization, and applications," Chem Rev. 113(7) 4812-4836 (2013).
Ghadessy et al., "Directed evolution of polymerase function by compartmentalized self-replication," Proc Natl Acad Sci USA. 98: 4552-4557 (2001).
Gonzalez et al., "The influence of CCL3L1 gene-containing segmental duplications on HIV-1/AIDS susceptibility," Science. 307(5714): 1434-40 (2005).
Granieri, Lucia, Thesis: "Droplet-based microfluidics and engineering of tissue plasminogen activator for biomedical applications," Doctor of Philosophy in Chemistry, L'Universite de Strasbourg, 2009 (131 pages).
Grasland-Mongrain et al., "Droplet coalescence in microfluidic devices," <http://www.eleves.ens.fr/home/grasland/rapports/stage4.pdf>, dated Jan.-Jul. 2003 (31 pages).

(56) References Cited

OTHER PUBLICATIONS

Green et al., "Insertion site preference of Mu, Tn5, and Tn7 transposons," Mob DNA 3(1):3 (2012).
Greenleaf, "Assaying the epigenome in limited Nos. of cells," Methods. 72:51-6 (2015).
Guo et al., "Droplet microfluidics for high-throughput biological assays," Lab Chip. 12(12):2146-55 (2012).
Gyarmati et al., "Reversible disulphide formation in polymer networks: a versatile functional group from synthesis to applications," European Polymer Journal. 49:1268-1286 (2013).
Hamilton, "microRNA in erythrocytes," Biochem Soc Trans. 38 (Pt 1): 229-231.(2010).
Han et al., "Targeted Sequencing of Cancer-Related Genes in Colorectal Cancer Using Next- Generation Sequencing," PLOS One. 8(5):e64271 (2013).
Han et al., "CRISPR-Cas9 delivery to hard-to-transfect cells via membrane deformation" Science Advances. 1(7): E1500454 (2015) (8 pages).
Haring et al., "Chromatin immunoprecipitation: optimization, quantitative analysis and data normalization.," Plant Methods. 3:11 (2007).
Hashimshony et al., "CEL-Seq: Single-Cell RNA-Seq by Multiplexed Linear Amplification," Cell Rep. 2(3):666-73 (2012).
He, "Selective Encapsulation of Single Cells and Subcellular Organelles into Picoliter- and Femtoliter-Volume Droplets," Anal Chem. 77: 1539-1544 (2005).
He et al., "Genotyping-by-sequencing (GBS), an ultimate marker-assisted selections (MAS) tool to accelerate plant breeding," Frontiers Plant Sci. 5:1-8 (2014).
Hettiarachchi et al., "Controllable microfluidic synthesis of multiphase drug-carrying liposheres for site-targeted therapy," Biotechnol Prog. 25(4): 938-45 (2009).
Hiatt et al., "Parallel, tag-directed assembly of locally derived short sequence reads," Nat Methods. 7(2):119-22 (2010).
Hirsch et al. "Easily reversible desthiobiotin binding to streptavidin, avidin, and other biotin-binding proteins: uses for protein labeling, detection, and isolation." Anal Biochem. 308(2):343-357 (2002).
Hjerten et al., "General methods to render macroporous stationary phases nonporous and deformable, exemplified with agarose and silica beads and their use in high-performance ion-exchange and hydrophobic-interaction chromatography of proteins," Chromatographia. 31.1-2: 85-94 (1991).
Holmberg et al., "The biotin-streptavidin interaction can be reversibly broken using water at elevated temperatures," Electrophoresis. 26(3):501-10 (2005).
Holtze et al., "Biocompatible surfactants for water-in-fluorocarbon emulsions," Lab Chip. 8(10): 1632-9 (2008).
Hosokawa et al., "Massively parallel whole genome amplification for single-cell sequencing using droplet microfluidics," Scientific Reports. 7: No. 5199 (2017).
Hosono et al., "Unbiased whole-genome amplification directly from clinical samples, " Genome Res. 13(5):954-64 (2003).
Hu et al., "Shape Controllable Microgel Particles Prepared by Microfluidic Combining External Crosslinking," Biomicrofluidics. 6(2):26502-265029 (2012).
Huebner, "Quantitative detection of protein expression in single cells using droplet microfluidics," Chem Commun. 1218-1220 (2007).
Hug et al., "Measurement of the number of molecules of a single mRNA species in a complex mRNA preparation," J Theor Biol. 221(4): 615-24 (2003).
Hung et al., "PLGA micro/nanosphere synthesis by droplet microfluidic solvent evaporation and extraction approaches," Lab chip. 10: 1820-1825 (2010).
Hung et al., "Alternating droplet generation and controlled dynamic droplet fusion in microfluidic device for Cds nanoparticle synthesis," Lab Chip. 6(2): 174-8 (2006).
Illumina Nextera Enrichment Sample Preparation Guide. Feb. 2013.
Illumina TruSeq Custom Enrichment Kit Data Sheet. (c) 2014.

Imburgio et al., "Studies of promoter recognition and start site selection by T7 RNA polymerase using a comprehensive collection of promoter variants," Biochemistry. 39(34):10419-30 (2000).
Invitrogen Dynal, Product Sheet for "Dynabeads@ M-280 Streptavidin," (2006) (2 pages).
Ioannidis, N. Manufacturing of agarose-based chromatographic adsorbents with controlled pore and particle sizes. A thesis submitted to The University of Birmingham for the degree of Doctor of Philosophy. 2009.
Ivanova et al., "Droplet Formation in a Thin Layer of a Two-Component Solution under the Thermal Action of Laser Radiation," Colloid Journal. 69(6): 735-740 (2007).
Jeffries et al., "Controlled Shrinkage and Re-expansion of a Single Aqueous Droplet inside an Optical Vortex Trap," J Phys Chem B. 111(11): 2806-2812 (2007).
Jeffries et al., "Dynamic modulation of chemical concentration in an aqueous droplet," Angew Chem Int Ed Engl. 46(8): 1326-1328 (2007).
Jena et al., "Cyclic olefin copolymer based microfluidic devices for biochip applications: Ultraviolet surface grafting using 2-methacryloyloxyethyl phosphorylcholine," Biomicrofluidics. 6(1): 12822-1282212 (2012).
Joanicot et al., "Droplet Control For Microfluidics," Science. 309:887-888 (2005).
Johnson, "Rapid microfluidic mixing," Analytical Chemistry. 74(1): 45-51 (2002).
Joneja et al., "Linear nicking endonuclease-mediated strand-displacement DNA amplification," Anal Biochem. 414(1):58-69 (2011).
JPK "Determining the elastic modulus of biological samples using atomic force microscopy" (https://www.jpk.com/app-technotes-img/AFM/pdf/jpk-app-elastic-modulus.14-1.pdf) 2009, pp. 1-9 (Year: 2009).
Jung et al., "Micro machining of injection mold inserts for fluidic channel of polymeric biochips," Sensors. 7(8): 1643-1654 (2007).
Kamperman et al., "Centering Single Cells in Microgels via Delayed Crosslinking Supports Long-Term 3D Culture by Preventing Cell Escape," Small. 13(22) (2017).
Kaper et al., "Supporting Information for Whole-genome haplotyping by dilution, amplification, and sequencing," Proc Natl Acad Sci U S A. 110(14):5552-7 (2013).
Kaper et al., "Whole-genome haplotyping by dilution, amplification, and sequencing," Proc Natl Acad Sci U S A. 110(14):5552-7 (2013).
Karmakar et al., "Organocatalytic removal of formaldehyde adducts from RNA and DNA bases," Nat Chem. 7(9):752-8 (2015).
Katsura et al., "Indirect micromanipulation of single molecules in water-in-oil emulsion," Electrophoresis. 22(2): 289-93 (2001).
Kawari et al., "Mass-Production System of Nearly Monodisperse Diameter Gel Particles Using Droplets Formation in a Microchannel," Micro Total Analysis Systems. 1:368-370 (2002).
Kebschull et al., "High-Throughput Mapping of Single-Neuron Projections by Sequencing of Barcoded RNA," Neuron. 91(5):975-87 (2016).
Kenis et al., "Microfabrication Inside Capillaries Using Multiphase Laminar Flow Patterning," Science. 285: 83-85 (1999).
Khomiakova et al., "Analysis of perfect and mismatched DNA duplexes by a generic hexanucleotide microchip," Mol Biol (Mosk). 37(4): 726-41 (2003) (Abstract only).
Kim et al., "Albumin loaded microsphere of amphiphilic poly( ethylene glycol)/poly(a-ester) multiblock copolymer," Eu J Pharm Sci. 23: 245-51 (2004).
Kim et al., "Fabrication of monodisperse gel shells and functional microgels in microfluidic devices," Angew Chem Int Ed Engl. 46(11): 1819-22 (2007).
Kim et al., "Rapid prototyping of microfluidic systems using a PDMS/polymer tape composite," Lab Chip. 9(9): 1290-3 (2009).
Kirkness et al., "Sequencing of isolated sperm cells for direct haplotyping of a human genome," Genome Res. 23:826-83 (2013).
Kitzman et al., "Haplotype-resolved genome sequencing of a Gujarati Indian individual." Nat Biotechnol. 29:59-63 (2011).
Kitzman et al., "Noninvasive whole-genome sequencing of a human fetus," Sci Transl Med. 4(137):137ra76 (2016).

(56) References Cited

OTHER PUBLICATIONS

Kivioja et al., "Counting absolute Nos. of molecules using unique molecular identifiers," Nat Methods. 9(1):72-4 (2011).
Klein et al., "Droplet barcoding for single-cell transcriptomics applied to embryonic stem cells," Cell. 161(5): 1187-201 (2015).
Knapp et al., "Generating barcoded libraries for multiplex high-throughput sequencing," Methods Mol Biol. 840:155-70 (2012).
Knight et al., "Subtle chromosomal rearrangements in children with unexplained mental retardation," Lancet. 354(9191):1676-81 (1999).
Kobayashi et al., "Straight-Through Microchannel Devices For Generating Monodisperse Emulsion Droplets Several Microns In Size," Microfluid Nanofluid. 4: 167-177 (2008).
Kobayashi et al., "Effect of slot aspect ratio on droplet formation from silicon straight-through microchannels," J Colloid Interface Sci. 279(1): 277-80 (2004).
Kohler et al., "Nanoliter Segment Formation in Micro Fluid Devices For Chemical and Biological Micro Serial Flow Processes in Dependence on Flow Rate and Viscosity," Sensors and Actuators A. 119: 19-27 (2005).
Kolodeziejczyk et al., "The technology and biology of single-cell RNA sequencing," Molecular Cell. 58(4): 610-20 (2015).
Korlach et al., "Methods in Enzymology, Real-Time DNA Sequencing from Single Polymerase Molecules," 472:431-455 (2010).
Koster et al., "Drop-based microfluidic devices for encapsulation of single cells," Lab Chip. 8(7): 1110-1115 (2008).
Kozarewa et al., "96-plex molecular barcoding for the Illumina Genome Analyzer," Methods Mol Biol. 733:279-98 (2011).
Kozarewa et al., "Amplification-free Illumina sequencing-library preparation facilitates improved mapping and assembly of GC-biased genomes," Nat Methods. 6: 291-5 (2009).
Kutyavin, et al., "Oligonucleotides containing 2-aminoadenine and 2-thiothymine act as selectively binding complementary agents," Biochemistry. 35(34):11170-6 (1996).
Kwok et al., "Single-molecule analysis for molecular haplotyping," Hum Mutat. 23:442-6 (2004).
Lagally et al., "Single-Molecular DNA Amplification and Analysis in an Integrated Microfluidic Device," Anal Chem. 73(3): 565-70 (2001).
Lagus et al., "A review of the theory, methods and recent applications of high-throughput single-cell droplet microfluidics," J Phys D Appl Phys. 46:114005 (2013) (21 pages).
Lai et al., "Characterization and Use of Laser-Based Lysis for Cell Analysis on-Chip," Journal of the Royal Society. 5(2): S113-S121(2008).
Laird et al., "Hairpin-bisulfite PCR: Assessing epigenetic methylation patterns on complementary strands of individual DNA molecules," PNAS. 101, 204-209 (2004).
Lake et al., "Integrative Single-Cell Analysis By Transcriptional And Epigenetic States in Human Adult Brain," Apr. 19, 2017. doi: https://doi.org/10.1101/128520.
Lan et al. "Single-cell genome sequencing at ultra-high-throughput with microfluidic droplet barcoding" Nat Biotechnol. 35(7):640-646(2017).
Lander et al., "Initial sequencing and analysis of the human genome," Nature. 409: 860-921 (2001).
Lasken et al., "Archaebacterial DNA Polymerases Tightly Bind Uracil-containing Dna," J Biol Chem. 271(30):17692-17696 (1996).
Laulicht et al., "Evaluation of continuous flow nanosphere formation by controlled microfluidic transport," Langmuir. 24(17): 9717-26 (2008).
Lebedev et al,. "Hot Start PCR with heat-activatable primers: a novel approach for improved PCR performance," NAR. 36(20):E131-1 (2008).
Lee et al., "Alginate: Properties and biomedical applications," Prog Polym Sci. 37(1):106-126 (2012).
Lee et al., "A tunable microflow focusing device utilizing controllable moving walls and its applications for formation of microdroplets in liquids," J Micromech Microeng. 17: 1121-1129 (2007).
Lee et al., "Double emulsion-templated nanoparticle colloidosomes with selective permeability," Adv Mater. 20: 3498-503 (2008).
Lee et al., "ACT-PRESTO: Rapid and consistent tissue clearing and labeling method for 3-dimensional (3D) imaging," Sci Rep. 6:18631 (2016).
Lee et al., "Highly multiplexed subcellular RNA sequencing in situ," Science. 343(6177): 1360-3 (2014).
Lee et al., "Microfluidic air-liquid cavity acoustic transducers for on-chip integration of sample preparation and sample detection," JALA. 15(6): 449-454 (2010).
Lee et al., "Fluorescent in situ sequencing (FISSEQ) of RNA for gene expression profiling in intact cells and tissues," Nature Protocols. 10(3):442-458 (2015).
Lennon et al., "A scalable, fully automated process for construction of sequence-ready barcoded libraries for 454," Genome Biol. 11(2):R15 (2010).
Li et al., "A single-cell-based platform for copy No. variation profiling through digital counting of amplified genomic DNA fragments," ACS Appl Mater Interfaces. doi: 10.1021/acsami.7b03146 (2017).
Li et al., "Step-emulsification in a microfluidic device," Lab Chip. 15(4): 1023-31 (2015).
Li et al., "PEGylated PLGA Nanoparticles as protein carriers: synthesis, preparation and biodistribution in rats," Journal of Controlled Release. 71: 203-211 (2001).
Lienemann et al., "Single cell-laden protease-sensitive microniches for long-term culture in 3,". Lab Chip. 17(4):727-737(2017).
Linch et al., "Bone marrow processing and cryopreservation," Journal of Clinical Pathology. 35(2): 186-190 (1982).
Liu et al., "Droplet-based synthetic method using microflow focusing and droplet fusion," Microfluid Nanofluid. 3: 239-24 (2007).
Liu et al., "Dynamics of coalescence of plugs with a hydrophilic wetting layer induced by flow in a microfluidic chemistrode," Langmuir. 25(5): 2854-9 (2009).
Liu et al., "Droplet formation in a T-shaped microfluidic junction," Journal of Applied Physics. 106: 034906 (2009).
Liu et al., "Preparation of uniform-sized PLA microcapsules by combining Shirasu porous glass membrane emulsification technique and multiple emulsion-solvent evaporation method," J Control Release. 103(1): 31-43 (2005).
Liu et al., "Smart thermo-triggered squirting capsules for Nanoparticle delivery," Soft Matter. 6(16): 3759-3763 (2010).
Lo et al., "On the design of clone-based haplotyping," Genome Biol. 14(9):R100 (2013).
Lorenceau et al., "Generation of Polymerosomes from Double-Emulsions," Langmuir. 21: 9183-9186 (2005).
Loscertales et al., "Micro/Nano Encapsulation via Electrified Coaxial Liquid Jets," Science. 295: 1695-1698 (2002).
Love, "A microengraving method for rapid selection of single cells producing antigen-specific antibodies," Nature Biotech. 24(6): 703 (2006).
Lowe, Adam James, Thesis: "Norbornenes and [n]polynorbornanes as molecular scaffolds for anion recognition," Doctor of Philosophy, Deakin University, 2010 (361 pages).
Lundin et al., "Hierarchical molecular tagging to resolve long continuous sequences by massively parallel sequencing," Sci Rep. 3:1186 (2003).
Lupski et al., "Genomic rearrangements and sporadic disease," Nat Genet. 39(7 Suppl):S43-7 (2007).
Maan et al., "Spontaneous droplet formation techniques for monodisperse emulsions preparation—Perspectives for food applications," Journal of Food Engineering. 107(3-4): 334-346 (2011).
Macaulay et al., "Single-Cell Multiomics: Multiple Measurements from Single Cells," available in PMS Dec. 18, 2017, published in final edited form as: Trends in Genetics. 33(2): 155-168 (2017).
Macaulay et al., "G&T-seq: parallel sequencing of single-cell genomes and transcriptomes," Nature Methods. p. 1-7 (2005).
Macosko et al., "Highly Parallel Genome-wide Expression Profiling of Individual Cells Using Nanoliter Droplets," Cell. 161(5): 1202-14 (2015).
Mair et al., "Injection molded microfluidic chips featuring integrated interconnects," Lab Chip. 6(10): 1346-54 (2006).
Makino et al., "Preparation of hydrogel microcapsules: Effects of preparation conditions upon membrane properties," Colloids and Surfaces B: Biointerfaces. 12(2): 97-104 (1998).

(56) References Cited

OTHER PUBLICATIONS

Malic et al., "Integration and detection of biochemical assays in digital microfluidic LOC devices," Lab Chip. 10: 418-431 (2010).
Malsch et al., "μPIV-Analysis of Taylor flow in micro channels," Chemical Engineering Journal. 135S: S166-S172 (2008).
Man, Piu Francis, Thesis: "Monolithic Structures for Integrated Microfluidic Analysis," Doctor of Philosophy in Electrical Engineering, University of Michigan, 2001 (145 pages).
Marcus, "Gene method offers diagnostic hope," The Wall Street Journal, <https://www.wsj.com/articles/SB10001424052702303644004577520851224339844>, dated Jul. 11, 2012.
Maricic et al., "Optimization of 454 sequencing library preparation from small amounts of DNA permits sequence determination of both DNA strands," Biotechniques. 46(1):51-2, 54-7 (2009).
Mason et al., "Shear Rupturing of Droplets in Complex Fluids," Langmuir. 13(17):4600-4613 (1997).
Matochko et al., "Uniform amplification of phage display libraries in monodisperse emulsions," Methods. 58(1): 18-27 (2012).
Mazutis et al., "Droplet-Based Microfluidic Systems for High-Throughput Single DNA Molecule Isothermal Amplification and Analysis," Anal Chem. 81(12): 4813-4821 (2009).
Mazutis et al., "Selective droplet coalescence using microfluidic systems," Lab Chip. 12(10): 1800-6 (2012).
Mazutis et al., "Preparation of monodisperse emulsions by hydrodynamic size fractionation," Appl Phys Lett. 95: 204103 (2009).
Mcginnis et al., "MULTI-seq: Scalable sample multiplexing for single-cell RNA sequencing using lipid-tagged indices," bioRxiv 387241; doi: https://doi.org/10.1101/387241.
Meier et al., "Plug-Based Microfluidics with Defined Surface Chemistry to Miniaturize and control aggregation of amyloidogenic peptides," Angew Chem Ed Engl. 48(8): 1487-1489 (2009).
Merriman et al., "Progress in ion torrent semiconductor chip based sequencing," Electrophoresis. 33(23): 3397-417 (2012).
Microfluidic ChipShop, Microfluidic Product Catalogue, dated Feb. 2005.
Microfluidic ChipShop, Microfluidic product catalogue, dated Mar. 2005.
Microfluidic ChipShop, Microfluidic product catalogue, dated Oct. 2009.
Miller et al., "An improved zinc-finger nuclease architecture for highly specific genome editing," Nat Biotechnol. 25:778-785 (2007).
Miller-Stephenson Chemicals 157 FS Series catalog, www.miller-stephenon.com.
MiRNA (http://www.exiqon.com/what-are-microRNAs) accessed Oct. 19, 2017.
Mirzabekov, "DNA Sequencing by Hybridization—a Megasequencing Method and A Diagnostic Tool?" Trends in Biotechnology. 12(1): 27-32 (1994).
Moore et al., "Behavior of capillary valves in centrifugal microfluidic devices prepared by three-dimensional printing," Microfluidics and Nanofluidics. 10(4):877-888 (2011).
Morgan et al., "Chapter 12: Human microbiome analysis," PLoS Comput Biol. 8(12):e1002808 (2012).
Morimoto et al., "Monodisperse semi-permeable microcapsules for continuous observation of cells," Lab Chip 9(15):2217-2223 (2009).
Morton, "Parameters of the human genome," Proc Natl Acad Sci U S A. 88(17):7474-6 (1991).
Mouritzen et al., "Single nucleotide polymorphism genotyping using locked nucleic acid (LNa)," Expert Rev Mol Diagn. 3(1): 27-38 (2003).
Mozhanova, A.A. et al. "Local elastic properties of biological materials studied by SFM" (2003) XP055314108, Retrieved from the Internet: URL:http://www.ntmdt.com/data/media/files/publications/2003/08.08_a.a.mozhanova_n.i.n_english.pdf.
Muotri et al., "L1 retrotransposition in neurons is modulated by MeCP2," Nature. 468(7322):443-6 (2010).
Myllykangas et al., "Targeted Sequencing Library Preparation By Genomic DNA Circularization," BMC Biotechnology. 11(122), 1-12 (2011).
Nagano et al., "Single-cell Hi-C reveals cell-to-cell variability in chromosome structure," Nature. 502(7469):59-64 (2013).
Nagashima et al., "Preparation of monodisperse poly (acrylamide-co-acrylic acid) hydrogel microspheres by a membrane emulsification technique and their size-dependent surface properties," Colloids and Surfaces B: Biointerfaces. 11(1-2): 47-56 (1998).
Narayanan et al., "Determination of agarose gel pore size: Absorbance measurements vis a vis other techniques," Journal of Physics: Conference Series 28. 83-86 (2006).
National Human Genome Research Institute (NHGRI), "The Human Genome Project Completion: Frequently Asked Questions," retrieved from <https://www.genome.gov/11006943/human-genome-project-completion-frequently-asked-questions/> on May 10, 2018, last updated Oct. 30, 2010 (8 pages).
Navin, "The first five years of single-cell cancer genomics and beyond," Genome Res. 25(10):1499-507 (2015).
Nguyen et al., "In situ hybridization to chromosomes stabilized in gel microdrops," Cytometry. 21(2):111-9 (1995).
Nisisako et al., "Novel microreactors for functional polymer beads," Chem Eng J. 101(1-3):23-9 (2004).
Nisisako et al., "Synthesis of Monodisperse Bicolored Janus Particles with Electrical Anisotropy Using a Microfluidic Co-Flow System," Adv Mater. 18(9):1152-6 (2006).
Nisisako et al., "Droplet formation in a microchannel network," Lab Chip. 2(1):24-6 (2002).
Nisisako et al., "Droplet Formation in a Microchannel on PMMA Plate," *Micro Total Analysis Systems 2001*. J.M. Ramsey and A. van den Berg, 137-138 (2001).
Nisisako et al., "Microfluidic large-scale integration on a chip for mass production of monodisperse droplets and particles," Lab Chip. 8(2):287-293 (2008).
Niu et al., "Droplet-based compartmentalization of chemically separated components in two-dimensional separations," Chem Commun (Camb). (41):6159-61 (2009).
Niu et al., "A hybrid microfluidic chip for digital electro-coalescence of droplets, " Thirteenth International Conference on Miniaturized Systems for Chemistry and Life Sciences, Nov. 1-5, Jeju, Korea. pp. 94-96 (2009).
Novak et al., "Single cell multiplex gene detection and sequencing using microfluidically-generated agarose emulsions," available in PMC Jan. 10, 2012, published in final edited form as: Angew Chem Int Ed Engl. 50(2):390-5 (2011) (10 pages).
Oberholzer et al., "Polymerase chain reaction in liposomes," Chem Biol. 2(10):677-82 (1995).
Ogawa et al., "Production and characterization of O/W emulsions containing cationic droplets stabilized by lecithin-chitosan membranes," J Agric Food Chem. 51(9):2806-12 (2003).
Okushima et al., "Controlled Production of Monodisperse Double Emulsions by Two-Step Droplet Breakup in Microfluidic Devices," Langmuir. 20(23):9905-8 (2004).
Oligotex Handbook. For purification of poly A+ RNA from total RNA and directly from cultured cells or tissues as well as purification of polyadenylated in vitro transcripts. Jun. 2012.
Ong et al., "Experimental and computational analysis of droplet formation in a high-performance flow-focusing geometry," Sensors and Actuators A: Physical. 138(1):203-12 (2007).
Orakdogen et al., "Novel responsive poly(N,N-dimethylaminoethyl methacrylate) gel beads: preparation, mechanical properties and pH-dependent swelling behavior," J Polym Res. 19:9914 (2012).
Oyola et al., "Optimizing Illumina next-generation sequencing library preparation for extremely AT-biased genomes," BMC Genomics. 13:1 (2012).
Pantel et al., "Detection methods of circulating tumor cells," J Thorac Dis. 4(5):446-7 (2012).
Park et al., "ChIP-seq: advantages and challenges of a maturing technology," Nature Reviews Genetics. 10: 669-680 (2009).
Patel et al., "Single-cell RNA-seq highlights intratumoral heterogeneity in primary glioblastoma," Science. 344(6190):1396-401 (2014).
Perez et al., "Poly(lactic acid)-poly(ethylene glycol) nanoparticles as new carriers for the delivery of plasmid Dna," J Control Release. 75(1-2):211-24 (2001).

(56) References Cited

OTHER PUBLICATIONS

Perrott, Jimmy, Thesis: "Optimization and Improvement of Emulsion PCR for the Ion Torrent Next-Generation Sequencing Platform," Bachelor of Science in Bioengineering, University of California, Santa Cruz, 2011 (25 pages).
Perroud et al., "Isotropically etched radial micropore for cell concentration, immobilization, and picodroplet generation," Lab Chip. 9(4):507-15 (2009).
Peters et al., "Accurate whole-genome sequencing and haplotyping from 10 to 20 human cells," Nature. 487(7406):190-5 (2012).
Picot et al., "A biomimetic microfluidic chip to study the circulation and mechanical retention of red blood cells in the spleen" Am J Hematology. 90(4):339-345 (2015).
Pinto et al., "Functional impact of global rare copy number variation in autism spectrum disorders," Nature. 466(7304):368-72 (2015).
Plunkett et al., "Chymotrypsin responsive hydrogel: application of a disulfide exchange protocol for the preparation of methacrylamide containing peptides," Biomacromolecules. 6(2):632-7 (2005).
Porteus et al., "Chimeric nucleases stimulate gene targeting in human cells," Science. 300(5620):763 (2003).
Pott et al., "Single-cell ATAC-seq: strength in numbers," Genome Biol. 16(1):172 (2015).
Preissl, et al. Single nucleus analysis of the chromatin landscape in mouse forebrain development. Posted Jul. 4, 2017. bioRxiv 159137; doi: https://doi.org/10.1101/159137.
Qiagen, "Omniscript® Reverse Transcription Handbook," Oct. 2010 (32 pages).
Rakszewska, A. et al. "One drop at a time: toward droplet microfluidics as a versatile tool for single-cell analysis" NPG Asia Materials (2014) 6(10):e133 (12 pages).
Ram et al., "Strategy for microbiome analysis using 16S rRNA gene sequence analysis on the Illumina sequencing platform," Syst Biol Reprod Med. 57(3):162-70 (2011).
Ramsey, "The burgeoning power of the shrinking laboratory" Nat Biotechnol. 17(11):1061-2 (1999).
Ramskold et al., "Full-length mRNA-Seq from single-cell levels of RNA and individual circulating tumor cells" Nat Biotechnol. 30(8):777-782 (2012).
Ran et al., "Genome engineering using the CRISPR-Cas9 system," available in PMC Mar. 30, 2014, published in final edited form as: Nat Protoc. 8(11):2281-2308 (2013) (49 pages).
Reis et al., "CRISPR/Cas9 and Targeted Genome Editing: A New Era in Molecular Biology," XP002766825: URL:https://ww.neb.com/tools-and-resources/feabture-articles/crispr- cas9-and-targeted-genome-editing-a-new-era-in-molecular-biology (2014).
Reisner et al., "Single-molecule denaturation mapping of DNA in nanofluidic channels," Proc Natl Acad Sci U S.A., 107: 13294-9,(2010).
Repp et al., "Genotyping by Multiplex Polymerase Chain Reaction for Detection of Endemic Hepatitis B Virus Transmission" J Clinical Microbiology. 31:1095-1102 (1993).
Richardson et al., "Novel inhibition of archaeal family-D DNA polymerase by uracil," Nucleic Acids Res. 41(7):4207-18 (2013).
Roche, "Using Multiplex Identifier (MID) Adaptors for the GS FLX Titanium Chemistry Basic MID Set Genome Sequencer FLX System," Technical Bulletin 004-2009, <http://454.com/downloads/my454/documentation/technical-bulletins/TCB-09004 UsingMultiplexIdentifierAdaptorsForTheGSFLXTitaniumSeriesChemistry-BasicMIDSet.pdf>, dated Apr. 1, 2009 (7 pages).
Roche, "Using Multiplex Identifier (MID) Adaptors for the GS FLX Titanium Chemistry Extended MID Set Genome Sequencer FLX System," Technical Bulletin 005-2009, <http://454.com/downloads/my454/documentation/technical-bulletins/TCB-09005UsingMultiplexIdentifierAdaptorsForTheGSFLXTitaniumChemistry-ExtendedMIDSet.pdf>, dated Apr. 1, 2009 (7 pages).
Rodrigue et al., "Whole genome amplification and de novo assembly of single bacterial cells," PLoS One. 4(9):e6864 (2009).
Rogozin et al., "A highly conserved family of inactivated archaeal B family DNA polymerases," Biol Direct. 3:32 (2008).
Ropers, "New perspectives for the elucidation of genetic disorders," Am J Hum Genet. 81(2):199-207 (2007).
Rotem et al., "High-Throughput Single-Cell Labeling (Hi-SCL) for RNA-Seq Using Drop-Based Microfluidics," PLoS One. 10(5):e0116328 (2015).
Rotem et al., "Single Cell Chip-Seq Using Drop-Based Microfluidics," Frontiers of Single Cell Analysis, September 5-7, Stanford University. Abstract #50 (2013).
Rotem et al., "Single-cell ChIP-seq reveals cell subpopulations defined by chromatin state," Nat Biotechnol. 33(11):1165-72 (2015).
Ryan et al., "Rapid assay for mycobacterial growth and antibiotic susceptibility using gel microdrop and encapsulation," J Clin Microbiol. 33(7):1720-6 (1995).
Sahin et al., "Microfluidic EDGE emulsification: the importance of interface interactions on droplet formation and pressure stability," Sci Rep. 6:26407 (2016).
Sakaguchi et al., "Cautionary Note on the Use of dUMP-Containing PCR Primers with Pfu and VentR®," BioTechniques. 21(3): 369-370 (1996).
Sander et al., "Selection-free zinc-finger-nuclease engineering by context-dependent assembly (CoDA)," Nat Methods. 8(1):67-9 (2011).
Savva et al., "The structural basis of specific base-excision repair by uracil-DNA glycosylase," Nature. 373(6514):487-93 (1995).
Schirinzi et al., "Combinatorial sequencing-by-hybridization: Analysis of the NF1 gene," Genet Test. 10(1):8-17 (2006).
Schmeider et al., "Fast identification and removal of sequence contamination from genomic and metagenomic datasets," PLoS One. 6(3):e17288 (2011).
Schmitt et al., "Bead-based multiplex genotyping of human papillomaviruses," J Clin Microbiol. 44(2):504-12 (2006).
Schubert et al., "Microemulsifying fluorinated oils with mixtures of fluorinated and hydrogenated surfactants," Colloids and Surfaces A: Physicochemical and Engineering Aspects. 84(1):97-106 (1994).
Schwartz et al., "Capturing native long-range contiguity by in situ library construction and optical sequencing," Proc Natl Acad Sci U S A. 109(46):18749-54 (2012).
Sebat et al., "Strong association of de novo copy number mutations with autism," Science. 316(5823):445-9 (2007).
Seiffert et al., "Microfluidic fabrication of smart microgels from macromolecular precursors," Polymer. 51(25):5883-9 (2010).
Seiffert et al., "Smart microgel capsules from macromolecular precursors," J Am Chem Soc. 132(18):6606-9 (2010).
Sessoms et al., "Droplet motion in microfluidic networks: Hydrodynamic interactions and pressure-drop measurements," Phys Rev E Stat Nonlin Soft Matter Phys. 80(1 Pt 2):016317 (2009).
Shah et al., "Fabrication of monodisperse thermosensitive microgels and gel capsules in microfluidic devices," Soft Matter. 4(12):2303-9 (2008).
Shahi et al., "Abseq: Ultrahigh-throughput single cell protein profiling with droplet microfluidic barcoding," Sci Rep. 7:44447 (2017).
Shaikh et al., "A modular microfluidic architecture for integrated biochemical analysis," Proc Natl Acad Sci U S A. 102(28):9745-9750 (2005).
Shimkus et al., "A chemically cleavable biotinylated nucleotide: usefulness in the recovery of protein-DNA complexes from avidin affinity columns," Proc Natl Acad Sci U S A. 82(9):2593-7 (1985).
Shlien et al., "Copy number variations and cancer," Genome Med. 1(6):62 (2009).
Shlien et al., "Excessive genomic DNA copy number variation in the Li-Fraumeni cancer predisposition syndrome," Proc Natl Acad Sci U S A. 105(32):11264-9 (2008).
Shuttleworth et al., "Recognition of the pro-mutagenic base uracil by family B DNA polymerases from archaea," J Mol Biol. 337(3):621-34 (2004).
"Streptavidin-agarose (S1638) product information sheet," Sigma, <www.sigma-aldrich.com>.
Simeonov et al., "Single nucleotide polymorphism genotyping using short, fluorescently labeled locked nucleic acid (LNA) probes and fluorescence polarization detection," Nucleic Acids Res. 30(17):e91 (2002).

(56) References Cited

OTHER PUBLICATIONS

Simon et al., "Using formaldehyde-assisted isolation of regulatory elements (FAIRE) to isolate active regulatory DNA," Nat Protoc. 7(2):256-67 (2012).
Skerra, "Phosphorothioate primers improve the amplification of DNA sequences by DNA polymerases with proofreading activity," Nucleic Acids Res. 20(14):3551-4 (1992).
Smith et al., "Highly-multiplexed barcode sequencing: an efficient method for parallel analysis of pooled samples," Nucleic Acids Res. 38(13):e142 (2010).
Song et al., "Reactions in droplets in microfluidic channels," Angew Chem Int Ed Engl. 45(44):7336-56 (2006).
Song et al., "DNase-seq: A High-Resolution Technique for Mapping Active Gene Regulatory Elements across the Genome from Mammalian Cells," Cold Spring Harb Protoc. 2 (2010) (13 pages).
Sorokin et al., "Discrimination between perfect and mismatched duplexes with oligonucleotide gel microchips: role of thermodynamic and kinetic effects during hybridization," J Biomol Struct Dyn. 22(6):725-34 (2005).
"Spormann Laboratory, Polymerase Chain Reaction (PCR)," Alfred Spormann Laboratory. 1-3 (2009).
Srisa-Art et al., "High-throughput DNA droplet assays using picoliter reactor volumes," Anal Chem. 79(17):6682-9 (2007).
Stoeckius et al., "Large-scale simultaneous measurement of epitopes and transcriptomes in single cells," available in PMC Jan. 31, 2018, published in final edited form as: Nat Methods. 14(9):865-868 (2017).
Stoeckius et al., "Simultaneous epitope and transcriptome measurement in single cells," Nat Methods. 14: 865-868 (2017) (Supplemental Materials).
Su et al., "Microfluidics-Based Biochips: Technology Issues, Implementation Platforms, and Design—Automation Challenges," IEEE Transactions on Computer-Aided Design of Integrated Circuits and Systems. 25(2):211-23 (2006).
Sun et al., "Progress in research and application of liquid-phase chip technology," Chin J Exp Surg. 22(5):639-40 (2005) (7 pages).
Susaki et al., "Whole-brain imaging with single-cell resolution using chemical cocktails and computational analysis," Cell. 157(3):726-39 (2014).
Syed et al., "Next-generation sequencing library preparation: simultaneous fragmentation and tagging using in vitro transposition," Nat Methods. 6: i-ii (2009).
Tawfik et al., "Man-made cell-like compartments for molecular evolution," Nat Biotechnol. 16(7):652-6 (1998).
Tayyab et al., "Size exclusion chromatography and size exclusion HPLC of proteins," Biochem Ed, Pergamon. 19(3):149-152 (1991).
Tetradis-Meris et al., "Novel parallel integration of microfluidic device network for emulsion formation," Ind Eng Chem Res. 48(19):8881-9 (2009).
Tewhey et al., "Supplementary Materials," Nature Biotechnology. 27(11): 1-22 (2009).
Tewhey et al., "Microdroplet-based PCR amplification for large-scale targeted sequencing," available in PMC May 1, 2010, published in final edited form as: Nat Biotechnol. 27(11):1025-31 (2009) (22 pages).
Theberge et al., "Microdroplets in microfluidics: an evolving platform for discoveries in chemistry and biology," Angew Chem Int Ed Engl. 49(34):5846-68 (2010).
"Protocols, M-270 Streptavidin," ThermoFisherScientific. (2007) (5 pages).
Thorsen et al., "Dynamic pattern formation in a vesicle-generating microfluidic device," Phys Rev Lett. 86(18):4163-4166 (2001).
Tomer et al., "Advanced CLARITY for rapid and high-resolution imaging of intact tissues," Nat Protoc. 9(7):1682-97 (2014).
Tonelli et al., "Perfluoropolyether functional oligomers: unusual reactivity in organic chemistry" Journal of Fluorine Chemistry. 118(1-2):107-21 (2002).
Tubeleviciute et al., "Compartmentalized self-replication (CSR) selection of Thermococcus litoralis Sh1B DNA polymerase for diminished uracil binding," Protein Eng Des Sel. 23(8):589-97 (2010).
Turner et al., "High-throughput haplotype determination over long distances by haplotype fusion PCR and ligation haplotyping," Nat Protoc. 4(12):1771-83 (2009).
Turner et al., "Assaying chromosomal inversions by single-molecule haplotyping," Nat Methods. 3(6):439-45 (2006).
Turner et al., "Methods for genomic partitioning," Annu Rev Genomics Hum Genet. 10:263-84 (2009).
Umbanhowar et al., "Monodisperse Emulsion Generation via Drop Break Off in a Coflowing Stream," Langmuir. 16(2):347-51 (2000).
Ushijima et al., "Detection and interpretation of altered methylation patterns in cancer cells," Nat Rev Cancer. 5: 223-231 (2005).
Van Dijke et al., "Effect of viscosities of dispersed and continuous phases in microchannel oil-in-water emulsification," Microfluid Nanofluid. 9:77-85 (2010).
Van Nieuwerburgh et al., "Illumina mate-paired DNA sequencing-library preparation using Cre-Lox recombination," Nucleic Acids Res. 40(3): e24 (2012).
Wagner et al., "Biocompatible fluorinated polyglycerols for droplet microfluidics as an alternative to PEG-based copolymer surfactants," Lab Chip. 16(1):65-9 (2016).
Wang et al., "Self-Formed Adaptor PCR: a Simple and Efficient Method for Chromosome Walking," Appl Environ Microbiol. 73(15):5048-51 (2007).
Wang et al., "Single nucleotide polymorphism discrimination assisted by improved base stacking hybridization using oligonucleotide microarrays," Biotechniques. 35(2):300-8 (2003).
Wang et al., "A novel thermo-induced self-bursting microcapsule with magnetic-targeting property," Chemphyschem. 10(14):2405-9 (2009).
Wang et al., "Digital karyotyping," Proc Natl Acad Sci U S A. 99(25):16156-61 (2002).
Ward et al., "Microfluidic flow focusing: drop size and scaling in pressure versus flow-rate-driven pumping," Electrophoresis. 26(19):3716-24 (2005).
Weaver, "Rapid clonal growth measurements at the single-cell level: gel microdroplets and flow cytometry," Biotechnology (N Y). 9(9):873-877 (1991).
Weigl et al., "Microfluidic Diffusion-Based Separation and Detection," Science. 283(5400):346-7 (1999).
Wesolowska et al., "Cost-effective multiplexing before capture allows screening of 25 000 clinically relevant SNPs in childhood acute lymphoblastic leukemia, " Leukemia. 25(6):1001-6 (2011).
Whitesides et al., "Soft lithography in biology and biochemistry," Annu Rev Biomed Eng. 3:335-73 (2001).
Williams et al., "Amplification of complex gene libraries by emulsion PCR," Nat Methods. 3(7):545-50 (2006).
Wiseman et al., "Major histocompatibility complex genotyping with massively parallel pyrosequencing," Nat Med. 15(11):1322-6 (2009).
Wong et al., "Multiplexed Barcoded CRISPR-Cas9 Screening Enabled By CombiGEM," Proc Natl Acad Sci U S A. 113(9):2544-9 (2016).
Woo et al., "G/C-modified oligodeoxynucleotides with selective complementarity: synthesis and hybridization properties," Nucleic Acids Res. 24(13):2470-5 (1996).
Wood et al., "Targeted genome editing across species using ZFNs and TALENs," Science. 333(6040):307 (2011).
Xi et al., "New library construction method for single-cell genomes," PLoS One. 12(7):e0181163 (2017).
Xia et al., "Soft Lithography," Ann Rev Mat Sci. 28:153-184 (1998).
Xia et al., "Soft Lithography," Angew Chem Int Ed Engl. 37(5):550-575 (1998).
Xiao et al., "Determination of haplotypes from single DNA molecules: a method for single-molecule barcoding," Hum Mutat. 28(9):913-21 (2007).
Yamamoto et al., "Chemical modification of Ce(IV)/EDTA-based artificial restriction DNA cutter for versatile manipulation of double-stranded DNA," Nucleic Acids Res. 35(7):e53 (2007).
Yan et al., "Rapid one-step construction of hairpin RNA," Biochem Biophys Res Commun. 383(4):464-8 (2009).

(56) References Cited

OTHER PUBLICATIONS

Zeng et al., "High-performance single cell genetic analysis using microfluidic emulsion generator arrays," Anal Chem. 82(8):3183-90 (2010).
Zentner et al., "Surveying the epigenomic landscape, one base at a time," Genome Biol. 13(10):250 (2012).
Zhang et al., "Efficient construction of sequence-specific TAL effectors for modulating mammalian transcription," Nat Biotechnol. 29(2):149-53 (2011).
Zhang et al., "Combinatorial marking of cells and organelles with reconstituted fluorescent proteins," Cell. 119(1):137-144 (2004).
Zhang et al., "Degradable disulfide core-cross-linked micelles as a drug delivery system prepared from vinyl functionalized nucleosides via the RAFT process," Biomacromolecules. 9(11):3321-31 (2008).
Zhang et al., "One-step fabrication of supramolecular microcapsules from microfluidic droplets," Science. 335(6069):690-4 (2012).
Zhang et al., "Reconstruction of DNA sequencing by hybridization," Bioinformatics. 19(1):14-21 (2003).
Zhang, Michael Yu, Thesis: "Genomics of inherited bone marrow failure and myelodysplasia," Doctor of Philosophy in Molecular and Cellular Biology, University of Washington, 2015 (142 pages).
Zhao et al., "Preparation of hemoglobin-loaded Nano-sized particles with porous structure as oxygen carriers," Biomaterials. 28(7):1414-1422 (2007).
Zheng et al., "Massively parallel digital transcriptional profiling of single cells," Nat Commun. 8:14049 (2017).
Zheng et al., "Haplotyping germline and cancer genomes with high-throughput linked-read sequencing," Nat Biotechnol. 34(3):303-11 (2016).
Zhou et al., "Development of an enzyme activity screening system for beta-glucosidase-displaying yeasts using calcium alginate microbeads and flow sorting," Appl Microbiol Biotechnol. 84: 375-382 (2009).
Zhu et al., "Hydrogel Droplet Microfluidics for High-Throughput Single Molecule/Cell Analysis," Accounts of Chemical Research. 50(1): 22-31 (2016).
Zhu et al., "Reverse transcriptase template switching: a SMART approach for full-length cDNA library construction," Biotechniques. 30(4):892-7 (2001).
Zhu et al., "Synthesis and self-assembly of highly incompatible polybutadiene-poly(hexafluoropropylene oxide) diblock copolymers," J Polymer Sci Part B: Polymer Phys. 43(24):3685-3694 (2005).
Zimmermann et al., "Microscale production of hybridomas by hypo-osmolar electrofusion," Hum Antibodies Hybridomas. 3(1):14-8 (1992).
Zong et al., "Genome-Wide Detection of Single Nucleotide and Copy Number Variations of a Single Human Cell," Science. 338(6114):1622-1626 (2012).

\* cited by examiner

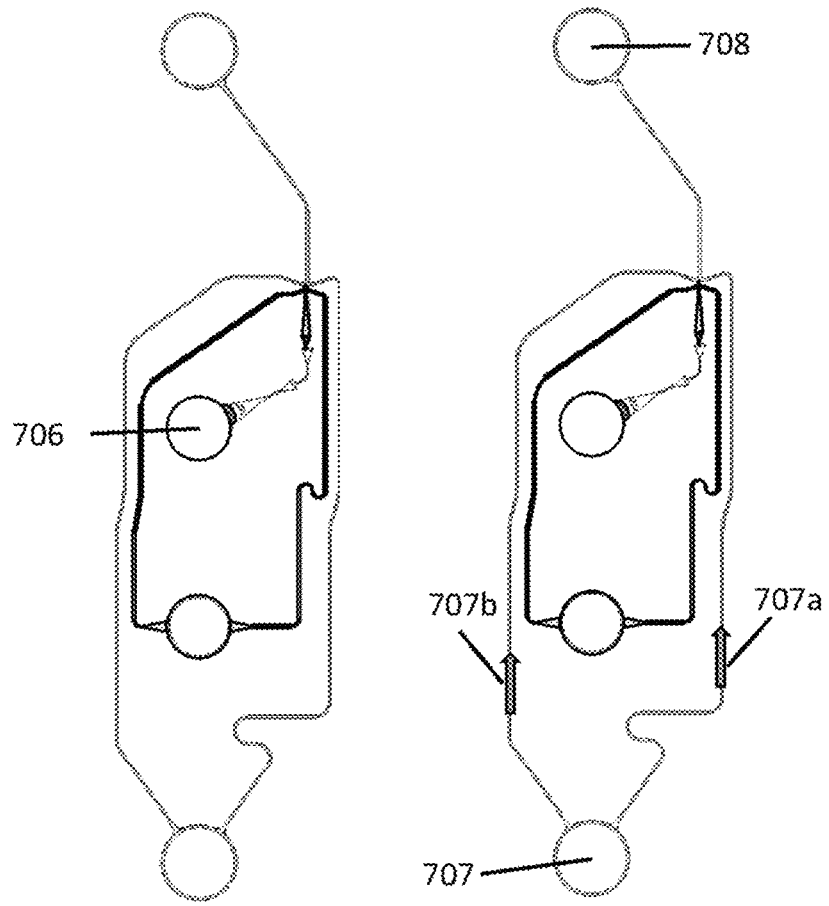
*FIG. 7D*   *FIG. 7E*

MICROFLUIDIC SYSTEMS AND METHODS OF USE

CROSS-REFERENCE

This application claims priority to U.S. Provisional Application No. 62/335,870, filed on May 13, 2016, which is entirely incorporated herein by reference.

BACKGROUND

The field of microfluidics has advanced to the point that it is fulfilling much of its promise to supplant conventional laboratory fluid handling. The ability to precisely control the movement, accession, allocation, and mixing of minute amounts of fluids and subject those fluids to additional processing, analysis, and the like has helped move the field into the mainstream of scientific research, diagnostics, and medical devices.

As research and diagnostic needs become more and more complex, however, there is a need for the field of microfluidics to similarly advance in complexity, requiring a wide range of new functionalities within the microfluidic context. By way of example, microfluidic systems have been used to deliver and combine reagents within microfluidic channels and then perform subsequent processing and/or analytical operations on those reagents, including, e.g., thermal cycling, separations, optical, chemical or electrical detection, and a host of other operations.

In other applications, microfluidic systems have been used to partition small aliquots of aqueous fluids within flowing streams of immiscible fluids, e.g., oils, in order to compartmentalize reactions within those partitions for separate processing, analysis, etc. Specific implementations of these systems have been used to compartmentalize individual nucleic acids in order to perform quantitative amplification and detection reactions (qPCR).

In another implementation, discrete droplets in an emulsion contain both template nucleic acids and beads bearing large numbers of oligonucleotide barcodes, where a given bead will have a constant barcode sequence. The barcode is then used to prime replication of fragments of the template molecules within the particular partition. The replicate fragments created within a given droplet will all share the same barcode sequence, allowing replicate fragments from single long template molecules to be attributed to that longer template. Sequencing of the replicate fragments then provides barcode linked-reads that can be later attributed back to an originating long fragment, provide long range sequence context for shorter sequence reads.

With increasing demands on microfluidic systems, there is a need to add to the microfluidic tools that can be applied to expand their utility. The present disclosure provides a number of such tools and the uses and applications thereof.

SUMMARY

The present disclosure provides novel, improved microfluidic structures, systems and methods for carrying out a variety of different fluid manipulations in microscale channel networks for use in a variety of different applications and methods.

In general a microfluidic channel network is provided, including: a first fluid channel having a first depth dimension; at least a second channel intersecting the first channel at a first intersection; at least a third channel in fluid communication with the first intersection, at least one of the first intersection and the third channel having a depth dimension that is greater than the first depth dimension.

In an aspect, the disclosure provides a microfluidic device. The microfluidic comprises a first fluid channel having a first depth dimension; at least a second channel intersecting the first channel at a first intersection; at least a third channel in fluid communication with the first intersection, at least one of the first intersection and the third channel having a depth dimension that is greater than the first depth dimension. In some embodiments, the microfluidic device further comprises a fourth channel segment, fifth channel segment, sixth channel segment and seventh channel segment intersecting the fourth channel segment at a second intersection, the fifth, sixth and seventh channel segments being coplanar, and where a cross sectional dimension of the seventh channel segment perpendicular to the first plane is larger than the cross sectional dimension of the fourth channel segment perpendicular to the first plane.

In some embodiments, the microfluidic device further comprises one or more steps disposed within one or more of the fourth and seventh channel segments, where the one or more steps provide the cross sectional dimension of the seventh channel segment that is larger than the cross sectional dimension of the fourth channel segment. In some embodiments, the one or more step increases the cross sectional dimension perpendicular to the first plane by at least 1%.

An additional aspect of the disclosure provides a microfluidic system. The microfluidic system comprises a microfluidic channel network comprising first, second, third and fourth channel segments in fluid communication at a first intersection, the first, second, third and fourth channel segments being coplanar, and where a cross sectional dimension of the fourth channel segment perpendicular to the first plane is larger than a cross sectional dimension of the first channel segment perpendicular to the first plane; and a flow control system for directing a first fluid through the first channel segment into the first intersection and into the fourth channel segment, and directing one or more focusing fluids from the second and third channel segments into the first intersection and into the fourth channel segment.

In some embodiments, the microfluidic system comprises a fifth, sixth and seventh channel segment intersecting the fourth channel segment at a second intersection, the fifth, sixth and seventh channel segments being coplanar, and where a cross sectional dimension of the seventh channel segment perpendicular to the first plane is larger than the cross sectional dimension of the fourth channel segment perpendicular to the first plane; and where the flow control system directs the first fluid and focusing fluids and second focusing fluids from the fifth and sixth channel segments into the second intersection. In some embodiments, the first fluid and focusing fluids flow in laminar flow into the fourth channel segment. In some embodiments, the microfluidic system further comprises one or more steps disposed within one or more of the channel segments and providing the larger cross sectional dimensions of the channel segments.

In some embodiments, the one or more step increases the cross sectional dimension perpendicular to the first plane by at least about 1%, at least about 5%, at least about 10%, at least about 20%, at least about 30%, at least about 40%, at least about 50% and least about 100%.

In another aspect, this disclosure provides a microfluidic system. The microfluidic system comprises first, second and third channel segments in fluid communication at a first intersection, the first, second, and third channel segments being coplanar, and where a cross sectional dimension of the third channel segment perpendicular to the first plane is larger than a cross sectional dimension of the first channel segment perpendicular to the first plane; and a flow control system for directing a first fluid through the first channel segment into the first intersection and into the fourth channel segment, and directing a second fluid from the second channel segment into the first intersection and into the third channel segment.

In some embodiments, the microfluidic system further comprises a fifth, sixth and seventh channel segment intersecting the fourth channel segment at a second intersection, the fifth, sixth and seventh channel segments being coplanar, and where a cross sectional dimension of the seventh channel segment perpendicular to the first plane is larger than the cross sectional dimension of the fourth channel segment perpendicular to the first plane; and where the flow control system directs the first fluid and focusing fluids and second focusing fluids from the fifth and sixth channel segments into the second intersection. In some embodiments, the first fluid and focusing fluids flow in laminar flow into the fourth channel segment.

In another aspect, the present disclosure provides a microfluidic system. The microfluidic system comprises a first channel segment fluidly connecting a source of disruptable particles, with a first droplet forming junction, the first channel segment comprising a constricted region proximal to the droplet forming junction; and a flow control system for driving the disruptable particles through the constricted region, where the constricted region comprises a cross sectional dimension reduced sufficiently to induce disruption of the disruptable particles driven through the constricted region, and for flowing disrupted particles into the droplet formation junction, whereby at last a portion of the disrupted particles or the contents thereof are encapsulated into one or more droplets.

In some embodiments, the microfluidic system further comprises a second channel segment, a third channel segment and a fourth channel segment in fluid communication with the first channel segment, where the second channel segment, third channel segment and fourth channel segment facilitate formation of one or more droplets at the droplet forming junction.

In some embodiments, the microfluidic system further comprises a fifth, sixth and seventh channel segment intersecting the fourth channel segment at a second intersection, the fifth, sixth and seventh channel segments being coplanar, and where a cross sectional dimension of the seventh channel segment perpendicular to the first plane is larger than the cross sectional dimension of the fourth channel segment perpendicular to the first plane; and where the flow control system directs the first fluid and focusing fluids and second focusing fluids from the fifth and sixth channel segments into the second intersection. In some embodiments, the first fluid and focusing fluids flow in laminar flow into the fourth channel segment.

In some embodiments, the microfluidic system comprises the constricted region positioned at a distance of fewer than 100 microns, fewer than 50 microns, fewer than 20 microns, fewer than 10 microns or fewer than 5 microns away from the droplet formation junction.

In some embodiments, the present disclosure provides a method of co-partitioning particles using the microfluidic system comprising providing one or more first particle and disrupting the particle by passage through the constriction; providing one or more second particle; and co-partitioning the first and second particle. In some embodiments, the first particle is one or more cells and the second particle is one or more bead. In some embodiments, the first particle is a single cell and the second particle is a single bead. In some embodiments, the bead is a gel bead. In some embodiments, the microfluidic system may further comprise co-partitioning a barcode. In some cases, the barcode is an oligonucleotide. In some cases, the oligonucleotide is a plurality of oligonucleotides having the same sequence. In some embodiments, the method of co-partitioning particles may further comprise providing a lysing agent. In some cases, the method of co-partitioning particles is performed without addition of a lysing agent.

In another aspect, the present disclosure provides a method for controlling filing of a microfluidic network. The method for controlling the filling of a microfluidic network comprises providing a microfluidic channel network comprising a first channel segment and a second channel segment intersecting the first channel segment at a first junction; providing a first fluid in the second channel segment up to the first junction, where capillary flow of the first fluid is interrupted at the first junction; providing a second fluid in the first channel segment, where the second fluid is capable of controlling filling of the microfluidic channel network by releasing the interrupted flow of the first fluid into the microfluidic channel network; and releasing the interrupted flow of the first fluid into the microfluidic channel network.

Some embodiments may provide the method for controlling the filling of a microfluidic network where the first channel segment comprises curved pinning points where the first channel segment meets the first junction. In some cases, the curved pinning points are configured and arranged to provide the interruption of capillary flow of the first fluid. In some embodiments, the method for controlling the filling of a microfluidic network is provided where the microfluidic channel network further comprises a third channel segment at the first junction, where the first fluid and second fluids flow in laminar flow into the third channel segment.

In some embodiments, the second fluid comprises a surfactant. In some embodiments, the surfactant concentration supports release of the interrupted capillary flow of the first fluid upon mixing of the first fluid and the second fluid.

In some embodiments, the microfluidic channel network further comprises one or more additional channel segments intersecting the third channel segment at a second junction, and where the released capillary flow of the first fluid is interrupted at the second junction. In some embodiments, the interruption of capillary flow of the first and second fluids at the second junction is the result of lower surfactant concentration in the mixed first fluid and second fluid. In some embodiments, the method for controlling the filling of a microfluidic network comprises the microfluidic channel network which further comprises a channel expansion feature arranged and configured to control the rate of flow of the first fluid into the microfluidic channel network. In some embodiments, the rate of flow of the first fluid is controlled to be reduced.

In another aspect, the present disclosure provides a method for controlling filing of a microfluidic network. The method for controlling the filling of a microfluidic network comprises providing a microfluidic channel network comprising a first channel segment and a second channel segment intersecting the first channel segment at a first junction; providing a first fluid in the first channel segment up to the first junction, where capillary flow of the first fluid is interrupted at the first junction; providing a second fluid in the second channel segment up to the first junction, where capillary flow of the second fluid is interrupted at the first junction; and providing pressure to both the first and second channel segments to control filling of the microfluidic channel network by releasing the interrupted flow of the first and second fluids into the microfluidic channel network.

In some embodiments, the method for controlling the filling of a microfluidic is where the first channel segment comprises a first curved pinning point and the second channel segment comprises a second curved pinning point where the first and second channel segments meet the first junction. In some cases, the curved pinning points are configured and arranged to provide the interruption of capillary flow of the first and second fluids. In some cases, the first and second curved pinning points each comprise a step feature. In some cases, the step features are configured and arranged to provide a smaller depth at the first junction compared to the depth of the first and second channel segments.

In some embodiments, the microfluidic channel network further comprises a third channel segment at the first junction. In some embodiments, microfluidic channel network further comprises one or more additional channel segments intersecting the third channel segment at a second junction, and where the released flow of the first and second fluids is interrupted at the second junction. In some cases, the method for controlling the filling of a microfluidic network comprises a microfluidic system network further comprising a channel expansion feature arranged and configured to control the rate of flow of the first fluid. In some cases, the rate of flow of the first fluid is reduced.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIGS. 7A-E shows an example system for generating droplets comprising beads and cell beads.

DETAILED DESCRIPTION

Figure 1:
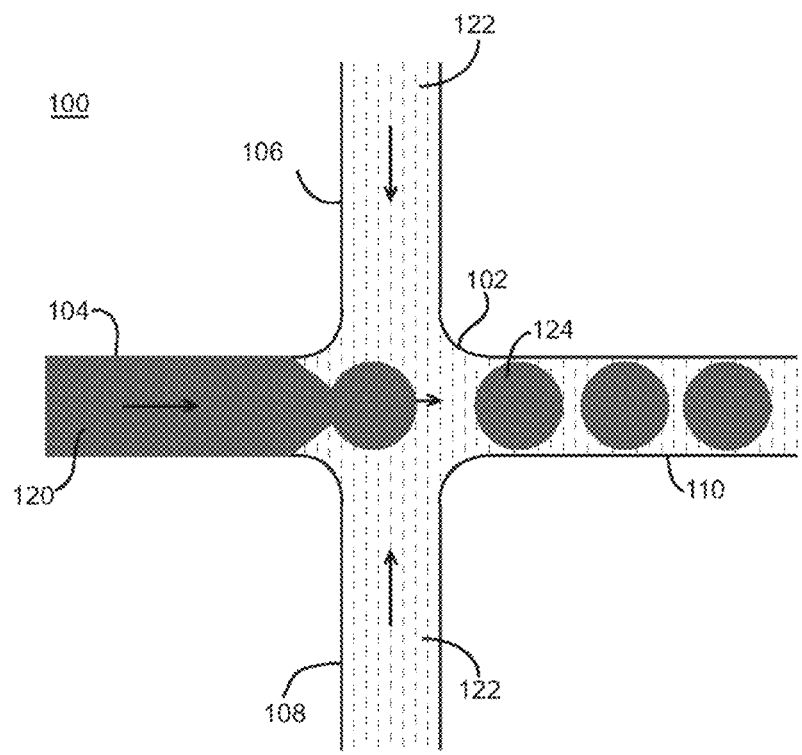
FIG. 1 is an overview schematic illustration of a droplet formation microfluidic channel structure.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "barcode," as used herein, generally refers to a label, or identifier, that conveys or is capable of conveying information about an analyte. A barcode can be part of an analyte. A barcode can be a tag attached to an analyte (e.g., nucleic acid molecule) or a combination of the tag in addition to an endogenous characteristic of the analyte (e.g., size of the analyte or end sequence(s)). A barcode may be unique. Barcodes can have a variety of different formats. For example, barcodes can include: polynucleotide barcodes; random nucleic acid and/or amino acid sequences; and synthetic nucleic acid and/or amino acid sequences. A barcode can be attached to an analyte in a reversible or irreversible manner. A barcode can be added to, for example, a fragment of a deoxyribonucleic acid (DNA) or ribonucleic acid (RNA) sample before, during, and/or after sequencing of the sample. Barcodes can allow for identification and/or quantification of individual sequencing-reads in real time.

The term "subject," as used herein, generally refers to an animal, such as a mammal (e.g., human) or avian (e.g., bird), or other organism, such as a plant. The subject can be a vertebrate, a mammal, a mouse, a primate, a simian or a human. Animals may include, but are not limited to, farm animals, sport animals, and pets. A subject can be a healthy or asymptomatic individual, an individual that has or is suspected of having a disease (e.g., cancer) or a predisposition to the disease, or an individual that is in need of therapy or suspected of needing therapy. A subject can be a patient.

The term "genome," as used herein, generally refers to genomic information from a subject, which may be, for example, at least a portion or an entirety of a subject's hereditary information. A genome can be encoded either in DNA or in RNA. A genome can comprise coding regions that code for proteins as well as non-coding regions. A genome can include the sequence of all chromosomes together in an organism. For example, the human genome has a total of 46 chromosomes. The sequence of all of these together may constitute a human genome.

The terms "adaptor(s)", "adapter(s)" and "tag(s)" may be used synonymously. An adaptor or tag can be coupled to a polynucleotide sequence to be "tagged" by any approach including ligation, hybridization, or other approaches.

The term "sequencing," as used herein, generally refers to methods and technologies for determining the sequence of nucleotide bases in one or more polynucleotides. The polynucleotides can be, for example, deoxyribonucleic acid (DNA) or ribonucleic acid (RNA), including variants or derivatives thereof (e.g., single stranded DNA). Sequencing can be performed by various systems currently available, such as, without limitation, a sequencing system by Illumina, Pacific Biosciences, Oxford Nanopore, or Life Technologies (Ion Torrent). As an alternative, sequencing may be performed using nucleic acid amplification, polymerase chain reaction (PCR) (e.g., digital PCR, quantitative PCR, or real time PCR) or isothermal amplification. Such devices may provide a plurality of raw genetic data corresponding to the genetic information of a subject (e.g., human), as generated by the device from a sample provided by the subject. In some situations, systems and methods provided herein may be used with proteomic information.

The term "bead," as used herein, generally refers to a particle. The bead may be a solid or semi-solid particle. The bead may be a gel bead. The bead may be formed of a polymeric material. The bead may be magnetic or non-magnetic.

The term "sample," as used herein, generally refers to a biological sample of a subject. The biological sample may be a nucleic acid sample or protein sample. The biological sample may be derived from another sample. The sample may be a tissue sample, such as a biopsy, core biopsy, needle aspirate, or fine needle aspirate. The sample may be a fluid sample, such as a blood sample, urine sample, or saliva sample. The sample may be a skin sample. The sample may be a cheek swab. The sample may be a plasma or serum sample. The sample may be a cell-free or cell free sample. A cell-free sample may include extracellular polynucleotides. Extracellular polynucleotides may be isolated from a bodily sample that may be selected from the group consisting of blood, plasma, serum, urine, saliva, mucosal excretions, sputum, stool and tears.

The term "biological particle," as used herein, generally refers to a discrete biological system derived from a biological sample. The biological particle may be a virus. The biological particle may be a cell or derivative of a cell. The biological particle may be an organelle. The biological particle may be a rare cell from a population of cells. The biological particle may be any type of cell, including without limitation prokaryotic cells, eukaryotic cells, bacterial, fungal, plant, mammalian, or other animal cell types, mycoplasmas, normal tissue cells, tumor cells, or any other cell type, whether derived from single cell or multicellular organisms. The biological particle may be obtained from a tissue of a subject. Biological particles may be disruptable particles.

The biological particle may be a hardened cell. Such hardened cell may or may not include a cell wall or cell membrane. The biological particle may include one or more constituents of a call, but may not include other constituents of the cell. A cell may be a live cell. The live cell may be capable of being cultured, for example, being cultured when enclosed in a gel or polymer matrix, or cultured when comprising a gel or polymer matrix.

The term "macromolecular constituent," as used herein, generally refers to a macromolecule contained within a biological particle. The macromolecular constituent may comprise a nucleic acid. The macromolecular constituent may comprise deoxyribonucleic acid (DNA). The macromolecular constituent may comprise ribonucleic acid (RNA). The macromolecular constituent may comprise a protein. The macromolecular constituent may comprise a peptide. The macromolecular constituent may comprise a polypeptide.

The term "molecular tag," as used herein, generally refers to a molecule capable of binding to a macromolecular constituent. The molecular tag may bind to the macromolecular constituent with high affinity. The molecular tag may bind to the macromolecular constituent with high specificity. The molecular tag may comprise a nucleotide sequence. The molecular tag may comprise an oligonucleotide or polypeptide sequence. The molecular tag may comprise a DNA aptamer. The molecular tag may be or comprise a primer. The molecular tag may be or comprise a protein. The molecular tag may comprise a polypeptide. The molecular tag may be a barcode.

The efficiency of many single cell applications can increase by improving cell throughput. For example, this can be achieved by sorting a plurality of droplets that may or may not contain cells and/or particles therein to collect only the droplets that contain the cells and/or particles therein. The isolated population of droplets that contain the cells and/or particles therein can then be subject to further applications, such as nucleic acid amplification and/or sequencing applications.

Microfluidic Structures, Systems and Methods for Droplet Generation

In an aspect, the present disclosure provides a microfluidic channel network. The microfluidic channel network may be used for generating droplets. The droplets may include biological samples and reagents necessary for processing the biological samples. In some examples, the droplets include beads comprising barcodes and biological particles comprising the biological samples, such as, for example, DNA and/or RNA. The biological particles may be cells comprising or enclosed in a gel or polymer matrix.

The microfluidic channel network may include a first fluid channel having a first depth dimension, at least a second channel intersecting the first channel at a first intersection, and at least a third channel in fluid communication with the first intersection. At least one of the first intersection and the third channel may have a depth dimension that is greater than the first depth dimension.

The microfluidic channel network may further comprise fourth channel segments, fifth channel segments, sixth channel segments and seventh channel segments intersecting the fourth channel segment at a second intersection. The fourth, fifth, sixth and seventh channel segments may be coplanar. A cross sectional dimension of the seventh channel segment perpendicular to the first plane may be larger than the cross sectional dimension of the fourth channel segment perpendicular to the first plane.

The microfluidic channel network may further comprise one or more steps disposed within one or more of the channel segments. The one or more steps may provide larger cross sectional dimensions of the channels. The one or more steps may increase the cross sectional dimension perpendicular to the first plane by at least about 1%, at least about 5%, at least about 10%, at least about 20%, at least about 30%, at least about 40%, at least about 50%, or at least about 100%. Such increase may be a gradual increase or a steep (or step) increase.

In another aspect, microfluidic system comprises a microfluidic channel network comprising first, second, third and fourth channel segments in fluid communication at a first intersection. The first, second, third and fourth channel segments may be coplanar. A cross sectional dimension of the fourth channel segment perpendicular to the first plane may be larger than a cross sectional dimension of the first channel segment perpendicular to the first plane.

The system may further comprise a flow control system for directing a first fluid through the first channel segment into the first intersection and into the fourth channel segment, and directing one or more focusing fluids from the second and third channel segments into the first intersection and into the fourth channel segment. A focusing fluid may be another aqueous stream or may be non-aqueous (e.g., oil). The flow control system may be or include one or more pumps for providing a negative pressure (e.g., pressure drop) to subject the first fluid to flow. Alternatively, the flow control system may be or include one or more compressors for providing positive pressure to subject a fluid (e.g., the first fluid) to flow.

At least a subset or all of the first, second, third and fourth channel segments may be coplanar (i.e., oriented along the same plane). As an alternative, at least a subset or all of the first, second, third and fourth channel segments may not be coplanar.

The microfluidic system may further comprise a fifth, sixth and seventh channel segment intersecting the fourth channel segment at a second intersection. Such channel segments may be channels or portions of channels. The fifth, sixth and seventh channel segments may be coplanar. A cross sectional dimension of the seventh channel segment perpendicular to the first plane may be larger than the cross sectional dimension of the fourth channel segment perpendicular to the first plane.

The microfluidic system may further comprise a flow control system that directs the first fluid and one or more focusing fluids and one or more additional focusing fluids from the fifth and sixth channel segments into the second intersection. The one or more additional focusing fluids may be the same or different from the one or more focusing fluids.

The first fluid and focusing fluids may flow in laminar flow into the fourth channel segment. As an alternative, the first fluid and focusing fluid may flow in turbulent flow into the fourth channel segment.

In another aspect, the microfluidic system may comprise a microfluidic channel network comprising first, second and third channel segments in fluid communication at a first intersection. The first, second, and third channel segments may be coplanar. A cross sectional dimension of the third channel segment perpendicular to the first plane may be larger than a cross sectional dimension of the first channel segment perpendicular to the first plane.

The system may further comprise a flow control system for directing a first fluid through the first channel segment into the first intersection and into the fourth channel segment, and directing a second fluid from the second channel segment into the first intersection and into the third channel segment. The flow control system may be or include one or more pumps for providing a negative pressure (e.g., pressure drop) to subject the first fluid to flow. Alternatively, the flow control system may be or include one or more compressors for providing positive pressure to subject a fluid (e.g., the first fluid) to flow. The microfluidic system may further comprise a fifth, sixth and seventh channel segment intersecting the fourth channel segment at a second intersection. The fifth, sixth and seventh channel segments may be coplanar. A cross sectional dimension of the seventh channel segment perpendicular to the first plane may be larger than the cross sectional dimension of the fourth channel segment perpendicular to the first plane.

The microfluidic system may further comprise a flow control system which directs the first fluid and focusing fluids and second focusing fluids from the fifth and sixth channel segments into the second intersection. The first fluid and focusing fluids may flow in laminar flow into the fourth channel segment.

The microfluidic system may further comprise a fifth, sixth and seventh channel segment intersecting the fourth channel segment at a second intersection, the fifth, sixth and seventh channel segments being coplanar and wherein a cross sectional dimension of the seventh channel segment perpendicular to the first plane is larger than the cross sectional dimension of the fourth channel segment perpendicular to the first plane; and wherein the flow control system directs the first fluid and focusing fluids and second focusing fluids from the fifth and sixth channel segments into the second intersection.

The first fluid and focusing fluids may flow in laminar flow into the fourth channel segment. Alternatively, the first fluid and focusing fluids may flow in turbulent flow into the fourth channel segment.

The microfluidic channel network may further comprise one or more steps disposed within one or more of the channel segments. The one or more steps may provide larger cross sectional dimensions of the channel segments. The one or more steps may increase the cross sectional dimension perpendicular to the first plane by at least about 1%, at least about 5%, at least about 10%, at least about 20%, at least about 30%, at least about 40%, at least about 50%, or at least about 100%. Such increase may be a gradual increase or a steep (or step) increase.

Reference will now be made to the figures, wherein like numerals refer to like parts throughout. It will be appreciated that the figures and features therein are not necessarily drawn to scale.

In a first example, provided are microfluidic channel networks and systems that provide enhanced partitioning of fluids, e.g., aqueous fluids partitioned as droplets in immiscible oils. For example, in some cases, channel networks may be provided that include a droplet generation junction at the intersection of a first aqueous fluid carrying channel segment and a first partitioning fluid, e.g., oil, carrying channel segment. Typically, aqueous droplets may be formed at the intersection as the aqueous fluid is dripped into the flowing oil stream at the intersection, forming droplets of aqueous fluid within the oil stream. FIG. 1 provides a simplified illustration of a droplet generation junction in which droplets of aqueous fluids are dripped into a non-aqueous fluid stream. As shown, a microfluidic channel network 100 includes a droplet generation junction 102 that may be coupled to an aqueous fluid channel segment 104. Two partitioning fluid inlet channels, 106 and 108, are also provided in fluid communication with the droplet generation junction 102. An outlet channel segment 110 may also be coupled to the droplet generation junction into which the droplets may be dripped into the non-aqueous partitioning fluid.

In operation (and as also illustrated in FIG. 1), an aqueous fluid 120 may be flowed into the droplet generation junction 102 from channel segment 104, while simultaneous streams of partitioning fluid 122 enter the junction from their respective channels 106 and 108. The focusing flow of the partitioning fluid constricts the aqueous fluid, which then drips off as droplets 124 into the flowing stream of partitioning fluid as it travels along the outlet channel segment 110. In some cases a point of constriction may be provided in the droplet generation junction in order to facilitate the dripping mechanism of droplet generation by accelerating the fluid flow through the junction.

Droplets of similar or substantially the same dimensions, e.g., cross section and/or volume, may be repeatedly formed. A number of factors can influence how such droplets are formed, including flow rates of the fluids that are interacting at the droplet generation junction, dimensions of the channels flowing into and out of the intersection, fluid characteristics of the fluids, and interactions between the fluids and the walls of the channels at or near the junction and in the downstream channels.

While certain immiscible phase emulsion arrangements like water in oil are discussed in respect to droplet formation herein, other emulsion arrangements in relation to the systems and methods described herein are envisioned, including but not limited to arrangements of immiscible phases such as air-in-water, oil-in-water, oil-in-water-in-oil, or the likes.

Improved Flow Channel Structures

In some cases, including as illustrated above, droplets being formed at a droplet generation junction have been focused away from the side walls of the channels in which they are flowing by simultaneously flowing the non-aqueous partitioning fluid, e.g., oil, from opposing side channels, e.g., channel segments 106 and 108 in FIG. 1. While this may maintain a barrier stream of fluid between droplets and the side walls of the channel, because these microfluidic systems are fabricated in two dimensional planes, focusing flow tends to be only provided in those two dimensions. This leaves the possibility of droplets making contact with the upper and/or lower walls of a channel segment, with a possible result of a fluid contaminating the surface of the channels, and/or other adverse effects on droplet size and uniformity. Such contamination can be particularly problematic where partitions are used to contain different reagents or sample components, and cross-contamination may lead to aberrant results from downstream analyses. This potential problem is compounded where multiple reagents are combined and partitioned in these systems.

As described herein, in some cases, the droplet generation junction, e.g., FIG. 1 droplet generation junction 102, and/or the downstream channel segment coupled to the droplet generation junction, e.g., channel segment 110, are provided with a depth dimension that is greater than the depth dimension of the channel segments leading into the junction, e.g., channel segments 104, 106 and 108. It is envisioned that channels as shown in the figures presented need not be limited to uniform dimensions. Different height, width and length dimensions of the various channels described herein are envisioned. The dimensions may be uniform or different between channels or in respect to different portions of the same channel.

Figure 2A:
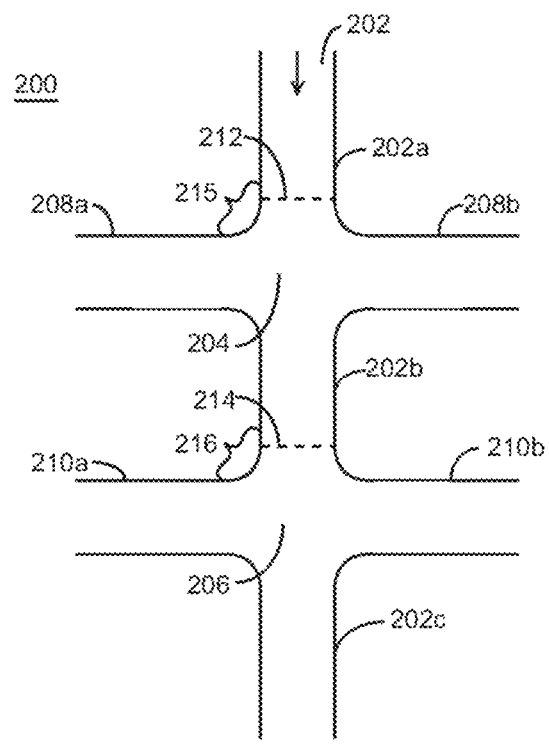
FIG. 2A is an overview schematic illustration of a microfluidic channel structure including steps and multiple junctions.
Figure 2B:
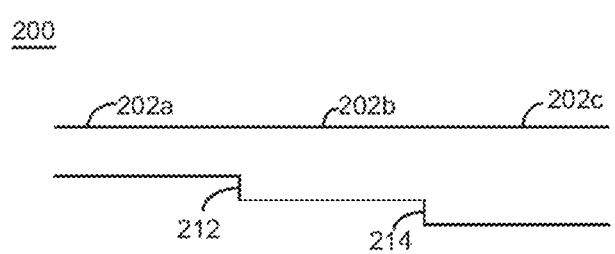
FIG. 2B is a side view schematic illustration of the structure in FIG. 2A.

FIGS. 2A and 2B schematically illustrate an example of a microfluidic channel system that employs such channel structures. As shown in FIG. 2A (top view), a channel network 200 may include a main flow direction channel 202 made up of three distinct channel segments 202a, 202b and 202c, that may be divided by intersections 204 and 206. Intersection 204 may join channel segments 202a and 202b with side channel segments 208a and 208b. Likewise, intersection 206 may join channel segments 202b and 202c with side channel segments 210a and 210b. FIG. 2B is a profile view of the system.

Figure 2C:
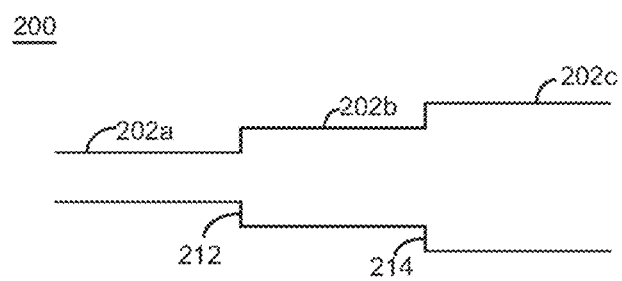
FIG. 2C is a side view schematic illustration of an alternative configuration of the structure in FIG. 2A.

FIG. 2C schematically illustrates a profile view of an additional example of a microfluidic channel system employing channel structures as described for FIGS. 2A and 2B.

As shown in FIGS. 2A-C, a first step structure 212 may be provided at the point at which channel segment 202a connects with intersection 204. Likewise a second step structure 214 may be provided at the point that channel segment 202b connects with intersection 206. The step structure may result in an increase in depth in moving from each of channel segments 202a and 202b into intersections 204 and 206, respectively. This is schematically illustrated in FIGS. 2B and 2C, which provide profile views of the channel network illustrating the change in depth dimension as channel segment 202a expands into segment 202b and 202c at intersections 204 and 206, respectively.

The step structures described herein may exist at one or both of the upper and/or lower channel walls, and may result in an increase in the depth dimension of the channel, e.g., the dimension perpendicular to the main plane of a device, of at least about 1%, at least about 5%, at least about 10%, at least about 20%, at least about 30%, at least about 40%, at least about 50%, and in some cases by at least about 100% or more.

While steps can be provided as structural pinning features, it is envisioned that the same or similar effects can be achieved using a material-based "step", for example, by patterning sections of channels using a variety of compounds, compositions or even texture. For example, in a channel that has been patterned chemically to form well-defined sections of hydrophilic and hydrophobic surface conditions, an aqueous fluid flowing across a hydrophilic section will pin at an interface with a hydrophobic section.

Figure 3A:
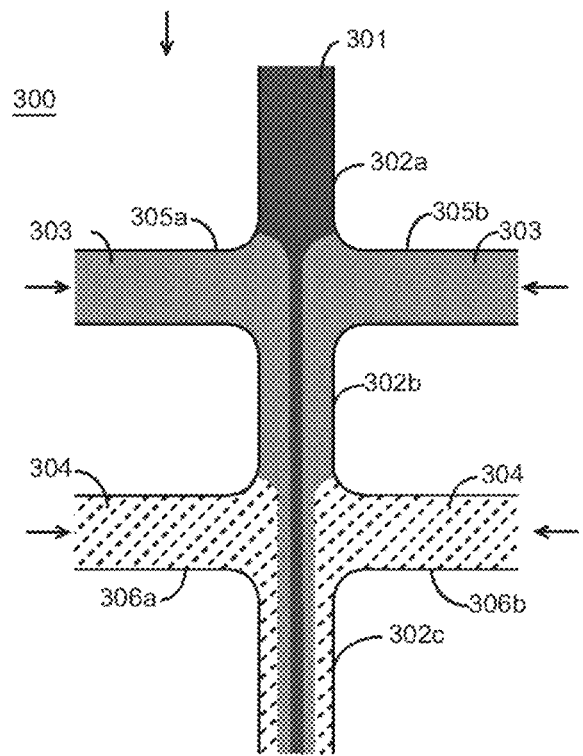
FIG. 3A is an overview schematic illustration showing flow of fluids in the structure of FIG. 2A.
Figure 3B:
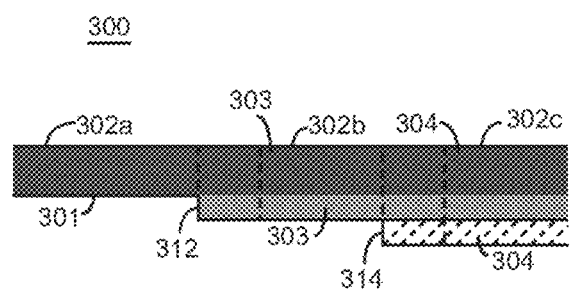
FIG. 3B is a side view schematic illustration showing fluid flow in the structure of FIG. 3A.

FIGS. 3A and 3B give an example of the FIGS. 2A and 2B channel networks in operation. Fluids introduced into a given intersection, e.g., from channel 302a into intersection 306, may remain separated from the lower channel walls by virtue of the presence of the fluid 303 brought into the intersection from channel segments 305a and 305b. FIG. 3A shows an example of an aqueous fluid in 303 being used as a focusing fluid to narrow the stream of the fluid in 301. Likewise, the combined fluids flowing into channel segment 302b may be displaced from the lower channel wall by fluids flowed into intersection 308 by the fluid 304 brought in from channel segments 306a and 306b. Although described in some cases in terms of the intersections being droplet generation junctions, such step structures may also be useful in maintaining laminar flow separation of combined fluids that are not at a droplet generation junction, but merely at a mixing or fluid combination intersection. For example, two or more different aqueous fluids may be brought together at intersection 308 via channel segments 302a-c, 305a-b and 306a-b. FIG. 3B details the flow of fluids 301, 303 and 304 in this fashion. By virtue of the presence of the step structures 312 and 314 indicated in FIG. 3B, any adverse interactions between one or more of the aqueous fluids and side walls, e.g., adsorption of sample components, may be reduced or avoided as the focusing flows may shield such fluids from the side, upper and/or lower channel walls.

As the combined fluid is flowed into intersection 308, immiscible partitioning fluid may be introduced from each of side channels 304a and 304b, to further surround the combined fluid stream. This is illustrated in a side view in FIG. 3B, where the partitioning fluid is illustrated as the white space around the cell fluid and lysis agent. As will be appreciated, at this intersection, the fluids may be partitioned into droplets of cell suspension combined with lysis agent, surrounded by the partitioning fluid. By incorporating the step, as well as the focusing function of the fluids from the side channels, one may minimize the level of contamination of the side walls from the first fluid introduced, e.g., the lysis agent/surfactant. As will be appreciated, the ability to avoid surface contamination with other surfactants, e.g., that one is using as a lysis agent as described in greater detail herein, is of significant importance in droplet based partitioning systems, which rely on specific surfactant compositions to ensure proper partitioning and subsequent stability of aqueous droplets in oil based fluids. Likewise it will be appreciated that other side wall contaminants such as polymers and lipids may be avoided.

Co-Partitioning Channel Networks

In another aspect, microfluidic system is described. The microfluidic system may comprise a first channel segment fluidly connecting a source of disruptable particles, with a first droplet forming junction. The disruptable particles may be a single cell or multiple cells from a biological specimen.

The first channel segment may comprise a constricted region proximal to the droplet forming junction. A flow control system may further drive the disruptable particles through the constricted region. The constricted region may comprise a cross sectional dimension reduced sufficiently to induce disruption of the disruptable particles driven through the constricted region. The disruptable particles may then physically become disrupted, damaged or lysed upon passage through the channel, resulting in a damaged or lysed cell. The flow control system may then be used to flow the disrupted particles into the droplet formation junction, whereby a portion of the disrupted particles or the contents thereof may be encapsulated into one or more droplets.

The microfluidic system may further comprise a second channel segment, a third channel segment and a fourth channel segment in fluid communication with the first channel segment. The second channel segment, third channel segment and fourth channel segment may facilitate the formation of one or more droplets at the droplet forming junction.

The microfluidic system may further comprise fifth channel segments, sixth channel segments and seventh channel segments intersecting the fourth channel segment at a second intersection. The fifth, sixth and seventh channel segments may be coplanar. A cross sectional dimension of the seventh channel segment perpendicular to the first plane may be larger than the cross sectional dimension of the fourth channel segment perpendicular to the first plane. The flow control system may direct the first fluid and focusing fluids and second focusing fluids from the fifth and sixth channel segments into the second intersection.

The first fluid and focusing fluids may flow in laminar flow into the fourth channel segment. As an alternative, the first fluid and focusing fluid may flow in turbulent flow into the fourth channel segment.

The microfluidic system may position the constricted region at a distance fewer than 100 microns, 50 micrometers (microns), 20 microns, 10 microns, 5 microns 1 micron, 0.5 microns, or less away from the droplet formation junction.

In addition, a method of co-partitioning particles is provided using the microfluidic system described above. The method may comprise providing a first particle (e.g., cell from a biological specimen) and disrupting the particle by passaging through the constricted region. The microfluidic system may further provide a second particle (e.g., bead/beads which may contain barcodes and/or other reagents); and co-partitioning the first and second particle in to one/more droplets for further processing of the biological specimen. Alternatively, the first particle may comprise multiple cells. The second particle may also comprise multiple beads to be co-partitioned with the first particle comprising multiple cells.

The microfluidic system may enable co-partitioning the first and the second particle in the microfluidic system, where, the second particle may comprise a gel bead. Additionally, the second particle may comprise a barcode. The barcode may comprise an oligonucleotide. Alternatively, the barcode may comprise a plurality of oligonucleotides having the same sequence. In another embodiment, the first or the second particle may comprise a lysing agent. In yet another embodiment, the method of co-partitioning the first and the second particle may be performed without the addition of a lysing agent.

Figure 4A:
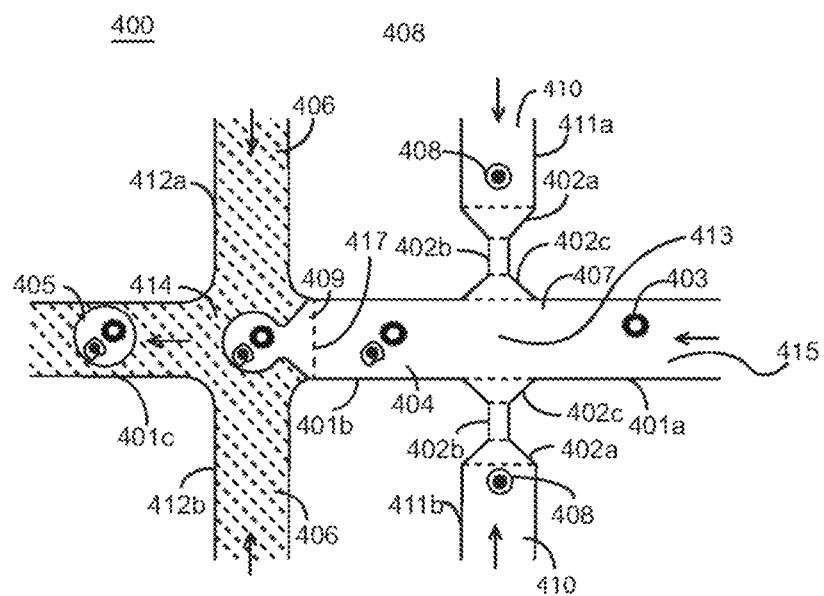
FIG. 4A is an overview schematic illustration of a co-partitioning microfluidic channel network.
Figure 4B:
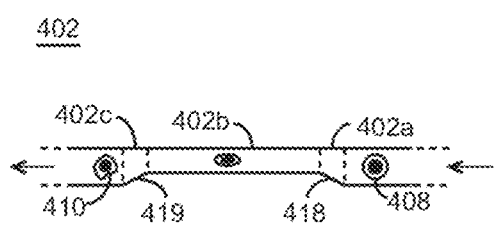
FIG. 4B is a close up schematic illustration detailing a side view of a constriction feature of FIG. 4A.

FIGS. 4A and 4B schematically illustrate an example of an operation in which disruptable particles, e.g., cells, are co-partitioned with other reagents and or particles in an iterative fluid combining step using the channel networks related to those described above, including laminar flow of fluids and use of step features. Exemplary reagents may include, e.g., lysis agents such as an effective concentration of a surfactant and exemplary particles may include, e.g., other cells or beads such as gel beads.

As shown in FIG. 4A, with reference to the microfluidic channel networks illustrated in FIGS. 2A and 3A, a first fluid 415 which can be aqueous, may include a bead 403, may be flowed along channel segment 401a and into intersection 413. Intersection 413 may also be in fluid communication with one or more other channel segment. As illustrated in FIG. 4A, the channel intersecting is a constriction 402 feature comprised of sections 402a-c. As illustrated there may be two channels intersecting channel 401a at intersection 413, but it should be understood that a single or three or more channels may intersect.

The constriction 402 feature is detailed in FIG. 4B. As shown, it may be comprised of a channel 402a having a first depth leading to a ramp or step 418 feature that connects to a channel 402b having a smaller second depth and/or width. Channel 402b may be connected to a second ramp or step 419 feature that connects to a channel 402c having a depth similar or the same as for channel 402a. As shown, disruptable particles, e.g., a cell or cells 408 may be introduced into the constriction 402 feature and physically become disrupted, damaged or lysed upon passage through channel 402b, resulting in a damaged or lysed cell 410.

As shown in FIG. 4A, disruptable particles, e.g., cell or cells 410 may be introduced to constriction feature 402 through channel 411a and 411b in a second fluid 410, which may be aqueous. As fluid 410 and cells 408 encounter the constriction 402, the cell or cells may be damaged or lysed, then mix with aqueous fluid 415 at intersection 413, where in some cases a bead 415 can be associated with the damaged or lysed cell 410. A cell, e.g., a single cell, may be associated with a bead to form a lysed cell-bead complex 404, either at intersection 413 or as passing along channel 401b. Channel 401b connects to one or more additional channels at intersection 414. As shown in FIG. 4A, three channels, 412a, 412b and 401c may connect with channel 401b at intersection 414. As indicated by hash marks, channels 412a and 412b may bring a third partitioning fluid 406 (hash marked) to intersection 414 for interaction with the fluids 415 and 410 surrounding the lysed cell-bead complex 404. As indicated at 409, droplet or partitioning fluid 406 may be immiscible with fluids 415 and 410, creating a partitioned lysed cell-bead complex 405. As shown, the partitioned lysed cell-bead complex 405 may flow along channel 401c for subsequent purposes.

Cell Content Analysis

As noted above, in some cases, microfluidic channel networks are particularly desired for use in analyzing the contents of cells, and particularly for evaluation of the contents of individual cells. In certain cases, an individual cell may be partitioned within a single droplet of aqueous fluid in an immiscible partitioning fluid. By co-partitioning a lysis agent, e.g., as described above, along with the cell, one may disrupt the cell and release its contents into the droplet for subsequent processing and/or analysis within the droplet. For example, as described in co-pending U.S. Patent Application Publication No. 2015/0376609, filed on Jun. 26, 2015, which is entirely incorporated herein by reference, an individual cell may be co-partitioned with a lysis agent and a set of oligonucleotide barcodes, as described above. The lysis agent may then act on the cells to release the contents of the cell into the partition. The co-partitioned barcodes may then be used to tag the nucleic acid contents of the cell as described above. Different barcode sequences may be added to different droplets or partitions within the overall emulsion, such that nucleic acids from a given cell will only be tagged with one barcode, allowing more effective attribution of the barcodes, and their connected nucleic acids, to an originating cell, once those nucleic acids and barcodes are sequenced.

In some cases, as shown in and discussed above for FIGS. 4A and 4B above, it may be desirable to forego the use of a lysis agent, or provide additional efficacy to the lysis step of the overall process through the inclusion of a mechanical lysis structure within the channels of the microfluidic device. However, the same mechanical forces that may result in disruption of a cellular membrane, may also result in disruption of fluid forces (e.g., surface tension) holding a partitioned droplet together. As such, as described herein, the lysis structure may be included proximal to, but upstream from the droplet forming junction at which it is desired to partition the cell contents.

It is worth noting that while the systems and methods disclosed herein are capable of performing cell lysis, even complete cell lysis, it is envisioned and can be understood that modifications to the lysis structures or lysis agent used can result in any desired degree of partial lysis or disruption of the cell, e.g., disruption of a cell membrane. For convenience however, the phrases lysis structure and lysis agent will be used to describe any level of cell disruption.

A particular advantage of the systems and methods disclosed herein includes the ability to lyse a cell, e.g., a single cell, immediately upstream of the droplet generation junction, so one can be more certain that the contents of a given cell will be partitioned within a single droplet (or a small number of droplets). Moreover, because of the laminar flow characteristics of microfluidic systems, one may be reasonably certain that only minimal diffusion of the cellular contents will occur. It is envisioned that minimal diffusion or dispersion of cell contents may be achieved by providing short residence times (the time between lysis and encapsulation for example). In some cases, the lysis structure may be provided within a distance of fewer than 100 microns, fewer than 50 microns, fewer than 20 microns, fewer than 10 microns, fewer than 5 microns away from the droplet generation junction. In other cases, the lysis structure may be provided at a distance that provides for minimal amount of diffusion time for the released contents of a cell between lysis and partitioning within the droplet generation junction at the flow rates used in a given operation. For example, in some cases, this time may be less than about 100 milliseconds (ms), less than about 50 ms, less than about 30 ms, less than about 20 ms, less than about 10 ms, or even less than about 5 ms down to as low as 1 ms, 0.5 ms, 0.1 ms or even less than about 0.01 ms.

In some cases, a lysis structure may include a cross-sectional restricted region of a channel that imparts sufficient shear forces upon a cell or other particle so as to cause its disruption under the conditions being applied, e.g., flow rates, pressures, presence of other lysis reagents, etc. An example of such a structure is illustrated in FIGS. 4A and 4B. As shown, a constricted channel segment 402 through which cells are passed prior to entering into a droplet generation junction, may be provided with a significantly reduced cross section, in at least one dimension, and in some cases, two dimensions. In such cases, transition of flowing streams through such constricted spaces may subject cells within those streams to high shear stresses than can result in lysis of those cells. As noted, this may be accompanied by the presence of other lysis forces, such as lysis agents present in the cell suspension.

In some cases the lysis structure may include a series of constrictions, e.g., at least 2, at least 3, at least 4, at least 5, etc. or more constrictions provided in a series. In other cases the lysis structure may include pillar features arranged in a pathway a cell or cells may traverse and in so doing suffer partial or complete lysis. Combinations of the above lysis structures are also envisioned.

Passive Valving Structures—Aqueous Channels at Intermediate Positions

The present disclosure provides methods for controlling filling of a microfluidic network. A method for controlling filling of a microfluidic channel network may comprise providing a first channel segment and a second channel segment intersecting the first channel segment at a first junction. The first channel segment and second channel segment may be part of a device, such as an integrated device. The device may be a microfluidic device. The device may be a droplet generator. The device may be part of a system. Such system may include a controller for regulating, for example, fluid flow. The system may include one or more pumps and/or one or more compressors (or other actuators) for facilitating fluid flow.

A first fluid may be provided in the second channel segment up to the first junction. In this embodiment the capillary flow of the first fluid may be interrupted at the first junction. A second fluid may also be provided in the first channel segment. The second fluid may be capable of controlling filling of the microfluidic channel network by releasing the interrupted flow of the first fluid into the microfluidic channel network. This may assist in releasing the interrupted flow of the first fluid into the microfluidic channel network.

In some cases, the first channel segment comprises curved or angled pinning points where the first channel segment meets the first junction. Such curved pinning points may be configured and arranged to provide the interruption of capillary flow of the first fluid.

The device may further comprise a third channel segment at the first junction. The first fluid and second fluids may further flow in laminar flow into the third channel segment. Alternatively, the first fluid and second fluids may further flow in turbulent flow in to the third channel.

In some cases, a second fluid comprising a surfactant may be used. The surfactant concentration in the second fluid may be adjusted to support the release of the interrupted capillary flow of the first fluid upon mixing of the first fluid and the second fluid. The interruption of capillary flow of the first and second fluids at the second junction may be the result of a lower surfactant concentration in the mixed first fluid and second fluid. The mixed first and second fluids may be interrupted by either decreased surfactant concentration due to mixing or due to physical pinning of meniscus which may be provided at a step change in channel depth and or channel width.

The microfluidic channel network may further comprise one or more additional channel segments. Such additional channel segments may intersect the third channel segment at a second junction. The released capillary flow of the first fluid may further be interrupted at the second junction.

The device may comprise a microfluidic channel network further comprising a channel expansion feature. This channel expansion feature may be arranged and configured to control the rate of flow of the first fluid into the microfluidic channel network. The channel expansion feature may control the rate of flow of the first fluid. The channel expansion feature may reduce the flow rate of the first fluid. Alternatively, in yet another embodiment, the microfluidic channel expansion may increase the flow rate of the first fluid.

In yet another aspect, a method for controlling filing of a microfluidic network is described. The microfluidic network may comprise providing a microfluidic channel network comprising a first channel segment and a second channel segment intersecting the first channel segment at a first junction. The microfluidic channel network may provide a first fluid in the first channel segment up to the first junction. Capillary flow of the first fluid may be interrupted at the first junction. Additionally, it may provide a second fluid in the second channel segment up to the first junction. Capillary flow of the second fluid may also be interrupted at the first junction. The method may then further include providing pressure to both the first and second channel segments to control the filling of the microfluidic channel network by releasing the interrupted flow of the first and second fluids into the microfluidic channel network.

The microfluidic network may further comprise a first channel segment comprising a first curved pinning point and the second channel segment comprising a second curved pinning point where the first and second channel segments meet the first junction. The curved pinning points in both the first channel segment and the second channel segment may be configured and arranged to provide the interruption of capillary flow of the first and second fluids.

In some cases, the first and second curved pinning points in the first channel segment and the second channel segment respectively may each comprise a step feature. Additionally, the step features may be configured and arranged to provide a smaller depth at the first junction compared to the depth of the first and second channel segments. In some cases, the microfluidic channel network may further comprise a third channel segment at the first junction. These additional channel segments may intersect the third channel segment at a second junction, wherein the released flow of the first and second fluids is interrupted at the second junction.

Some embodiments of this method of controlling the filling of the microfluidic network may further comprise a channel expansion feature. This channel expansion feature may be arranged and configured to control the rate of flow of the first fluid. The channel expansion feature may control the rate of flow of the first fluid. The channel expansion feature may reduce the flow rate of the first fluid. Alternatively, in some cases, the microfluidic channel expansion may increase the flow rate of the first fluid.

As described elsewhere herein, microfluidic channel networks may be used in conjunction with different types of fluids within the same channel network, including different types of aqueous fluids, aqueous and non-aqueous fluids, etc. In such systems, as well as in many other applications of microfluidic systems, it may be desirable to provide stepwise additions of different fluid materials to the channel networks, in order to rely on capillary action and wicking to fill the channels, while only having such filling reach certain portions of the channel network and not others.

In certain cases, microfluidic structures or arrangements may be provided to ensure proper and selective filling of different channel segments. One example of such an arrangement incorporates an intervening passive valving structure disposed between two channel segments in which differential filling is desired. In a simple context, such valving structures may include areas of increased cross sectional dimension disposed at an end of a given channel segment, such that capillary forces can draw fluid into the valving structure. These structures may include step structures that increase the depth of the channel, widened channel regions that increase the lateral cross section of the channels or combinations of these. In some cases, the passive valving may be provided at intersections with connected channel segments, which provide the increased cross sectional area.

Despite the use of these passive valving structures, in many cases, additional measures may be used to prevent fluid wicking beyond a desired point. For example, in certain cases, fluids may be disposed within channel segments that include concentrations of surfactants, e.g., either for partitioning or for use as cell lysis agents. Such surfactant laden fluids can, in some instances, be prone to wicking through microfluidic channel networks despite the presence of passive valves, e.g., by decreasing the contact angle between the fluid and the surface of the channel, resulting in a higher capillary pressure. As such, in using such passive valving structures it may sometimes be desirable to incorporate additional measures to avoid such unintended wicking. In one exemplary approach, an intervening aqueous fluid that may be low in surfactant, e.g., has a higher contact angle than the surfactant laden fluid, may be provided at a passive valving structure. When the surfactant laden fluid reaches the passive valve and adjacent aqueous fluid barrier, the surfactant may be diluted and the contact angle at the interface may be increased such that the passive valve structure functions as desired, preventing further wicking into the channels of the device.

FIG. 5 is a schematic illustration of an approach to such valving structures, useful, for example, in the context of a droplet generating microfluidic device in which aqueous fluids are partitioned into non-aqueous fluids as an emulsion. As noted, in many cases, these systems may include concentrations of surfactants mixed into one or both of the aqueous and non-aqueous fluids within the channel network in order to facilitate partitioning of fluids within the channel network, e.g., at a droplet generation junction or the like.

In some cases, additional elements may be incorporated into these intersecting channel segments to allow for segmented introduction of the differing fluids into the device. In some cases, two channel segments in which different filling is desired may be joined at an intersection with a third channel segment. The third channel segment may be first filled with a fluid that will provide a break in the capillary action on one or more fluids introduced into the two other channel segments. FIG. 5 provides one example of such a valving arrangement. As will be appreciated, one, two, three, four or more such structures may be provided within a microfluidic device in order to facilitate differential fluid introduction. Furthermore, the additional structures may be arranged at a variety of angles and provided in staggered or other configurations.

In providing a droplet generation junction within a microfluidic channel network, e.g., as described above, it is generally desirable to provide the non-aqueous fluids in the downstream channels without them wicking into the channels that are to deliver aqueous fluids into the droplet generation junction. Due to the high wettability of non-aqueous fluids on material surfaces, the only way to prevent contamination of the upstream, aqueous fluid-delivering channels with non-aqueous fluid is to fill the desired channels with the aqueous fluids before introducing the non-aqueous fluid. Hydrostatic pressure may then be used to passively balance or counteract the capillary pressure associated with an oil-aqueous or oil-air meniscus.

Figure 5A:
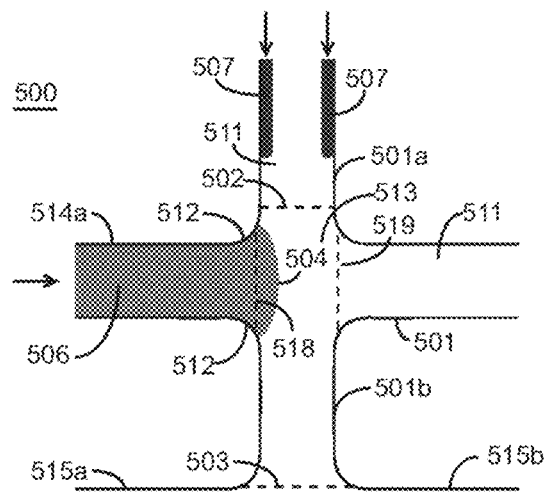
FIGS. 5A-D are schematic illustrations of a passive valving microfluidic channel structure in sequential stages of operation.

FIGS. 5A-D illustrate an exemplary passive valving structure arrangement and the process of operating a passive valve. FIG. 5A shows an initial resting state of the passive valving in structure 500. Fluid 506, which can be a surfactant poor aqueous fluid, is shown within channel 514a and may be pinned at intersection 513, which is filled with air. Pinning point 512 serves to hold the fluid in a primed fluid state shown as menisci 504 against air 511. A second fluid 507, which may be surfactant-rich, is shown entering channel 501a and approaching the primed valve fluid 504. It should be understood that surfactant-rich fluid traveling quickly through the corners/gutters of the channels may be useful. In particular, the second fluid 507 "tendrils" of the surfactant-rich fluid move faster than the bulk surfactant-rich fluid. This feature may control the dilution of surfactant-rich with surfactant-free, and thus the stability of the pinning of the combined fluid at pinning point 513 (higher stability may be achieved at higher dilution). The shape of the cross-section is a useful design feature for controlling the speed of the second fluid 507 "tendrils", which can be faster than the source fluid within the channel. For example, the shape may be polygonal, trapezoidal, rectangular, square, etc. (not shown).

The pinning point 512 may be configured and arranged, e.g., as curved corners at intersection 513. The radii of curvature may be adjusted to optimize the action of pinning point 512 as desired, the action being in a range from slight to strong restraint of fluid 506 at pinning points 512. Physical or chemical steps may be included within channels or at intersections of channels as required to provide and enable pinning points as described herein. For example, as illustrated in FIGS. 5A-D, steps 502, 503, 518 and/or 519 can be included.

Figure 5B:
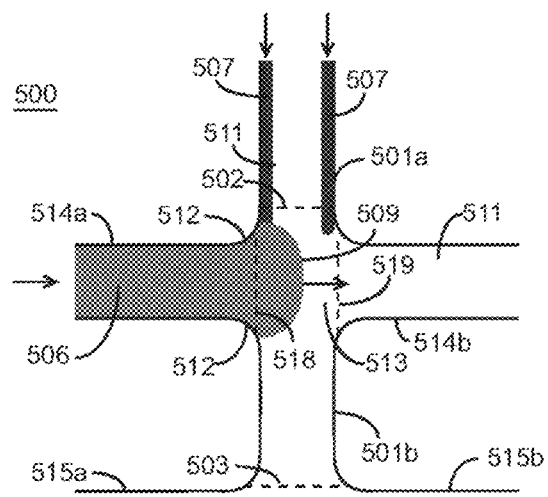

FIG. 5B shows the releasing of the primed passive valve as fluid 509 extends further into intersection 513. The release of fluid at the passive valve was triggered by fluid 507 when it reached and contacted fluid 504 as shown in FIG. 5A. In some cases, after crossing step 502 in channel 501a, fluid 507 may touch and fluidically communicate with fluid 504 of FIG. 5A, resulting in pin release and the protrusion of fluid face 509.

Figure 5C:
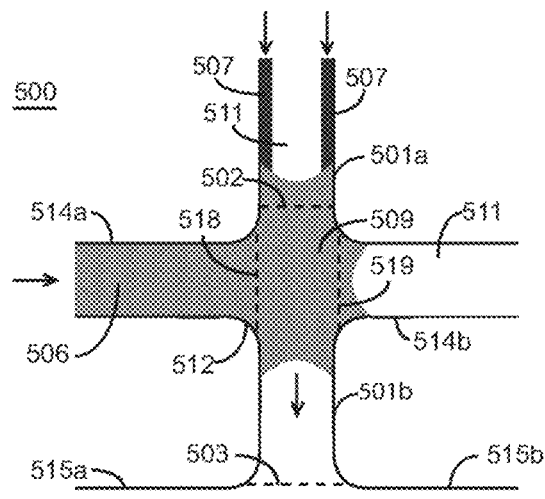
Figure 5D:
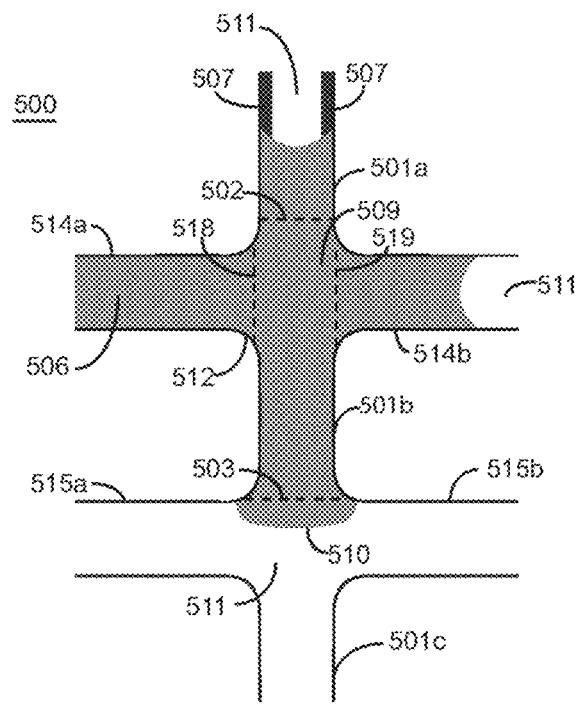

FIG. 5C shows the flow of fluid 506 extending into intersection 513 as well as into channels 501a, 514b and 501b and displacing air 511. FIG. 5D shows further flow of fluid 506 beyond step 503 in channel 501b, to pinning point 516 to form fluid face 510 at intersection 517 against air 511. Channels 515a, 515b and 501c may remain air 511 filled, flow of fluid 507 is stopped and structure 500 may be pinned at intersection 517.

FIG. 6 is a schematic illustration of an alternative approach to providing pinning, useful, for example, in the context of a droplet generating microfluidic device in which aqueous fluids are partitioned into non-aqueous fluids as an emulsion.

Figure 6A:
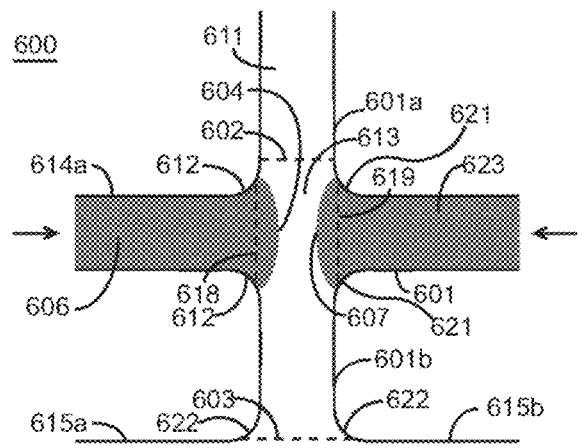
FIGS. 6A-D are schematic illustration of a passive valving microfluidic channel structure in sequential stages of operation.
Figure 6A:
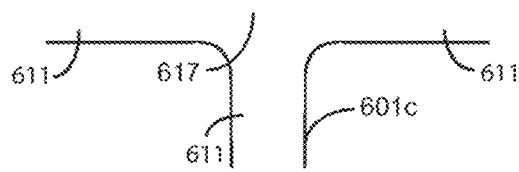

FIGS. 6A-D illustrate an example of a pinning structure arrangement and the process of its operation. FIG. 6A shows an initial pinned state of the fluids in structure 600. First fluid 606 and second fluid 623, which may be surfactant-poor aqueous fluids, are shown within channels 614a and 601 respectively, and are pinned at intersection 613, that may be filled with air 611. Pinning points 612 and 621 serve to hold the fluid in a primed fluid state shown as menisci 604 against air at intersection 613. The pinning points 612 and 621 may be configured and arranged, e.g., as curved corners at intersection 613. The radii of curvature may be adjusted to optimize the action of pinning points 612 and 621 as desired, the action being in a range from slight to strong restraint of fluids 606 and 623 at pinning points 612 and 621 respectively.

Physical and chemical steps may be included within channels or at intersections of channels as required to provide and enable pinning points as described herein. For example, as illustrated in FIGS. 6A-D, steps 602, 603, 618 and/or 619 may be included. Physical steps may provide downward or upward or ramped sections within the systems depending on the optimal action of pinning, the action being in a range from slight to strong. For example, steps 618 and 619 may be raised steps that provide a shallower depth at intersection 613 than for channels 614a and 601, to provide a slight pinning action. Chemical steps may provide regions of high or low hydrophobicity by treatment with different compounds, e.g., fluorinated compounds for high hydrophobicity, depending on the optimal action of pinning, the action being in the range from slight to strong.

Figure 6B:
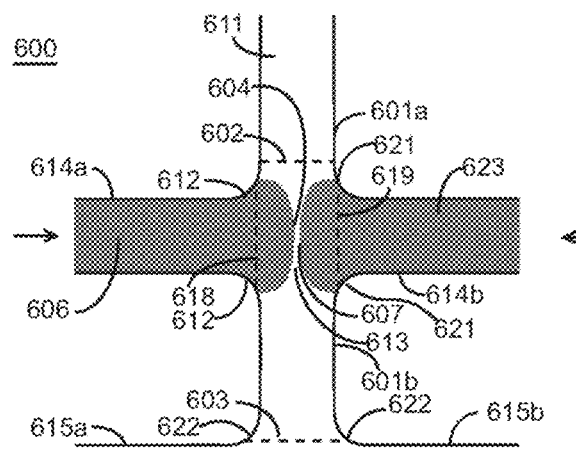
Figure 6B:
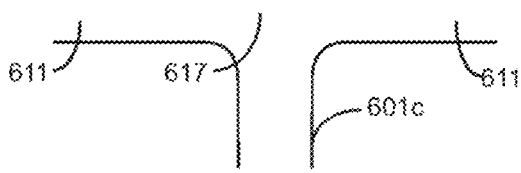

FIG. 6B shows the releasing of the primed pinning points as fluids 606 and 623 extend further into intersection 613. The release of fluid at the pinning points may be triggered, for example, by hydrostatic pressure acting on the fluid or by design of the pinning points to provide only a slight restraint of fluids 606 and 623. After a desired time (e.g., 3, 5, 10, 30, 60, 120, 240 seconds), the menisci may merge and the merged liquid may be re-pinned at a desired location.

The time required for the menisci to merge may be controlled by the hydrostatic pressure acting on the fluids, by the resistance of the microchannels through which the liquids flow, and/or by the aspect ratio of the channels near the junction. For example, when the channels in which the fluids reside are wider and/or deeper than the channel across which they merge, once pinned at the intersection, the menisci may have a shorter distance to travel before they meet. Wider and/or deeper channels may accommodate greater curvature of the pinned menisci, which may allow them to extend further into the intersection. If the fluids wet the channel surface, decreasing the channel depth in the region shown (the region can also extend further down the channels, up to a point where it starts to increase the resistance of the channels appreciably, which may be undesired when it increases the merging time too much) may generate a stronger capillary pressure in the region, which may accelerate the speeds at which the menisci travel and may cause them to merge faster.

After merging of menisci 604 and 621, the combined fluids 606 and 623 may flow further into the structure 600.

Figure 6C:
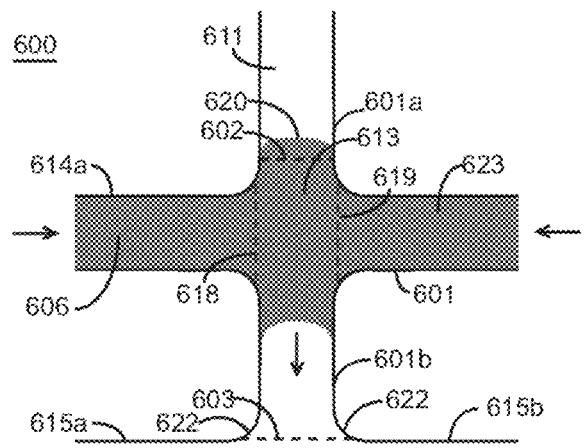

FIG. 6C shows the flow of the combined fluids extending along channel 601a and 601b, beyond intersection 613. Step 602 may include pinning of combined fluids. Step 602 may include meniscus 620.

Figure 6D:
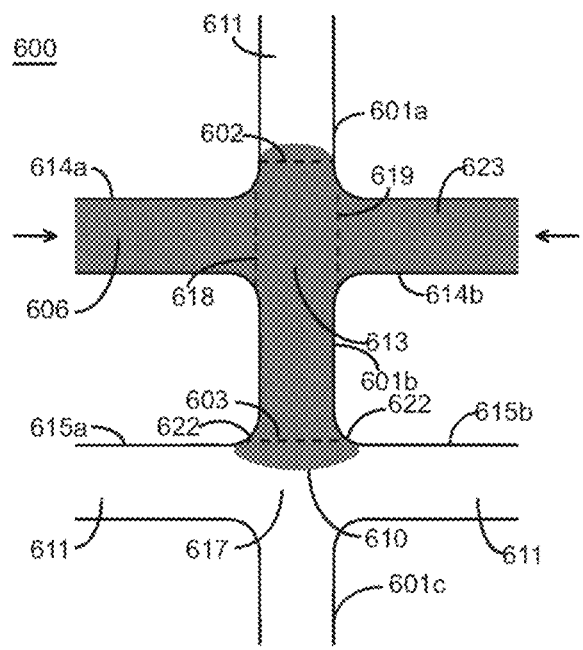

FIG. 6D shows further flow of the combined fluids beyond step 603 in channel 601b, to pinning point 622 to form meniscus 610 at intersection 617 against air 611. Channels 615a, 615b and 601c may remain air 611 filled.

In a further embodiment, stagnation zones that may occur at, for example, pinning points 612 and 621 shown in FIGS. 6A and 6B as a result of steps and may potentially trap undesirable air bubbles. To prevent such bubble formation a pulse of pressure may be applied to the microfluidic channel network to displace air into a well, reservoir, channel or other component of the network.

Additional features may be included in any of the microfluidic channel networks described herein. Features may include, but are not limited to, constrictions, expansions, steps, coatings, etc. One particularly useful feature is an expansion feature for controlling flow rate. In one embodiment the flow rate may be slowed by inclusion of one or more expansion feature in a given channel or at a junction of channels. The expansion feature may be configured in any of a number of ways but generally is provided as a widening or expansion of a portion of a channel or intersection. The shape of the expansion feature may be regular, irregular, short, elongated, staggered, etc. In one embodiment the expansion feature may be trapezoidal in shape. In another embodiment the expansion feature may be triangular, for example, scalene, isosceles, acute, right, equilateral or obtuse.

Channel networks of the present disclosure may include multiple steps, such as at least 1, 2, 3, 4, 5, 6, 7, 8, 9, 10, 20, 30, 40, 50, 60, 70, 80, 90, or 100 steps. The steps may be oriented in order of increase cross-section.

A channel network of the present disclosure may be disposed in an integrated device, such as a microfluidic device (e.g., a cartridge or chip). Such device may be consumable (e.g., a single-use device, which may be disposed). Alternatively, a channel network of the present disclosure may be disposed in multiple devices. Such devices may be configured to integrate with a system that is configured to, for example, facilitate fluid flow.

Figure 7A:
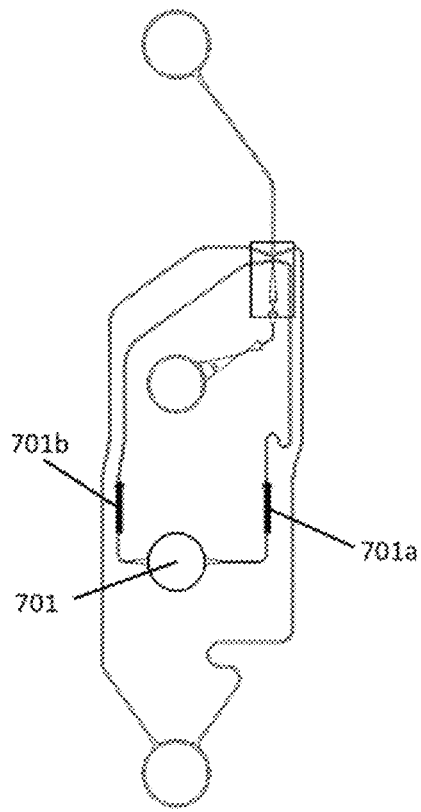

FIGS. 7A-E schematically illustrates an example operation using both passive valving and pinning structure arrangements. FIG. 7A shows an initial resting state of fluid 701. Fluid 701, which may be a surfactant poor (e.g., less than 10%, 5%, 4%, 3%, 2%, 1%, or less (e.g., not detectable) concentration of a surfactant) aqueous fluid containing biological specimens or biological particles (e.g., cells) is shown within channels 701a and 701b. The fluid 701 may, for example, biological particles, such as, for example, one or more cells. Such biological particles may include one or more cells. Each of the one or more cells may include or be enclosed within a gel or polymer matrix.

Figure 7B:
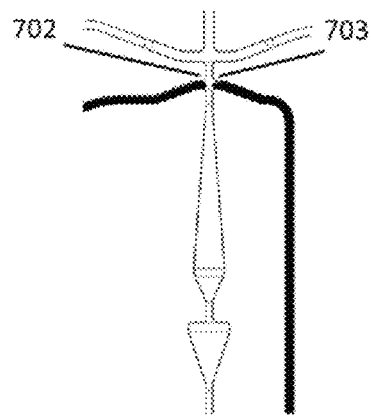

FIG. 7B shows pinning points which may serve to hold the fluid in a primed fluid state shown as menisci 702 and 703. The pinning points may be configured and arranged, e.g., as curved corners at the intersection. The radii of curvature may be adjusted to optimize the action of pinning points as desired, the action being in a range from slight to strong restraint of fluid 701 at the pinning points.

In some examples, the radii of curvature may be from about $1 \times 10^{-8}$ to $1 \times 10^{-1}$ meters (m), from about $1 \times 10^{-7}$ to $1 \times 10^{-2}$ m, from about $1 \times 10^{-6}$ to $1 \times 10^{-3}$ m, from about $1 \times 10^{-6}$ to $1 \times 10^{-4}$ m, or from about $1 \times 10^{-6}$ to $1 \times 10^{-5}$ m.

Figure 7C:
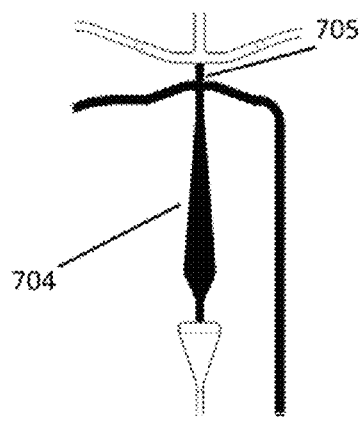

FIG. 7C shows the merging of menisci 702 and 703 and the combined fluids flow further in to the passive valve structure 704. Fluid 701 may also be pinned at the generation step junction 705.

FIG. 7D shows the stepwise addition of a surfactant laden fluid 706. This fluid may comprise beads that comprise further of barcodes and/or other reagents needed for further processing of the biological sample 701. Air or other fluid (e.g., gas) trapped between 701 and 706 may prevent contacts of fluids and may prevent the surfactant laden fluid from wetting the generation region.

FIG. 7E shows the stepwise addition of the fluid 707 which may be used as a partitioning fluid. Fluid 707 may flow through the channels 707a and 707b to fluidically interact with the fluids 701 and 706 at the junction 705. These combinations of fluids may further flow in to channel 708.

Computer Control Systems

Figure 8:
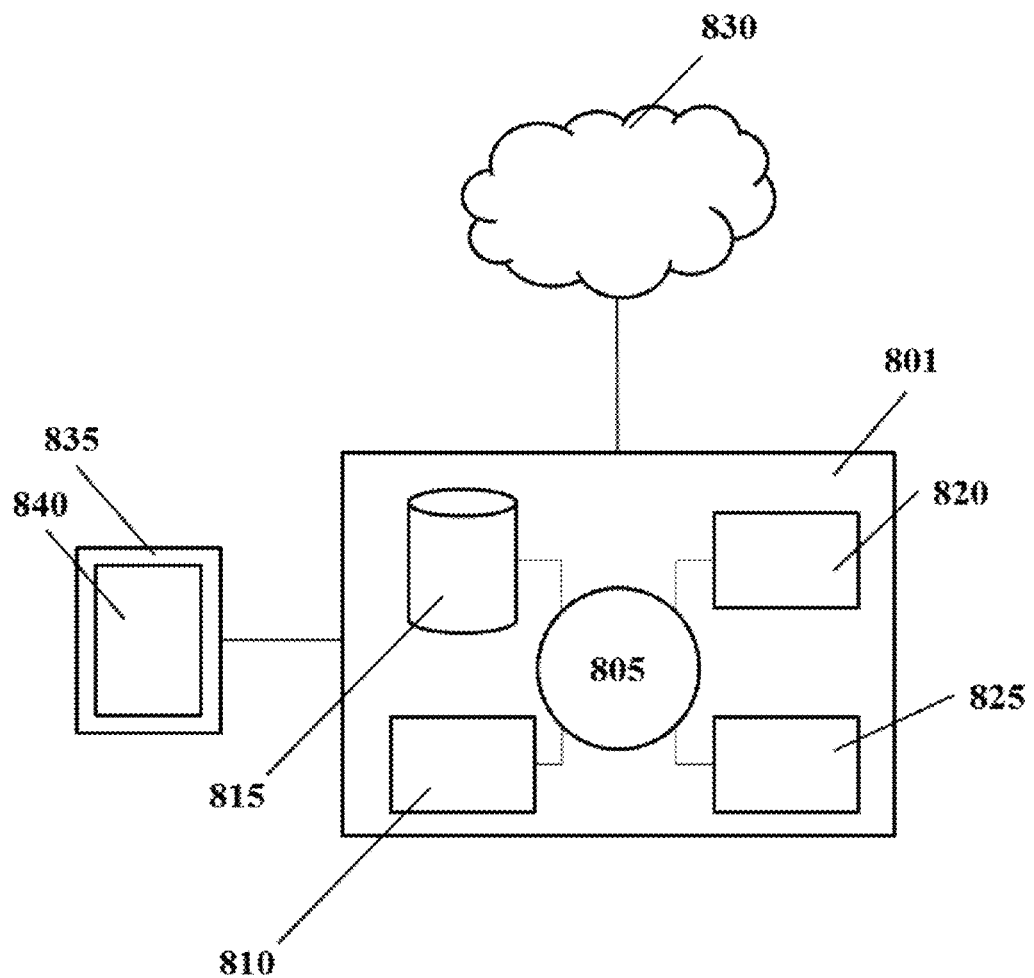
FIG. 8 shows a computer control system that is programmed or otherwise configured to implement methods provided herein.

The present disclosure provides computer control systems that are programmed to implement methods of the disclosure. FIG. 8 shows a computer system 801 that is programmed or otherwise configured to control or regulate the microfluidic system. The computer system 801 can regulate various aspects of the microfluidic system of the present disclosure, such as, for example, the stepwise flow of various fluids through channel segments of a channel network, and/or use negative or positive pressure to subject a fluid to flow through a channel network. The computer system 801 can be an electronic device of a user or a computer system that is remotely located with respect to the electronic device. The electronic device can be a mobile electronic device.

The computer system 801 includes a central processing unit (CPU, also "processor" and "computer processor" herein) 805, which can be a single core or multi core processor, or a plurality of processors for parallel processing. The computer system 801 also includes memory or memory location 810 (e.g., random-access memory, read-only memory, flash memory), electronic storage unit 815 (e.g., hard disk), communication interface 820 (e.g., network adapter) for communicating with one or more other systems, and peripheral devices 825, such as cache, other memory, data storage and/or electronic display adapters. The memory 810, storage unit 815, interface 820 and peripheral devices 825 are in communication with the CPU 805 through a communication bus (solid lines), such as a motherboard. The storage unit 815 can be a data storage unit (or data repository) for storing data. The computer system 801 can be operatively coupled to a computer network ("network") 830 with the aid of the communication interface 820. The network 830 can be the Internet, an internet and/or extranet, or an intranet and/or extranet that is in communication with the Internet. The network 830 in some cases is a telecommunication and/or data network. The network 830 can include one or more computer servers, which can enable distributed computing, such as cloud computing. The network 830, in some cases with the aid of the computer system 801, can implement a peer-to-peer network, which may enable devices coupled to the computer system 801 to behave as a client or a server.

The CPU 805 can execute a sequence of machine-readable instructions, which can be embodied in a program or software. The instructions may be stored in a memory location, such as the memory 810. The instructions can be directed to the CPU 805, which can subsequently program or otherwise configure the CPU 805 to implement methods of the present disclosure. Examples of operations performed by the CPU 805 can include fetch, decode, execute, and writeback.

The CPU 805 can be part of a circuit, such as an integrated circuit. One or more other components of the system 801 can be included in the circuit. In some cases, the circuit is an application specific integrated circuit (ASIC).

The storage unit 815 can store files, such as drivers, libraries and saved programs. The storage unit 815 can store user data, e.g., user preferences and user programs. The computer system 801 in some cases can include one or more additional data storage units that are external to the computer system 801, such as located on a remote server that is in communication with the computer system 801 through an intranet or the Internet.

The computer system 801 can communicate with one or more remote computer systems through the network 830. For instance, the computer system 801 can communicate with a remote computer system of a user (e.g., technician or researcher). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 801 via the network 830.

Methods as described herein can be implemented by way of machine (e.g., computer processor) executable code stored on an electronic storage location of the computer system 801, such as, for example, on the memory 810 or electronic storage unit 815. The machine executable or machine readable code can be provided in the form of software. During use, the code can be executed by the processor 805. In some cases, the code can be retrieved from the storage unit 815 and stored on the memory 810 for ready access by the processor 805. In some situations, the electronic storage unit 815 can be precluded, and machine-executable instructions are stored on memory 810.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 801, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 801 can include or be in communication with an electronic display 835 that comprises a user interface (UI) 840 for providing, for example, a sample readout, such as results upon assaying a biological sample, or instructions for using systems of the present disclosure to process a biological sample(s). Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 805.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A microfluidic system, comprising:
a first channel segment fluidly connecting a source of disruptable particles with a droplet forming junction, the first channel segment comprising a constricted region proximal to the droplet forming junction;
a second channel segment in fluid communication with the droplet forming junction and first channel segment, wherein the first channel segment and second channel segment meet at a first intersection upstream of the droplet forming junction and downstream of the constricted region; and
a flow control system for driving the disruptable particles through the constricted region, wherein the constricted region comprises a cross sectional dimension reduced sufficiently to induce disruption of the disruptable particles driven through the constricted region, and for flowing the disrupted particles and a fluid from the second channel segment into the droplet formation junction, whereby for each of the disrupted particles, at least a portion of the disrupted particle and the fluid from the second channel segment are encapsulated into a droplet, wherein the droplet contains at least a portion of only one disrupted particle.

2. The system of claim 1, further comprising a fourth channel segment in fluid communication with the first channel segment and disposed between the first intersection and the droplet forming junction.

3. The system of claim 2, further comprising a fifth, sixth and seventh channel segment intersecting the fourth channel segment at a second intersection, wherein the fourth channel segment has a first depth at the droplet forming junction and the seventh channel segment and/or second intersection has a second depth that is greater than the first depth; and wherein the flow control system directs the disruptable particles and fluid from the first and second channel segments and partitioning fluid from the fifth and sixth channel segments into the second intersection.

4. The system of claim 1, wherein the constricted region is positioned at a distance of less than 100 microns away from the droplet formation junction.

5. The system of claim 1, wherein the constricted region is positioned at a distance of less than 50 microns away from the droplet formation junction.

6. The system of claim 1, wherein the constricted region is positioned at a distance of less than 20 microns away from the droplet formation junction.

7. The system of claim 1, wherein the constricted region is positioned at a distance of less than 10 microns away from the droplet formation junction.

8. The system of claim 1, further comprising a third channel segment fluidly connecting a source of disruptable particles with the droplet forming junction, the third channel segment comprising a constricted region proximal to the droplet forming junction;
wherein the third channel segment meets the second channel segment and first channel segment at the first intersection.

9. The system of claim 1, wherein the fluid from the second channel segment comprises reagents and/or beads.

* * * * *